US009220671B2

(12) United States Patent
Ascione et al.

(10) Patent No.: US 9,220,671 B2
(45) Date of Patent: Dec. 29, 2015

(54) DYE COMPOSITION COMPRISING AT LEAST FOUR DYE PRECURSORS INCLUDING AT LEAST ONE OXIDATION BASE AND AT LEAST ONE COUPLER

(75) Inventors: Jean-Marc Ascione, Paris (FR); Jean-Baptiste Saunier, Paris (FR); Anne-Marie Couroux, Saint Ouen l'aumone (FR); Delphine Allard, Paris (FR); Valérie Nicou, Clichy (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 13/994,278

(22) PCT Filed: Dec. 14, 2011

(86) PCT No.: PCT/EP2011/072673
§ 371 (c)(1),
(2), (4) Date: Sep. 24, 2013

(87) PCT Pub. No.: WO2012/080289
PCT Pub. Date: Jun. 21, 2012

(65) Prior Publication Data
US 2014/0007358 A1      Jan. 9, 2014

Related U.S. Application Data

(60) Provisional application No. 61/432,729, filed on Jan. 14, 2011.

(30) Foreign Application Priority Data

Dec. 17, 2010   (FR) ...................................... 10 60767

(51) Int. Cl.
*A61Q 5/10*      (2006.01)
*A61K 8/49*      (2006.01)

(52) U.S. Cl.
CPC .............. *A61K 8/4946* (2013.01); *A61K 8/492* (2013.01); *A61K 8/494* (2013.01); *A61K 8/4926* (2013.01); *A61Q 5/10* (2013.01)

(58) Field of Classification Search
CPC ........... A61Q 5/10; A61K 8/49; A61K 8/494; A61K 8/4946; A61K 2800/88; C07D 231/52; C07D 403/12; C07D 471/104
USPC ............... 8/405, 406, 408, 409; 546/249, 121
See application file for complete search history.

(56) References Cited

U.S. PATENT DOCUMENTS

| | | | |
|---|---|---|---|
| 4,003,699 A | 1/1977 | Rose et al. | |
| RE30,199 E | 1/1980 | Rose et al. | |
| 4,823,985 A | 4/1989 | Grollier et al. | |
| 5,254,135 A * | 10/1993 | Lang et al. | 8/408 |
| 5,457,200 A | 10/1995 | Zimmermann et al. | |
| 5,534,267 A | 7/1996 | Neunhoeffer et al. | |
| 5,663,366 A | 9/1997 | Neunhoeffer et al. | |
| 5,938,792 A | 8/1999 | Lang et al. | |
| 6,099,592 A | 8/2000 | Vidal et al. | |
| 6,099,593 A | 8/2000 | Terranova et al. | |
| 6,284,003 B1 | 9/2001 | Rose et al. | |
| 6,338,741 B1 | 1/2002 | Vidal et al. | |
| 6,645,258 B2 | 11/2003 | Vidal et al. | |
| 2002/0050013 A1 | 5/2002 | Vidal et al. | |
| 2003/0019051 A9 | 1/2003 | Vidal et al. | |
| 2005/0166335 A1 | 8/2005 | Vidal et al. | |
| 2007/0136959 A1 | 6/2007 | Fadli | |
| 2007/0143935 A1 | 6/2007 | Fadli et al. | |
| 2008/0071092 A1 | 3/2008 | Vidal et al. | |
| 2010/0115711 A1 | 5/2010 | Fadli et al. | |
| 2013/0048007 A1 * | 2/2013 | Fadli | 132/208 |

FOREIGN PATENT DOCUMENTS

| | | | |
|---|---|---|---|
| DE | 23 59 399 | 6/1975 | |
| DE | 38 43 892 | 6/1990 | |
| DE | 41 33 957 | 4/1993 | |
| DE | 195 43 988 | 5/1997 | |
| EP | 0 425 345 | 5/1991 | |
| EP | 0 550 656 | 4/1997 | |
| EP | 0 770 375 | 5/1997 | |
| EP | 1 550 656 | 7/2005 | |
| EP | 1 792 606 | 6/2007 | |
| EP | 1 792 903 | 6/2007 | |
| EP | 1792903 A1 * | 6/2007 | ............... A61Q 5/10 |
| FR | 2 586 913 | 3/1987 | |
| FR | 2 733 749 | 11/1996 | |
| FR | 2 750 048 | 12/1997 | |
| GB | 1 026 978 | 4/1966 | |
| GB | 1 153 196 | 5/1969 | |
| JP | 2-19576 | 1/1990 | |
| JP | 05-163124 | 6/1993 | |
| WO | 92/05764 | 4/1992 | |
| WO | 92/18093 | 10/1992 | |
| WO | 94/08969 | 4/1994 | |
| WO | 94/08970 | 4/1994 | |
| WO | 96/15765 | 5/1996 | |
| WO | WO 2010/133640 A2 * | 11/2010 | ............... A61K 8/41 |

OTHER PUBLICATIONS

STIC Search Report dated Dec. 3, 2013.*

* cited by examiner

*Primary Examiner* — Eisa Elhilo
(74) *Attorney, Agent, or Firm* — The Marbury Law Group, PLLC

(57) ABSTRACT

The present invention relates to a dye composition comprising at least four oxidation dye precursors, including at least one oxidation base chosen from suitably selected pyrazolopyridines and diamino-N,N-dihydropyrazolone derivatives and at least one coupler chosen from suitably selected cationic 3,5-diaminopyridines and 4-aminoindoles, 5-amino-6-chloro-2-methylphenol, 6-hydroxybenzomorpholine, 2-methyl-5-hydroxyethylaminophenol and 2-amino-3-hydroxypyridine, and also to the dyeing process using this composition. The present invention makes it possible in particular to obtain a composition for dyeing keratin fibers that is suitable for use in oxidation dyeing and that can produce colorations in varied shades, which are strong or chromatic, powerful, aesthetic, sparingly selective, and resistant to the various attacking factors to which the hair may be subjected, such as shampoo, sweat, permanent reshaping and light. The composition in accordance with the invention moreover shows good harmlessness and good stability.

22 Claims, No Drawings

DYE COMPOSITION COMPRISING AT LEAST FOUR DYE PRECURSORS INCLUDING AT LEAST ONE OXIDATION BASE AND AT LEAST ONE COUPLER

This is a national stage application of PCT/EP2011/072673, filed internationally on Dec. 14, 2011, which claims priority to U.S. Provisional Application No. 61/432,729, filed on Jan. 14, 2011; as well as French Application FR 1060767, filed on Dec. 17, 2010.

The present invention relates to a dye composition comprising at least four oxidation dye precursors, including at least one oxidation base chosen from suitably selected pyrazolopyridines and diamino-N,N-dihydropyrazolone derivatives and at least one coupler chosen from suitably selected cationic 3,5-diaminopyridines and 4-aminoindoles, 5-amino-6-chloro-2-methylphenol, 6-hydroxybenzomorpholine, 2-methyl-5-hydroxyethylaminophenol and 2-amino-3-hydroxypyridine, and also to the dyeing process using this composition.

It is known practice to dye keratin fibres, and in particular human keratin fibres such as the hair, with dye compositions containing oxidation dye precursors, which are generally known as oxidation bases, such as ortho- or para-phenylenediamines, ortho- or para-aminophenols and heterocyclic compounds. These oxidation bases are colourless or weakly coloured compounds, which, when combined with oxidizing products, may give rise to coloured compounds via a process of oxidative condensation.

It is also known that the shades obtained with these oxidation bases may be varied by combining them with couplers or colouration modifiers, the latter being chosen especially from aromatic meta-diamines, meta-aminophenols, meta-diphenols and certain heterocyclic compounds such as indole compounds.

The variety of molecules used as oxidation bases and couplers allows a wide range of colours to be obtained.

The "permanent" colouration obtained by virtue of these oxidation dyes is required, moreover, to meet a certain number of demands. Thus it should have no toxicological drawbacks, it should allow shades to be obtained in the desired intensity, and it should show good resistance to external agents such as light, bad weather, washing, permanent waving treatments, perspiration and rubbing.

The dyes should also allow grey hair to be covered and, finally, they should be as unselective as possible, i.e. they should produce the smallest possible differences in colouration along the same keratin fibre, which in general is differently sensitized (i.e. damaged) between its end and its root.

It is already known practice to use oxidation bases derived from 3-aminopyrazolo[1,5-a]pyridine in the field of dyeing keratin fibres, especially the oxidation bases of formulae (I) and (II) below. In particular, such bases are disclosed in documents EP 1 792 903 and EP 1 792 606.

It is also known practice to use oxidation bases of the diamino-N,N-dihydropyrazolone type in the field of dyeing keratin fibres, especially the hair. In particular, such a base is described in document EP 1 550 656.

It is also known practice, in documents EP 0 425 345 and WO 92/18093, to use derivatives of aminoindole type, and in particular 7-methyl-1H-indol-4-amine and 7-ethyl-1H-indol-4-amine for dyeing keratin fibres, and in particular the hair.

However, the prior art dye compositions lead to colourations that are not entirely satisfactory, especially in terms of intensity, chromaticity, selectivity and fastness with respect to external agents.

The aim of the present invention is to obtain a hair dye composition that has improved dyeing properties, especially in terms of intensity and/or chromaticity and/or selectivity and/or resistance to external agents.

This aim is achieved with the present invention, one subject of which is a composition for dyeing keratin fibres, comprising, in a cosmetically acceptable medium, at least four oxidation dye precursors, including:
A) at least one oxidation base chosen from:
A1) the pyrazolopyridines of formula (I), the pyrazolopyridines of formula (II), and also the addition salts thereof, solvates thereof or solvates of the salts thereof:

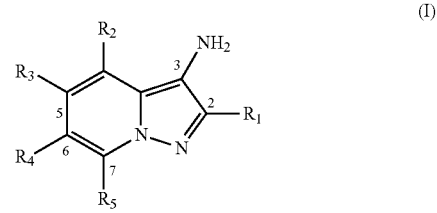

in which:
$R_1$, $R_2$, $R_3$, $R_4$ and $R_5$, which may be identical or different, represent a hydrogen or halogen atom; a radical —$NHSO_3H$; a hydroxyl radical; a radical ($C_1$-$C_4$)alkyl; a radical ($C_1$-$C_4$)alkoxy; a radical ($C_1$-$C_4$)alkylthio; mono($C_1$-$C_4$)alkylamino; a radical di($C_1$-$C_4$)alkylamino in which the two alkyl groups may form, together with the nitrogen atom to which they are attached, a ring that may be interrupted with one or more nitrogen, oxygen or sulfur atoms; a heterocycle; a nitro radical; a phenyl radical; a carbonyl radical; a ($C_1$-$C_4$)alkoxycarbonyl radical; a carboxamido radical; a cyano radical; an amino radical; a sulfonyl radical; a radical —$CO_2H$, a radical —$SO_3H$; a radical —$PO_3H_2$; a radical —$PO_4H_2$; or a group:

in which R''' represents an oxygen or nitrogen atom, Q represents an oxygen atom, a group NH or NH($C_1$-$C_4$)alkyl, and Y represents a hydroxyl, amino, $C_1$-$C_4$ alkyl, ($C_1$-$C_4$)alkoxy, ($C_1$-$C_4$)alkylamino or di($C_1$-$C_4$)alkylamino radical;

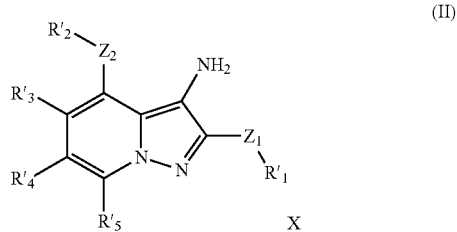

in which:
$Z_1$ and $Z_2$ independently represent:
 a covalent single bond;
 a divalent radical chosen from:
  a radical —$O(CH_2)_p$—, p denoting an integer ranging from 0 to 6;

a radical —NR'$_6$(CH$_2$)$_q$(C$_6$H$_4$)$_t$—, q denoting an integer ranging from 0 to 6 and t denoting 0 or 1, R'$_6$ representing a hydrogen atom or a C$_1$-C$_6$ alkyl radical optionally substituted with one or more hydroxyl groups;

Z$_1$ may also represent a divalent radical —S—, —SO— or —SO$_2$— when R'$_1$ is a methyl radical;

R'$_1$ and R'$_2$ independently represent:

a hydrogen;

a C$_1$-C$_{10}$ alkyl radical, which is optionally substituted and optionally interrupted with a heteroatom or a group chosen from O, N, Si, S, SO and SO$_2$;

a halogen;

an SO$_3$H radical;

a 5- to 8-membered ring which is substituted or unsubstituted, saturated, unsaturated or aromatic, optionally containing one or more heteroatoms or groups chosen from N, O, S, SO$_2$ and —CO—, the ring possibly being cationic and/or substituted with a cationic radical;

a group —N$^+$R$_{17}$R$_{18}$R$_{19}$, R$_{17}$, R$_{18}$ and R$_{19}$ being linear or branched C$_1$-C$_5$ alkyls optionally substituted with one or more hydroxyl groups;

when Z$_1$ or, respectively, Z$_2$ represents a covalent bond, then R'$_1$ or, respectively, R'$_2$ may also represent a radical:

optionally substituted C$_1$-C$_6$ alkylcarbonyl;

—O—CO—R, —CO—O—R, NR—CO—R' or —CO—NRR' in which R and R' independently represent a hydrogen atom or an optionally substituted C$_1$-C$_6$ alkyl radical;

R'$_3$, R'$_4$ and R'$_5$, which may be identical or different, represent:

a hydrogen atom;

a hydroxyl radical;

a C$_1$-C$_6$ alkoxy radical;

a C$_1$-C$_6$ alkylthio radical;

an amino radical;

a monoalkylamino radical;

a C$_1$-C$_6$ dialkylamino radical in which the alkyl radicals may form, with the nitrogen atom to which they are attached, a saturated, unsaturated, aromatic or non-aromatic 5- to 8-membered heterocycle, which may contain one or more heteroatoms or groups chosen from N, O, S, SO$_2$ and CO, the heterocycle possibly being cationic, and/or substituted with a cationic radical;

an optionally substituted C$_1$-C$_6$ alkylcarbonyl radical;

a radical —O—CO—R, —CO—O—R, NR—CO—R' or —CO—NRR' with R and R' as defined previously;

a halogen;

a —NHSO$_3$H radical;

an optionally substituted C$_1$-C$_4$ alkyl radical;

a saturated, unsaturated or aromatic, optionally substituted carbon-based ring;

R'$_3$, R'$_4$ and R'$_5$, may form in pairs a partially saturated or unsaturated ring;

X represents an ion or group of ions that provides the electronegativity of the derivative of formula (II);

with the proviso that at least one of the groups R'$_1$ and R$_2$ represents a cationic radical; and A2) the diamino-N,N-dihydropyrazolone derivatives of formula (III), and also the addition salts thereof, solvates thereof or solvates of the salts thereof:

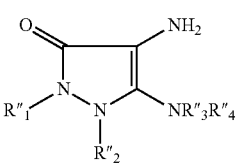

in which:

R"$_1$, R"$_2$, R"$_3$ and R"$_4$, which may be identical or different, represent:

a linear or branched C$_1$-C$_6$ alkyl radical optionally substituted with one or more radicals chosen from the group consisting of a radical OR"$_5$, a radical NR"$_6$R"$_7$, a carboxyl radical, a sulfonic radical, a carboxamido radical CONR"$_6$R"$_7$, a sulfonamido radical SO$_2$NR"$_6$R"$_7$, a heteroaryl, an aryl optionally substituted with one or more (C$_1$-C$_4$)alkyl, hydroxyl, C$_1$-C$_2$ alkoxy, amino or (di)alkyl(C$_1$-C$_2$) amino groups;

an aryl radical optionally substituted with one or more (C$_1$-C$_4$)alkyl, hydroxyl, C$_1$-C$_2$ alkoxy, amino or (di)alkyl(C$_1$-C$_2$)amino;

a 5- or 6-membered heteroaryl radical, optionally substituted with one or more radicals chosen from (C$_1$-C$_4$)alkyl and (C$_1$-C$_2$)alkoxy;

R"$_3$ and R"$_4$ may also represent a hydrogen atom;

R"$_5$, R"$_6$ and R"$_7$, which may be identical or different, represent:

a hydrogen atom;

a linear or branched C$_1$-C$_4$ alkyl radical optionally substituted with one or more radicals chosen from hydroxyl, C$_1$-C$_2$ alkoxy, carboxamido CONR"$_8$R"$_9$, sulfonyl SO$_2$R"$_8$, aryl optionally substituted with a (C$_1$-C$_4$)alkyl, hydroxyl, C$_1$-C$_2$ alkoxy, amino or (di)alkyl(C$_1$-C$_2$)amino; aryl optionally substituted with a (C$_1$-C$_4$)alkyl, hydroxyl, C$_1$-C$_2$ alkoxy, amino or (di)alkyl(C$_1$-C$_2$)amino;

R"$_6$ and R"$_7$, which may be identical or different, may also represent a carboxamido radical CONR"$_8$R"$_9$; a sulfonyl radical SO$_2$R"$_8$;

R"$_8$ and R"$_9$, which may be identical or different, represent a hydrogen atom; a linear or branched C$_1$-C$_4$ alkyl radical optionally substituted with one or more hydroxyl or C$_1$-C$_2$ alkoxy;

R"$_1$ and R"$_2$, on the one hand, and R"$_3$ and R"$_4$, on the other hand, may form, with the nitrogen atom(s) to which they are attached, a saturated or unsaturated 5- to 7-membered heterocycle optionally substituted with one or more radicals chosen from the group consisting of halogen atoms and amino, (di) alkyl(C$_1$-C$_4$)amino, hydroxyl, carboxyl, carboxamido and (C$_1$-C$_2$)alkoxy radicals, C$_1$-C$_4$ alkyl radicals optionally substituted with one or more hydroxyl, amino, (di)alkylamino, alkoxy, carboxyl or sulfonyl radicals;

R"$_3$ and R"$_4$ may also form, together with the nitrogen atom to which they are attached, a 5- or 7-membered heterocycle in which the carbon atoms may be replaced with an optionally substituted oxygen or nitrogen atom; and B) at least one coupler chosen from:

B1) derivatives of the cationic aminopyridine type of formula (IV), and also the addition salts thereof, solvates thereof or solvates of the salts thereof:

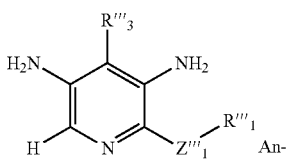

(IV)

in which the group $Z'''_1R'''_1$ bears the cationic charge;

$Z'''_1$ is an oxygen atom or a group $NR'''_2$;

$R'''_2$ is a hydrogen atom or a linear or branched $C_1$-$C_4$ alkyl radical, a benzyl radical or an acetyl radical;

$R'''_1$ is a saturated, linear or branched $C_1$-$C_{10}$ alkyl radical, substituted or interrupted with a cationic radical, optionally interrupted with one or more oxygen atoms and/or with one or more groups $NR'''_2$, optionally substituted with one or more radicals chosen from hydroxyl, alkoxy and $C_1$-$C_4$ hydroxyalkyl radicals or $R'''_1$ is a saturated, and saturated or aromatic 5- to 8-membered heterocycle optionally substituted with one or more radicals chosen from $C_1$-$C_4$ alkyl, hydroxyl, $C_1$-$C_4$ alkoxy, amino, $(C_1$-$C_4)$alkylamino, di$(C_1$-$C_4)$alkylamino, thio, $(C_1$-$C_4)$alkylthio, carboxyl, $(C_1$-$C_4)$alkylcarbonyl, sulfonyl, amido and $C_1$-$C_4$ hydroxyalkyl radicals;

when $Z'''_1$ represents $NR'''_2$, then $R'''_1$ and $R'''_2$ may form, together with the nitrogen atom to which they are attached, a cationic, saturated or unsaturated 5- to 8-membered heterocycle, optionally substituted with one or more radicals chosen from $C_1$-$C_{10}$ alkyl radicals, hydroxyl, $C_1$-$C_4$ alkoxy, amino, $(C_1$-$C_4)$alkylamino, di$(C_1$-$C_4)$alkylamino, thio, $(C_r$-$C_4)$alkylthio, carboxyl, $(C_1$-$C_4)$alkylcarbonyl, sulfonyl, amido and $C_1$-$C_4$ hydroxyalkyl radicals, this heterocycle possibly containing one or more heteroatoms chosen from N and O, preferably N, or $R'''_1$ and $R'''_2$ may form, together with the nitrogen atom to which they are attached, a non-cationic, saturated or unsaturated 5- to 8-membered heterocycle, substituted with a cationic radical and optionally substituted with one or more radicals chosen from $C_1$-$C_{10}$ alkyl radicals, hydroxyl, $C_1$-$C_4$ alkoxy, amino, $(C_1$-$C_4)$alkylamino, di$(C_1$-$C_4)$alkylamino, thio, $(C_1$-$C_4)$alkylthio, carboxyl, $(C_1$-$C_4)$alkylcarbonyl, sulfonyl, amido and $C_1$-$C_4$ hydroxyalkyl radicals;

$R'''_3$ is chosen from a hydrogen atom, halogens chosen from fluorine, chlorine and bromine, linear or branched $C_1$-$C_4$ alkyl radicals, carboxyl (—COOH) and $(C_1$-$C_4)$alkoxycarbonyl radicals;

An- represents an anion or a mixture of anions;

B2) the 4-aminoindole derivatives of formula (V), and also the addition salts thereof, solvates thereof or solvates of the salts thereof:

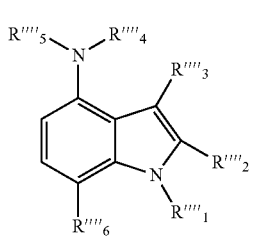

(V)

in which:

$R''''_1$ represents:
a hydrogen atom;
a linear or branched, saturated $C_1$-$C_6$ alkyl radical, optionally interrupted with an oxygen atom or a radical $NR''''_7$, optionally substituted with a radical chosen from OH and $NR''''_7R''''_8$;

$R''''_2$ and $R''''_3$, which may be identical or different, represent:
a hydrogen atom;
a $C_1$-$C_6$ and preferably $C_1$-$C_4$ alkyl radical, optionally substituted with one or more hydroxyl radicals;
a $C_1$-$C_6$ alkyl carboxylate radical;
a carboxyl radical;
a radical $CONR''''_7R''''_8$;

$R''''_4$ and $R''''_5$, which may be identical or different, represent:
a hydrogen atom;
a $C_1$-$C_6$ alkyl radical;

$R''''_6$ represents:
a halogen;
a linear or branched $C_1$-$C_{10}$ alkyl radical, optionally interrupted with a heteroatom chosen from O and $NR''''_9$, and/or optionally substituted with one or more radicals, which may be identical or different, chosen from OH and $NR''''_7R''''_8$;
a carboxyl radical;
a $C_1$-$C_{10}$ alkyl carboxylate radical;
a radical $CONR''''_7R''''_8$;
a $C_1$-$C_{10}$ alkoxy radical or a $C_1$-$C_{10}$ (poly)hydroxyalkoxy radical;
a (poly)$(C_1$-$C_{10})$alkoxy$(C_1$-$C_{10})$alkyloxy radical;
a radical O-Ak-$NR''''_8R''''_{10}$ with Ak=linear $C_1$-$C_8$ or branched $C_3$-$C_8$ divalent alkylene radical, optionally interrupted with one or more oxygen atoms and/or groups $NR''''_7$;

$R''''_7$ and $R''''_8$, which may be identical or different, represent:
a hydrogen atom;
a $C_1$-$C_8$ alkyl radical optionally substituted with one or more hydroxyl radicals;

$R''''_9$ and $R''''_{10}$, which may be identical or different, represent a linear or branched, saturated or unsaturated $C_1$-$C_4$ alkyl; $R''''_9$ and $R''''_{10}$ may form, with the nitrogen that bears them, a saturated or unsaturated 5- to 8-membered heterocycle, one of the chain members possibly being an oxygen atom or a radical $NR''''_{11}$ with $R''''_{11}$=H or $C_1$-$C_4$ alkyl, optionally substituted with one or more radicals chosen from OH and $NR''''_7R''''_8$.

B3) 5-amino-6-chloro-2-methylphenol of formula (VI), and the addition salts thereof, solvates thereof or solvates of the salts thereof:

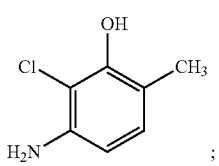

(VI)

B4) 6-hydroxybenzomorpholine of formula (VII), and the addition salts thereof, solvates thereof or solvates of the salts thereof:

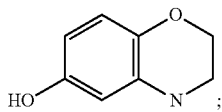

B5) 2-methyl-5-hydroxyethylaminophenol of formula (VIII), and the addition salts thereof, solvates thereof or solvates of the salts thereof:

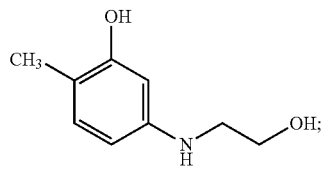

and
B6) 2-amino-3-hydroxypyridine of formula (IX), and the addition salts thereof, solvates thereof or solvates of the salts thereof:

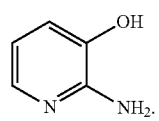

A subject of the invention is also a dyeing process using this composition.

Another subject of the invention is the use of the composition of the present invention for dyeing keratin fibres, and in particular human keratin fibres such as the hair.

The present invention relates to multi-compartment dyeing devices comprising compositions using at least four oxidation dye precursors, including at least one oxidation base chosen from suitably selected pyrazolopyridines and diamino-N,N-dihydropyrazolone derivatives and at least one coupler chosen from suitably selected cationic 3,5-diaminopyridines and 4-aminoindoles, 5-amino-6-chloro-2-methyl phenol, 6-hydroxybenzomorpholine, 2-methyl-5-hydroxyethylaminophenol and 2-amino-3-hydroxypyridine, or the addition salts thereof, solvates thereof or solvates of the salts thereof.

The present invention makes it possible in particular to obtain a composition for dyeing keratin fibres that is suitable for use in oxidation dyeing and that can produce colourations in varied shades, which are strong or chromatic, powerful, aesthetic, sparingly selective, and resistant to the various attacking factors to which the hair may be subjected, such as shampoo, sweat, permanent reshaping and light. The composition in accordance with the invention moreover shows good harmlessness and good stability.

In the context of the present invention, the term "at least one" is equivalent to "one or more".

The present invention also covers the mesomeric forms and the stereoisomers of the various oxidation dyes of the invention.

It should be noted that, in the text hereinbelow, unless otherwise indicated, the limits of a range of values are included in that range.

In the context of the invention, and unless indicated otherwise, the term "alkyl" used for the alkyl radicals and also for the groups comprising an alkyl part means a linear or branched carbon-based chain comprising from 1 to 4 carbon atoms, which is unsubstituted or substituted with one or more heterocycles, or with one or more phenyl groups or with one or more groups chosen from halogen atoms such as chlorine, bromine, iodine and fluorine; hydroxyl, alkoxy, amino, carbonyl, carboxamido, sulfonyl, $-CO_2H$, $-SO_3H$, $-PO_3H_2$, $-PO_4H_2$, $-NHSO_3H$, sulfonamide, mono($C_1$-$C_4$)alkylamino or tri($C_1$-$C_4$)alkylammonium radicals, or alternatively with a di($C_1$-$C_4$)alkylamino radical in which the two alkyl groups may form, together with the nitrogen atom of the said di($C_1$-$C_4$)alkylamino group to which they are attached, a ring that may be interrupted with one or more nitrogen, oxygen or sulfur atoms.

Similarly, according to the invention, the term "alkoxy" used for the alkoxy radicals and also for the groups comprising an alkoxy part means a linear or branched O-carbon-based chain comprising from 1 to 4 carbon atoms, which is unsubstituted or substituted with one or more groups chosen from heterocycles; halogen atoms such as chlorine, bromine, iodine and fluorine; hydroxyl, amino, carbonyl, carboxamido, sulfonyl, $-CO_2H$, $-SO_3H$, $-PO_3H_2$, $-PO_4H_2$, $-NHSO_3H$, sulfonamide, mono($C_1$-$C_4$)alkylamino or tri ($C_1$-$C_4$)alkylammonium radicals, or alternatively with a di($C_1$-$C_4$)alkylamino radical in which the two alkyl groups may form, together with the nitrogen atom of the said di($C_1$-$C_4$)alkylamino group to which they are attached, a ring that may be interrupted with one or more nitrogen, oxygen or sulfur atoms.

According to the invention, the term "heterocycle" means an aromatic or non-aromatic 5-, 6-, 7- or 8-membered ring containing from 1 to 3 heteroatoms chosen from nitrogen, sulfur and oxygen atoms. These heterocycles may be fused to other heterocycles or to a phenyl group. They may be substituted with a halogen atom; a ($C_1$-$C_4$) alkyl radical; a ($C_1$-$C_4$) alkoxy radical; a hydroxyl radical; an amino radical; a ($C_1$-$C_4$)alkylamino radical; a di($C_1$-$C_4$)alkylamino radical in which the two alkyl groups may form, together with the nitrogen atom to which they are attached, a ring that may be interrupted with one or more nitrogen, oxygen or sulfur atoms. These heterocycles may also be quaternized with a ($C_1$-$C_4$)alkyl radical.

Among these optionally fused heterocycles, examples that may especially be mentioned include the following rings: thiadiazole, triazole, isoxazole, oxazole, azaphosphole, thiazole, isothiazole, imidazole, pyrazole, triazine, thiazine, pyrazine, pyridazine, pyrimidine, pyridine, diazepine, oxazepine, benzotriazole, benzoxazole, benzimidazole, benzothiazole, morpholine, piperidine, piperazine, azetidine, pyrrolidine, aziridine, 3-(2-hydroxyethyl)benzothiazol-3-ium, 1-(2-hydroxyethyl)pyridinium.

According to the invention, the term "phenyl" means a phenyl radical that is unsubstituted or substituted with one or more cyano, carbonyl, carboxamido, sulfonyl, $-CO_2H$, $-SO_3H$, $-PO_3H_2$, $-PO_4H_2$, hydroxyl, amino or mono($C_1$-$C_4$)alkylamino radicals, or di($C_1$-$C_4$)alkylamino radicals in which the two alkyl groups may form, together with the nitrogen atom of the said di($C_1$-$C_4$)alkylamino group to which they are attached, a ring that may be interrupted with one or more nitrogen, oxygen or sulfur atoms.

Among the groups

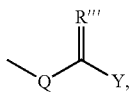

mention may be made especially of acetamide, dimethylurea, O-methylcarbamate, methylcarbonate and N-dimethylcarbamate groups, and the esters.

Among the compounds of formula (I) above, preference is given to the 3-aminopyrazolo[1,5-a]pyridines corresponding to formula (I') below, and also the addition salts thereof, solvates thereof or solvates of the salts thereof:

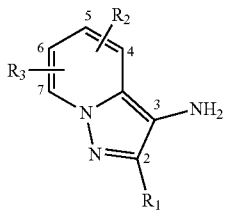

(I')

in which:
$R_1$, $R_2$ and $R_3$, which may be identical or different, represent a hydrogen or halogen atom; a hydroxyl radical; a ($C_1$-$C_4$) alkyl radical; a ($C_1$-$C_4$)alkylthio radical; a ($C_1$-$C_4$)alkoxy radical; a —$NHSO_3H$ radical; an amino radical; a ($C_1$-$C_4$) alkylamino radical; a di($C_1$-$C_4$)alkylamino radical in which the two alkyl groups may form, together with the nitrogen atom to which they are attached, a ring that may be interrupted with one or more nitrogen, oxygen or sulfur atoms; a heterocycle as defined previously; a sulfonamide radical, a carbonyl radical, a ($C_1$-$C_4$)alkoxycarbonyl radical, a carboxamido radical, or a group of formula:

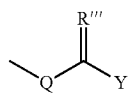

in which R'" represents an oxygen or nitrogen atom, Q represents an oxygen atom, a group NH or NH($C_1$-$C_4$)alkyl, and Y represents a hydroxyl, amino, $C_1$-$C_4$ alkyl, ($C_1$-$C_4$)alkoxy, ($C_1$-$C_4$)alkylamino or di($C_1$-$C_4$)alkylamino radical.

Among the 3-aminopyrazolo[1,5-a]pyridines of formula (I), which may be used as oxidation base in the dye compositions in accordance with the invention, mention may be made especially of:
pyrazolo[1,5-a]pyridin-3-ylamine;
2-acetylaminopyrazolo[1,5-a]pyridin-3-ylamine;
2-morpholin-4-ylpyrazolo[1,5-a]pyridin-3-ylamine;
3-aminopyrazolo[1,5-a]pyridine-2-carboxylic acid;
2-methoxypyrazolo[1,5-a]pyridin-3-ylamino;
(3-aminopyrazolo[1,5-a]pyridin-7-yl)methanol;
2-(3-aminopyrazolo[1,5-a]pyridin-5-yl)ethanol;
2-(3-aminopyrazolo[1,5-a]pyridin-7-yl)ethanol;
(3-aminopyrazolo[1,5-a]pyridin-2-yl)methanol;
3,6-diaminopyrazolo[1,5-a]pyridine;
3,4-diaminopyrazolo[1,5-a]pyridine;
pyrazolo[1,5-a]pyridine-3,7-diamine;
7-morpholin-4-ylpyrazolo[1,5-a]pyridin-3-ylamine;
pyrazolo[1,5-a]pyridine-3,5-diamine;
5-morpholin-4-ylpyrazolo[1,5-a]pyridin-3-ylamine;
2-[(3-aminopyrazolo[1,5-a]pyridin-5-yl)(2-hydroxyethyl) amino]ethanol;
2-[(3-aminopyrazolo[1,5-a]pyridin-7-yl)(2-hydroxyethyl) amino]ethanol;
3-aminopyrazolo[1,5-a]pyridin-5-ol;
3-aminopyrazolo[1,5-a]pyridin-4-ol;
3-aminopyrazolo[1,5-a]pyridin-6-ol;
3-aminopyrazolo[1,5-a]pyridin-7-ol;
2-methoxy-6,7-dimethylpyrazolo[1,5-a]pyridin-3-amine;
2-[(3-aminopyrazolo[1,5-a]pyridin-2-yl)oxy]ethanol;
4-ethyl-2-methoxy-7-methylpyrazolo[1,5-a]pyridin-3-amine hydrochloride;
1-(3-aminopyrazolo[1,5-a]pyridin-2-yl)pyrrolidin-3-ol;
2,2'-[(3-aminopyrazolo[1,5-a]pyridin-2-yl)imino]diethanol;
2-[(3-aminopyrazolo[1,5-a]pyridin-2-yl)amino]ethanol;
N2-(2-pyridin-3-ylethyl)pyrazolo[1,5-a]pyridine-2,3-diamine;
and the addition salts thereof, solvates thereof or solvates of the salts thereof.

Among the bases described above, 2-[(3-aminopyrazolo[1,5-a]pyridin-2-yl)oxy]ethanol, and the addition salts thereof, solvates thereof or solvates of the salts thereof, are particularly preferred.

For the vast majority, the 3-aminopyrazolo[1,5-a]pyridines of formula (I) are compounds that are known in the pharmaceutical field, and are described especially in U.S. Pat. No. 5,457,200. These compounds may be prepared according to synthetic methods that are well known in the literature and as described, for example, in U.S. Pat. No. 5,457,200.

The term "cationic ring or heterocycle" means a ring containing one or more quaternary ammonium groups.

Examples of radicals of the type —$N^+R_{17}R_{18}R_{19}$ that may be mentioned include trimethylammonium, triethylammonium, dimethylethylammonium, diethylmethylammonium, diisopropylmethylammonium, diethylpropylammonium, β-hydroxyethyldiethylammonium, bis(β-hydroxyethyl)methylammonium and tris(β-hydroxyethyl)ammonium radicals.

Examples of cationic heterocyclic radicals include imidazolium, pyridinium, piperazinium, pyrrolidinium, morpholinium, pyrimidinium, thiazolium, benzimidazolium, benzothiazolium, oxazolium, benzotriazolium, pyrazolium, triazolium and benzoxazolium radicals.

Examples of cationic heterocycles that may be mentioned include imidazoliums, pyridiniums, piperaziniums, pyrrolidiniums, morpholiniums, pyrimidiniums, thiazoliums, benzimidazoliums, benzothiazoliums, oxazoliums, benzotriazoliums, pyrazoliums, triazoliums and benzoxazoliums.

The compounds of formula (II) may optionally be salified with strong mineral acids, for instance HCl, HBr, HI, $H_2SO_4$ or $H_3PO_4$, or organic acids, for instance acetic acid, lactic acid, tartaric acid, citric acid, succinic acid, benzenesulfonic acid, para-toluenesulfonic acid, formic acid or methanesulfonic acid.

If they contain anionic groups such as —$CO_2H$, —$SO_3H$, —$PO_3H_2$ or —$PO_4H_2$ groups, the compounds of formula (I) may be salified with alkali metal or alkaline-earth metal hydroxides such as sodium hydroxide or potassium hydroxide, with aqueous ammonia or with organic amines.

The compounds of formula (I) or (II) may also be in the form of solvates, for example a hydrate or a solvate of a linear or branched alcohol such as ethanol or isopropanol.

As examples of derivatives of formula (II), mention may be made of the following compounds in which $X^-$ is as defined previously:

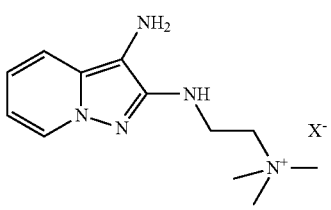

salt of [2-(3-aminopyrazolo[1,5-a]pyridin-2-ylamino)ethyl]trimethylammonium

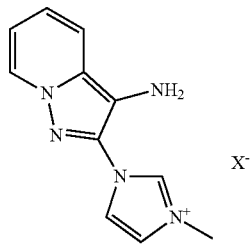

salt of 3-(3-aminopyrazolo[1,5-a]pyridin-2-yl)-1-methyl-3H-imidazol-1-ium

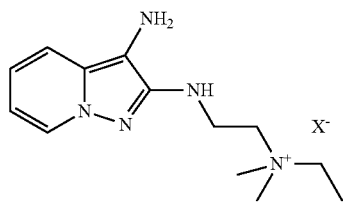

salt of [2-(3-aminopyrazolo[1,5-a]pyridin-2-ylamino)ethyl]ethyldimethylammonium

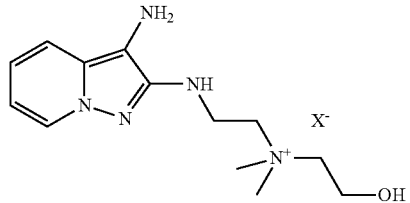

salt of [2-(3-aminopyrazolo[1,5-a]pyridin-2-ylamino)ethyl](2-hydroxyethyl)dimethylammonium

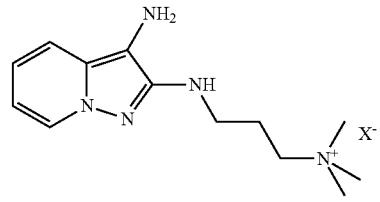

salt of [3-(3-aminopyrazolo[1,5-a]pyridin-2-ylamino)propyl]trimethylammonium

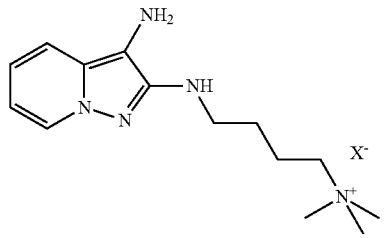

salt of [4-(3-aminopyrazolo[1,5-a]pyridin-2-ylamino)butyl]trimethylammonium

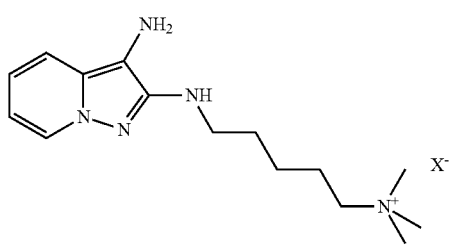

salt of [5-(3-aminopyrazolo[1,5-a]pyridin-2-ylamino)pentyl]trimethylammonium

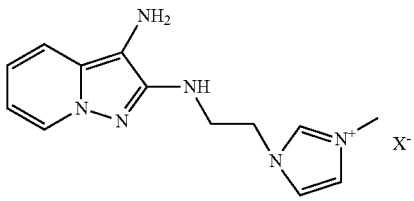

salt of 3-[2-(3-aminopyrazolo[1,5-a]pyridin-2-ylamino)ethyl]-1-methyl-3H-imidazol-1-ium

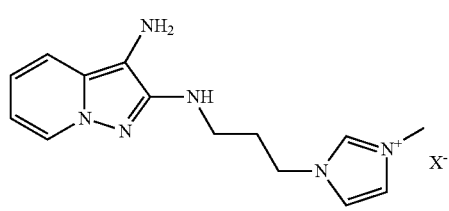

salt of 3-[3-(3-aminopyrazolo[1,5-a]pyridin-2-ylamino)propyl]-1-methyl-3H-imidazol-1-ium

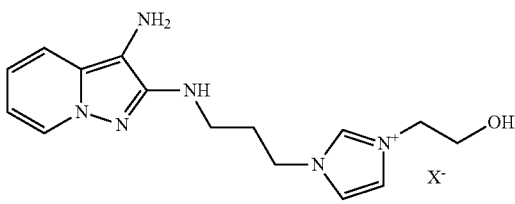

salt of 3-[3-(3-aminopyrazolo[1,5-a]pyridin-2-ylamino)propyl]-1-(2-hydroxyethyl)-3H-imidazol-1-ium

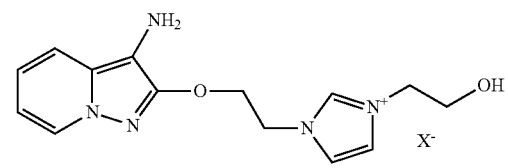

salt of 3-[2-(3-aminopyrazolo[1,5-a]pyridin-2-yloxy)ethyl]-1-(2-hydroxyethyl)-3H-imidazol-1-ium

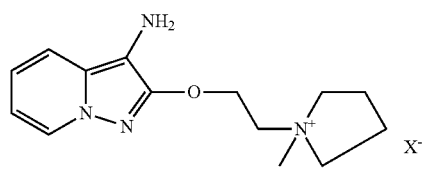

salt of 1-{2-[(3-aminopyrazolo[1,5-a]pyridin-2-yl)oxy]ethyl}-1-methylpyrrolidinium -continued

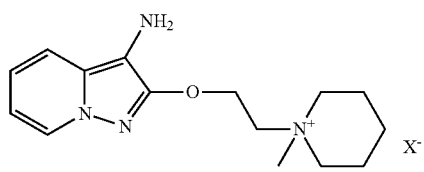

salt of 1-{2-[(3-aminopyrazolo[1,5-a]pyridin-2-yl)oxy]ethyl}-1-methylpiperidinium

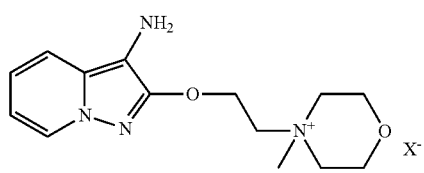

salt of 4-{2-[(3-aminopyrazolo[1,5-a]pyridin-2-yl)oxy]ethyl}-4-methylmorpholin-4-ium

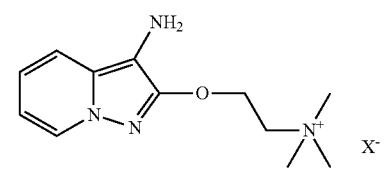

salt of {2-[(3-aminopyrazolo[1,5-a]pyridin-2-yl)oxy]ethyl}trimethylammonium

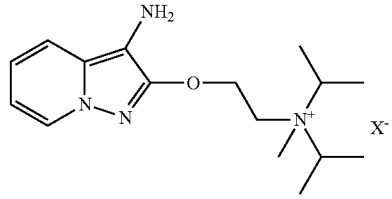

salt of {2-[(3-aminopyrazolo[1,5-a]pyridin-2-yl)oxy]ethyl}diisopropylmethylammonium

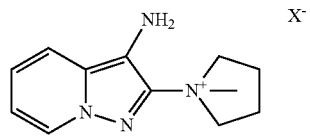

salt of 1-(3-aminopyrazolo[1,5-a]pyridin-2-yl)-1-methylpyrrolidinium

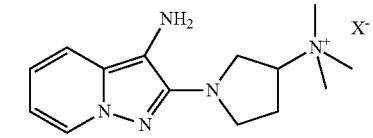

salt of [1-(3-aminopyrazolo[1,5-a]pyridin-2-yl)pyrrolidin-3-yl]trimethylammonium

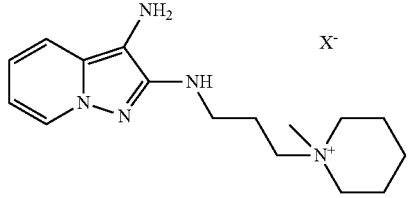

salt of 1-[3-(3-aminopyrazolo[1,5-a]pyridin-2-ylamino)propyl]-1-methylpiperidinium -continued

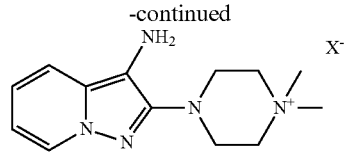

salt of 4-(3-aminopyrazolo[1,5-a]pyridin-2-yl)-1,1-dimethylpiperazin-1-ium

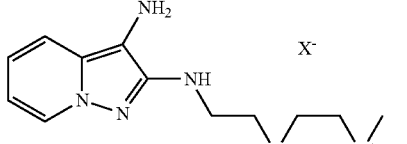

salt of 4-[2-(3-aminopyrazolo[1,5-a]pyridin-2-ylamino)ethyl]-1,1-dimethylpiperazin-1-ium

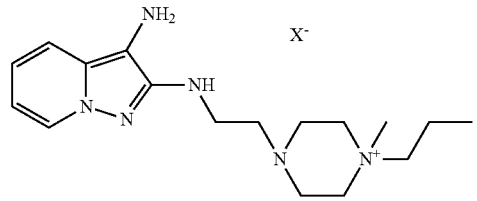

salt of 4-[2-(3-aminopyrazolo[1,5-a]pyridin-2-ylamino)ethyl]-1-methyl-1-propylpiperazin-1-ium

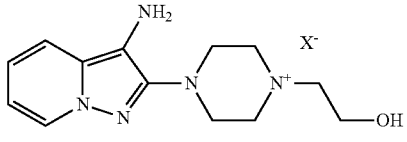

salt of 4-(3-aminopyrazolo[1,5-a]pyridin-2-yl)-1-(2-hydroxyethyl)piperazin-1-ium

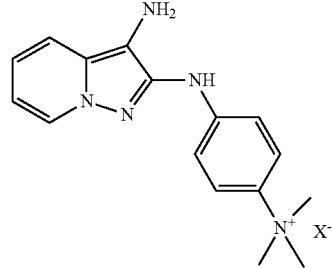

salt of [4-(3-aminopyrazolo[1,5-a]pyridin-2-ylamino)phenyl]trimethylammonium

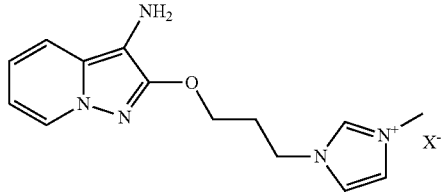

salt of 3-[3-(3-aminopyrazolo[1,5-a]pyridin-2-yloxy)propyl]-1-methyl-3H-imidazol-1-ium

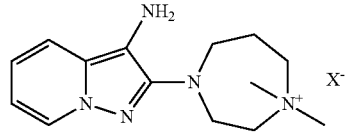

salt of 4-(3-aminopyrazolo[1,5-a]pyridin-2-yl)-1,1-dimethyl[1,4]diazepan-1-ium

-continued

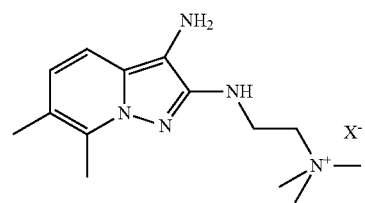

salt of [2-(3-amino-6,7-dimethylpyrazolo
[1,5-a]-pyridin-2-ylamino)ethyl]
trimethylammonium

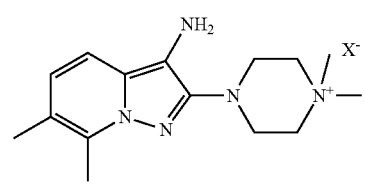

salt of 4-(3-amino-6,7-dimethylpyrazolo[1,5-a]-
pyridin-2-yl)-1,1-dimethylpiperazin-1-ium

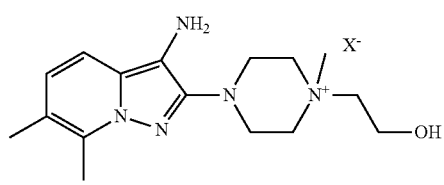

salt of 4-(3-amino-6,7-dimethylpyrazolo[1,5-a]-pyridin-
2-yl)-1-(2-hydroxyethyl)-1-methylpiperazin-1-ium

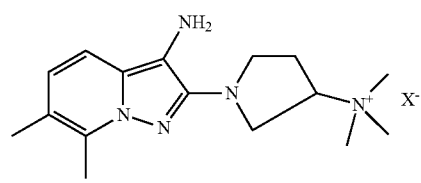

salt of [1-(3-amino-6,7-dimethylpyrazolo[1,5-a]-
pyridin-2-yl)pyrrolidin-3-yl]trimethylammonium

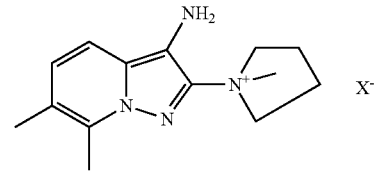

salt of 1-(3-amino-6,7-dimethylpyrazolo[1,5-a]-
pyridin-2-yl)-1-methylpyrrolidinium

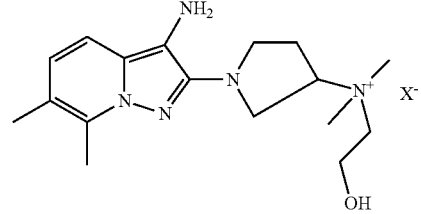

salt of [1-(3-amino-6,7-dimethylpyrazolo[1,5-a]-
pyridin-2-yl)pyrrolidin-3-yl](2-hydroxyethyl)
dimethylammonium -continued

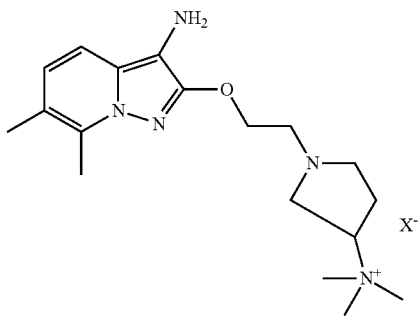

salt of {1-[2-(3-amino-6,7-dimethylpyrazolo[1,5-a]-
pyridin-2-yloxy)ethyl]pyrrolidin-3yl}trimethylammonium

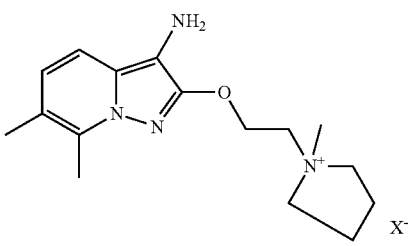

salt of 1-{2-[(3-amino-6,7-dimethylpyrazolo[1,5-a]-
pyridin-2-yl)oxy]ethyl}-1-methylpyrrolidinium

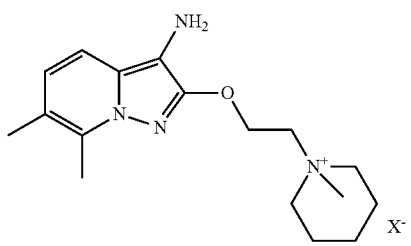

salt of 1-{2-[(3-amino-6,7-dimethylpyrazolo[1,5-a]-
pyridin-2-yl)oxy]ethyl}-1-methylpiperidinium

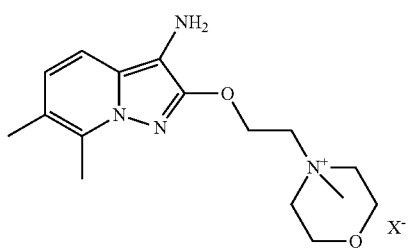

salt of 4-{2-[(3-amino-6,7-dimethylpyrazolo[1,5-a]-
pyridin-2-yl)oxy]ethyl}-4-methylmorpholin-4-ium

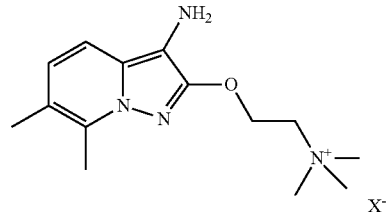

salt of {2-[(3-amino-6,7-dimethylpyrazolo[1,5-a]-
pyridin-2-yl)oxy]ethyl}trimethylammonium -continued

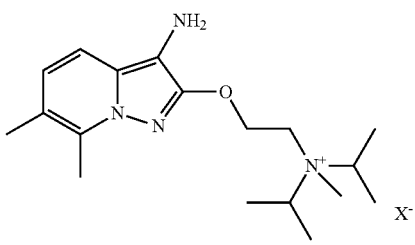

salt of {2-[(3-amino-6,7-dimethylpyrazolo[1,5-a]-pyridin-2-yl)oxy]ethyl}diisopropylmethylammonium

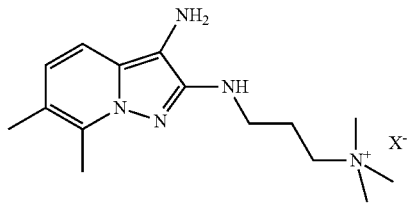

salt of [3-(3-amino-6,7-dimethylpyrazolo[1,5-a]-pyridin-2-ylamino)propyl]trimethylammonium

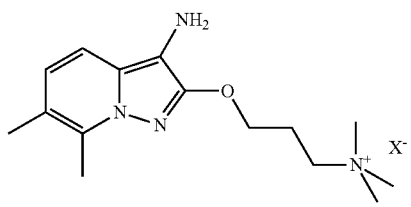

salt of [3-(3-amino-6,7-dimethylpyrazolo[1,5-a]-pyridin-2-yloxy)propyl]trimethylammonium

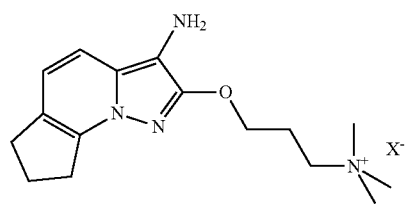

salt of [3-(3-amino-7,8-dihydro-6H-cyclopenta[e]pyrazolo[1,5-a]-pyridin-2-yloxy)propyl]trimethylammonium

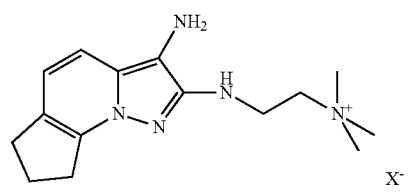

salt of {2-[(3-amino-7,8-dihydro-6H-cyclopenta[e]pyrazolo[1,5-a]-pyridin-2-yl)amino]ethyl}trimethylammonium

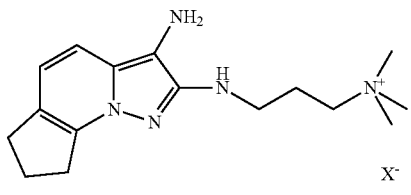

salt of {3-[(3-amino-7,8-dihydro-6H-cyclopenta[e]pyrazolo[1,5-a]-pyridin-2-yl)amino]propyl}trimethylammonium -continued

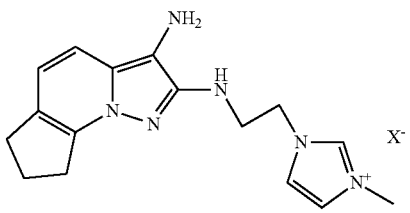

salt of 1-{2-[(3-amino-7,8-dihydro-6H-cyclopenta[e]pyrazolo[1,5-a]-pyridin-2-yl)amino]ethyl}-3-methyl-1H-imidazol-3-ium

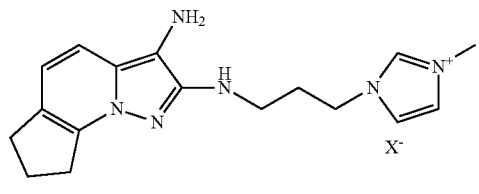

salt of 1-{3-[(3-amino-7,8-dihydro-6H-cyclopenta[e]pyrazolo[1,5-a]-pyridin-2-yl)amino]propyl}-3-methyl-1H-imidazol-3-ium

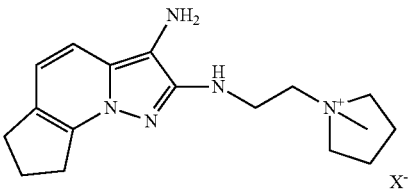

salt of 1-{2-[(3-amino-7,8-dihydro-6H-cyclopenta[e]pyrazolo[1,5-a]-pyridin-2-yl)amino]ethyl}-1-methylpyrrolidinium

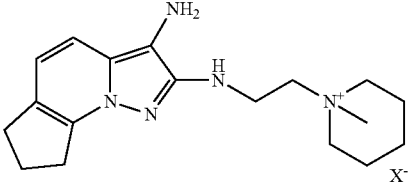

salt of 1-{2-[(3-amino-7,8-dihydro-6H-cyclopenta[e]pyrazolo[1,5-a]-pyridin-2-yl)amino]ethyl}-1-methylpiperidinium

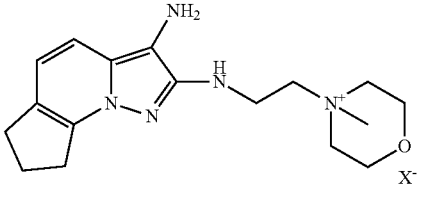

salt of 4-{2-[(3-amino-7,8-dihydro-6H-cyclopenta[e]pyrazolo[1,5-a]-pyridin-2-yl)amino]ethyl}-4-methylmorpholin-4-ium

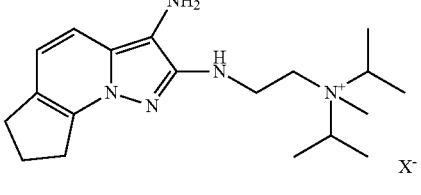

salt of {2-[(3-amino-7,8-dihydro-6H-cyclopenta[e]pyrazolo[1,5-a]-pyridin-2-yl)amino]ethyl}diisopropylmethylammonium

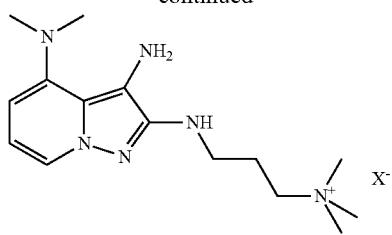

salt of [3-(3-amino-4-dimethylaminopyrazolo
[1,5-a]-pyridin-2-ylamino)
propyl]trimethylammonium

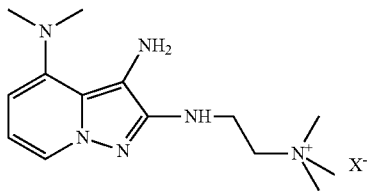

salt of [2-(3-amino-4-dimethylaminopyrazolo
[1,5-a]-pyridin-2-ylamino)
ethyl]trimethylammonium

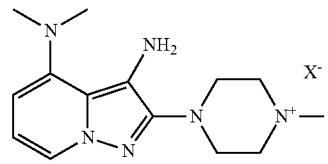

salt of 4-(3-amino-4-dimethylaminopyrazolo
[1,5-a]-pyridin-2-yl)-1-methylpiperazin-1-ium

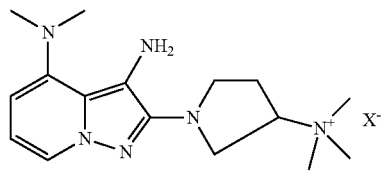

salt of [1-(3-amino-4-dimethylaminopyrazolo
[1,5-a]-pyridin-2-yl)pyrrolidin-3-yl]
trimethylammonium

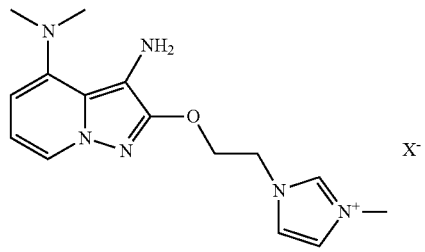

salt of 3-[2-(3-amino-4-dimethylaminopyrazolo[1,5-a]-
pyridin-2-yloxy)ethyl]-1-methyl-3H-imidazol-1-ium

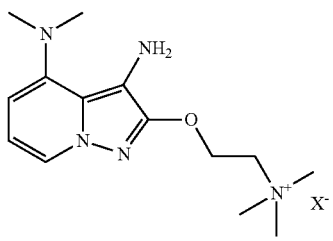

salt of [2-(3-amino-4-dimethylaminopyrazolo
[1,5-a]-pyridin-2-yloxy)ethyl]
trimethylammonium

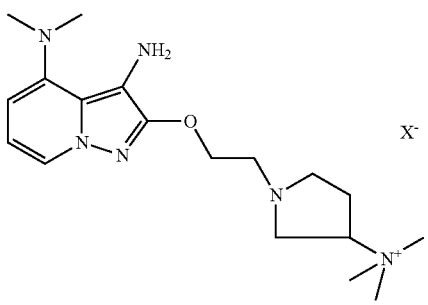

salt of {1-[2-(3-amino-4-dimethylaminopyrazolo[1,5-a]-
pyridin-2-yloxy)ethyl]pyrrolidin-3-yl}trimethylammonium

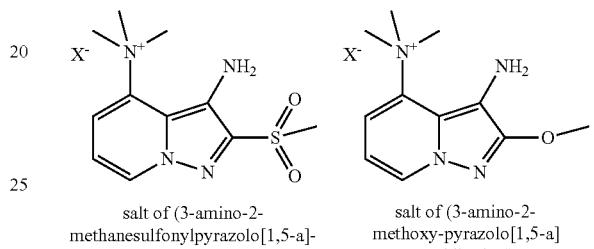

salt of (3-amino-2-
methanesulfonylpyrazolo[1,5-a]-
pyridin-4-yl)
trimethylammonium salt of (3-amino-2-
methoxy-pyrazolo[1,5-a]
pyridin-4-yl)
trimethylammonium The nature of the counterion is not a determining factor regarding the dyeing power of the compounds of formula (II).

When $R'_1$ or $R'_2$ denotes a heterocycle, this heterocycle is preferably a cationic heterocycle or a heterocycle substituted with a cationic radical. By way of example, mention may be made of imidazole is substituted with a quaternary ammonium radical or imidazoliums, piperazines substituted with a quaternary ammonium radical or piperaziniums, pyrrolidines substituted with a quaternary ammonium radical or pyrrolidiniums, and diazepanes substituted with a quaternary ammonium radical or diazepaniums.

According to a difference embodiment, $R'_1$ or $R'_2$ represents a group —$N^+R_{17}R_{18}R_{19}$, $R_{17}$, $R_{18}$ and $R_{19}$ being linear or branched $C_1$-$C_5$ alkyls optionally substituted with one or more hydroxyl groups, such as trialkylammonium, tri(hydroxyalkyl)ammonium, hydroxyalkyldialkylammonium or di(hydroxyalkyl)alkylammonium.

The radicals $R'_3$, $R'_4$ and $R'_5$, independently, may be a hydrogen atom or an optionally substituted $C_1$-$C_4$ alkyl radical. By way of example, mention may be made of methyl, ethyl, hydroxyethyl, aminoethyl, propyl and butyl radicals. According to one particular embodiment, $R'_3$, $R'_4$ and $R'_5$ independently represent a hydrogen atom or a $C_1$-$C_4$ alkyl radical.

According to one particular embodiment, $R'_4$ and $R'_5$ together form a partially saturated or unsaturated 5- or 8-membered ring, especially a cyclopentene or cyclohexene, which is optionally substituted.

According to one particular embodiment, the compound of formula (II) corresponds to formula (II') below:

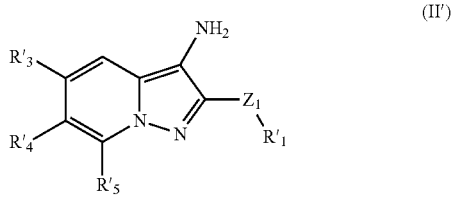

in which $Z_1$, $R'_3$, $R'_4$ and $R'_5$ are as defined previously.

According to one particular embodiment of this formula, $Z_1$ represents a covalent bond, a radical —$NR'_6(CH_2)_q$— or a radical —$O(CH_2)_p$— and $R'_1$ is a cationic radical.

As cationic oxidation bases of formula (II), the following bases are most particularly preferred:

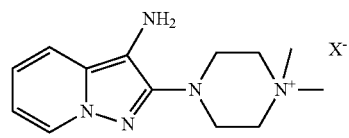

Salt of 4-(3-amino-pyrazolo[1,5-a]pyridin-2-yl)-1,1-dimethyl-piperazin-1-ium

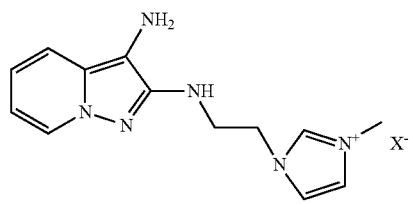

Salt of 3-[2-(3-amino-pyrazolo[1,5-a]pyridin-2-ylamino)ethyl]-1-methyl-3H-imidazol-1-ium and the addition salts thereof, solvates thereof or solvates of the salts thereof.

In the context of the invention, the term "alkyl radical" means linear or branched alkyl radicals, which are preferably $C_1$-$C_{10}$ unless otherwise mentioned, preferentially $C_1$-$C_6$ and preferably $C_1$-$C_4$, such as methyl, ethyl, propyl, isopropyl, isobutyl, tert-butyl, pentyl or hexyl radicals.

More particularly, in formula (III), the radicals $R''_1$ and $R''_2$, which may be identical or different, are chosen from:

a $C_1$-$C_6$ and preferably $C_1$-$C_4$ alkyl radical, optionally substituted with a hydroxyl, a ($C_1$-$C_2$)alkoxy, an amino or a (di)($C_1$-$C_2$)alkylamino;

a phenyl, methoxyphenyl, ethoxyphenyl or benzyl radical.

Preferably, the radicals $R''_1$ and $R''_2$, which may be identical or different, are chosen from methyl, ethyl, 2-hydroxyethyl, 3-hydroxypropyl, 2-hydroxypropyl and phenyl radicals.

According to another embodiment, the radicals $R''_1$ and $R''_2$ form, together with the nitrogen atoms to which they are attached, a saturated or unsaturated, 5- or 6-membered, optionally substituted ring.

Preferably, the radicals $R''_1$ and $R''_2$ form, together with the nitrogen atoms to which they are attached, a pyrazolidine or pyridazolidine ring, optionally substituted with one or more $C_1$-$C_4$ alkyl, hydroxyl, ($C_1$-$C_2$)alkoxy, carboxyl, carboxamido, amino or (di)($C_1$-$C_2$)alkylamino radicals.

Even more advantageously, $R''_1$ and $R''_2$ form, together with the nitrogen atoms to which they are attached, a pyrazolidine or pyridazolidine ring.

As regards the radicals $R''_3$ and $R''_4$, these radicals, which may be identical or different, are more particularly chosen from a hydrogen atom; a linear or branched $C_1$-$C_6$ and preferably $C_1$-$C_4$ alkyl radical, optionally substituted with one or more hydroxyl, ($C_1$-$C_2$)alkoxy, amino or (di)($C_1$-$C_2$)alkylamino; a phenyl radical optionally substituted with one or more hydroxyl, amino or ($C_1$-$C_2$)alkoxy radicals.

Preferably, the radicals $R''_3$ and $R''_4$, which may be identical or different, are chosen from a hydrogen atom and methyl, ethyl, isopropyl, 2-hydroxyethyl, 3-hydroxypropyl, 2-hydroxypropyl and 2-carboxyethyl radicals. According to one particular embodiment, the radicals $R''_3$ and $R''_4$ represent a hydrogen atom.

According to another embodiment, the radicals $R''_3$ and $R''_4$ form, together with the nitrogen atom to which they are attached, a 5- or 7-membered ring chosen from pyrrolidine, piperidine, homopiperidine, piperazine and homopiperazine heterocycles; the said rings possibly being substituted with one or more hydroxyl, amino, (di)($C_1$-$C_2$)alkylamino, carboxyl, carboxamido or $C_1$-$C_4$ alkyl radicals optionally substituted with one or more hydroxyl, amino or $C_1$-$C_2$ (di)alkylamino radicals.

More particularly, the radicals $R''_3$ and $R''_4$ form, together with the nitrogen atom to which they are attached, a 5- or 7-membered ring chosen from pyrrolidine, 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-aminopyrrolidine, 3-methylaminopyrrolidine, 3-dimethylaminopyrrolidine, 4-amino-3-hydroxypyrrolidine, 3-hydroxy-4-(2-hydroxyethyl)aminopyrrolidine, piperidine, 2,6-dimethylpiperidine, 2-carboxypiperidine, 2-carboxamidopiperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamidohomopiperidine, homopiperazine, N-methylhomopiperazine and N-(2-hydroxyethyl)homopiperazine.

Preferably, the radicals $R''_3$ and $R''_4$ form, together with the nitrogen atom to which they are attached, a 5- or 7-membered ring chosen from pyrrolidine, 3-hydroxypyrrolidine, 3-aminopyrrolidine, 3-dimethylaminopyrrolidine, pyrrolidine-2-carboxylic acid, 3-hydroxypyrrolidine-2-carboxylic acid, piperidine, hydroxypiperidine, homopiperidine, diazepane, N-methylhomopiperazine and N-β-hydroxyethylhomopiperazine.

In accordance with an even more preferred embodiment of the invention, $R''_3$ and $R''_4$ form, together with the nitrogen atom to which they are attached, a 5-membered ring such as pyrrolidine, 3-hydroxypyrrolidine, 3-aminopyrrolidine or 3-dimethylaminopyrrolidine.

The compounds of formula (III) may be optionally salified with strong mineral acids, for instance HCl, HBr, HI, $H_2SO_4$ or $H_3PO_4$, or organic acids, for instance acetic acid, lactic acid, tartaric acid, citric acid, succinic acid, benzenesulfonic acid, para-toluenesulfonic acid, formic acid or methanesulfonic acid.

They may also be in the form of solvates, for example a hydrate or a solvate of a linear or branched alcohol such as ethanol or isopropanol.

As examples of derivatives of formula (III), mention may be made of the compounds presented below, or the addition salts thereof, solvates thereof or solvates of the salts thereof:

4,5-diamino-1,2-dimethyl-1,2-dihydropyrazol-3-one;
4-amino-5-methylamino-1,2-dimethyl-1,2-dihydropyrazol-3-one;
4-amino-5-dimethylamino-1,2-dimethyl-1,2-dihydropyrazol-3-one;
4-amino-5-(2-hydroxyethyl)amino-1,2-dimethyl-1,2-dihydropyrazol-3-one;
4-amino-5-(pyrrolidin-1-yl)-1,2-dimethyl-1,2-dihydropyrazol-3-one;
4-amino-5-(piperidin-1-yl)-1,2-dimethyl-1,2-dihydropyrazol-3-one;
4,5-diamino-1,2-bis(2-hydroxyethyl)-1,2-dihydropyrazol-3-one;
4-amino-5-methylamino-1,2-bis(2-hydroxyethyl)-1,2-dihydropyrazol-3-one;
4-amino-5-dimethylamino-1,2-bis(2-hydroxyethyl)-1,2-dihydropyrazol-3-one;
4-amino-5-(2-hydroxyethyl)amino-1,2-bis(2-hydroxyethyl)-1,2-dihydropyrazol-3-one;
4-amino-5-(pyrrolidin-1-yl)-1,2-bis(2-hydroxyethyl)-1,2-dihydropyrazol-3-one;
4-amino-5-(piperidin-1-yl)-1,2-bis(2-hydroxyethyl)-1,2-dihydropyrazol-3-one;
4,5-diamino-1,2-diethyl-1,2-dihydropyrazol-3-one;
4,5-diamino-1,2-phenyl-1,2-dihydropyrazol-3-one;
4,5-diamino-1-ethyl-2-methyl-1,2-dihydropyrazol-3-one;
4,5-diamino-2-ethyl-1-methyl-1,2-dihydropyrazol-3-one;
4,5-diamino-1-phenyl-2-methyl-1,2-dihydropyrazol-3-one;
4,5-diamino-2-phenyl-1-methyl-1,2-dihydropyrazol-3-one;
4,5-diamino-1-(2-hydroxyethyl)-2-methyl-1,2-dihydropyrazol-3-one;
4,5-diamino-2-(2-hydroxyethyl)-1-methyl-1,2-dihydropyrazol-3-one;
2,3-diamino-6,7-dihydro-1H,5H-pyrazolo[1,2-a]pyrazol-1-one;
2-amino-3-methylamino-6,7-dihydro-1H,5H-pyrazolo[1,2-a]pyrazol-1-one;
2-amino-3-dimethylamino-6,7-dihydro-1H,5H-pyrazolo[1,2-a]pyrazol-1-one;
2-amino-3-ethylamino-6,7-dihydro-1H,5H-pyrazolo[1,2-a]pyrazol-1-one;
2-amino-3-isopropylamino-6,7-dihydro-1H,5H-pyrazolo[1,2-a]pyrazol-1-one;
2-amino-3-(2-hydroxyethyl)amino-6,7-dihydro-1H,5H-pyrazolo[1,2-a]pyrazol-1-one;
2-amino-3-(2-hydroxypropyl)amino-6,7-dihydro-1H,5H-pyrazolo[1,2-a]pyrazol-1-one;
2-amino-3-bis(2-hydroxyethyl)amino-6,7-dihydro-1H,5H-pyrazolo[1,2-a]pyrazol-1-one;
2-amino-3-(pyrrolidin-1-yl)-6,7-dihydro-1H,5H-pyrazolo[1,2-a]pyrazol-1-one;
2-amino-3-(3-hydroxypyrrolidin-1-yl)-6,7-dihydro-1H,5H-pyrazolo[1,2-a]pyrazol-1-one;
2-amino-3-(piperidin-1-yl)-6,7-dihydro-1H,5H-pyrazolo[1,2-a]pyrazol-1-one;
2,3-diamino-6-hydroxy-6,7-dihydro-1H,5H-pyrazolo[1,2-a]pyrazol-1-one;
2,3-diamino-6-methyl-6,7-dihydro-1H,5H-pyrazolo[1,2-a]pyrazol-1-one;
2,3-diamino-6-dimethyl-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
2,3-diamino-5,8-dihydro-1H,6H-pyridazino[1,2-a]pyrazol-1-one;
4-amino-5-dimethylamino-1,2-diethyl-1,2-dihydropyrazol-3-one;
4-amino-1,2-diethyl-5-ethylamino-1,2-dihydropyrazol-3-one;
4-amino-1,2-diethyl-5-isopropylamino-1,2-dihydropyrazol-3-one;
4-amino-1,2-diethyl-5-(2-hydroxyethylamino)-1,2-dihydropyrazol-3-one;
4-amino-5-(2-dimethylaminoethylamino)-1,2-diethyl-1,2-dihydropyrazol-3-one;
4-amino-5-[bis(2-hydroxyethyl)amino]-1,2-diethyl-1,2-dihydropyrazol-3-one;
4-amino-1,2-diethyl-5-(3-imidazol-1-ylpropylamino)-1,2-dihydropyrazol-3-one;
4-amino-5-dimethylamino-1,2-diethyl-1,2-dihydropyrazol-3-one;
4-amino-1,2-diethyl-5-ethylamino-1,2-dihydropyrazol-3-one;
4-amino-1,2-diethyl-5-isopropylamino-1,2-dihydropyrazol-3-one;
4-amino-1,2-diethyl-5-(2-hydroxyethylamino)-1,2-dihydropyrazol-3-one;
4-amino-5-(2-dimethylaminoethylamino)-1,2-diethyl-1,2-dihydropyrazol-3-one;
4-amino-5-[bis(2-hydroxyethyl)amino]-1,2-diethyl-1,2-dihydropyrazol-3-one;
4-amino-1,2-diethyl-5-(3-imidazol-1-ylpropylamino)-1,2-dihydropyrazol-3-one;
4-amino-1,2-diethyl-5-(3-hydroxypyrrolidin-1-yl)-1,2-dihydropyrazol-3-one;
4-amino-1,2-diethyl-5-pyrrolidin-1-yl-1,2-dihydropyrazol-3-one;
4-amino-5-(3-dimethylaminopyrrolidin-1-yl)-1,2-diethyl-1,2-dihydropyrazol-3-one;
4-amino-1,2-diethyl-5-(4-methylpiperazin-1-yl)pyrazolidin-3-one;
2,3-diamino-6-hydroxy-6,7-dihydro-5H-pyrazolo[1,2-a]pyrazol-1-one;

some of which are featured below to illustrate the names via chemical structures:

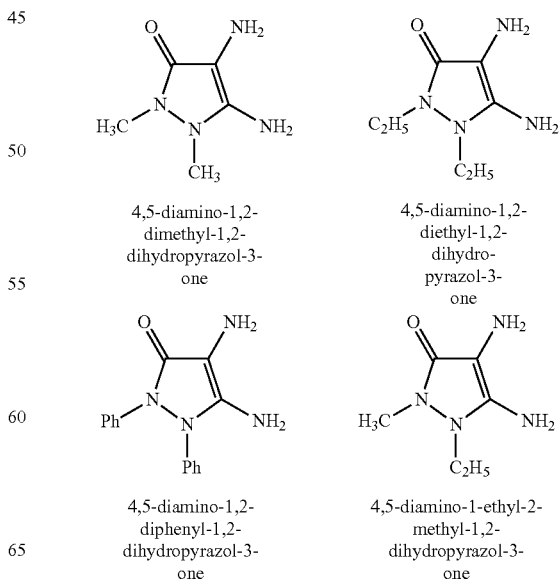

4,5-diamino-1,2-dimethyl-1,2-dihydropyrazol-3-one 4,5-diamino-1,2-diethyl-1,2-dihydropyrazol-3-one 4,5-diamino-1,2-diphenyl-1,2-dihydropyrazol-3-one 4,5-diamino-1-ethyl-2-methyl-1,2-dihydropyrazol-3-one

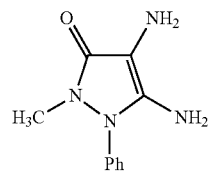

4,5-diamino-1-phenyl-2-methyl-1,2-dihydropyrazol-3-one

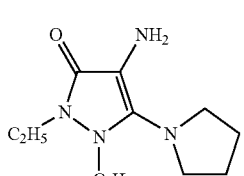

4-amino-5-(pyrrolidin-1-yl)-1,2-diethyl-1,2-dihydropyrazol-3-one

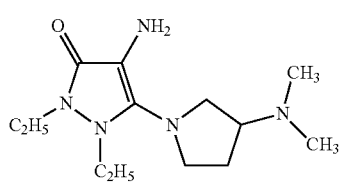

4-amino-5-(3-dimethylaminopyrrolidin-1-yl)-1,2-diethyl-1,2-dihydropyrazol-3-one

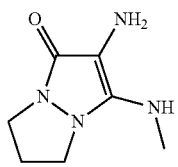

2,3-diamino-6,7-dihydro-1H,5H-pyrazolo[1,2-a]pyrazol-1-one

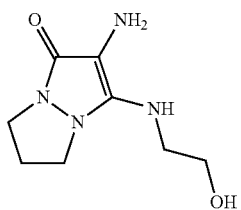

2-amino-3-methylamino-6,7-dihydro-1H,5H-pyrazolo[1,2-a]pyrazol-1-one 2-amino-3-ethylamino-6,7-dihydro-1H,5H-pyrazolo[1,2-a]pyrazol-1-one

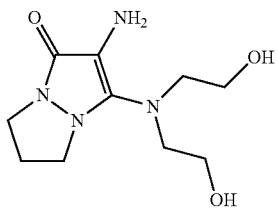

2-amino-3-(2-hydroxyethyl)amino-6,7-dihydro-1H,5H-pyrazolo[1,2-a]pyrazol-1-one 2-amino-3-(2-hydroxypropyl)amino-6,7-dihydro-1H,5H-pyrazolo[1,2-a]pyrazol-1-one 2-amino-3-bis(2-hydroxyethyl)amino-6,7-dihydro-1H,5H-pyrazolo[1,2-a]pyrazol-1-one 2-amino-3-isopropylamino-6,7-dihydro-1H,5H-pyrazolo[1,2-a]pyrazol-1-one

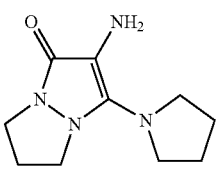

2-amino-3-(pyrrolidin-1-yl)-6,7-dihydro-1H,5H-pyrazolo[1,2-a]pyrazol-1-one 2-amino-3-(3-hydroxypyrrolidin-1-yl)-6,7-dihydro-1H,5H-pyrazolo[1,2-a]pyrazol-1-one

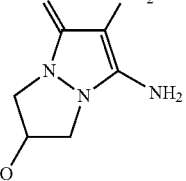

2,3-diamino-6-hydroxy-6,7-dihydro-1H,5H-pyrazolo[1,2-a]pyrazol-1-one 2,3-diamino-6-methyl-6,7-dihydro-1H,5H-pyrazolo[1,2-a]pyrazol-1-one

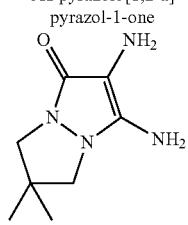

2,3-diamino-6,6-dimethyl-6,7-dihydro-1H,5H-pyrazolo[1,2-a]pyrazol-1-one 2,3-diamino-5,6,7,8-tetrahydro-1H,6H-pyridazino[1,2-a]pyrazol-1-one

2,3-diamino-5,8-dihydro-1H,6H-pyridazino[1,2-a]pyrazol-1-one

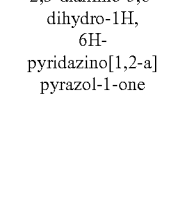

4,5-diamino-1-(2-hydroxyethyl)-2-methyl-1,2-dihydropyrazol-3-one

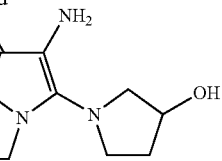

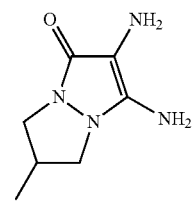

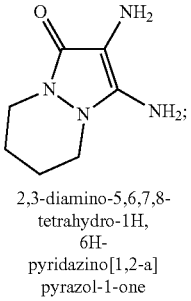

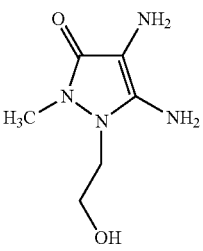

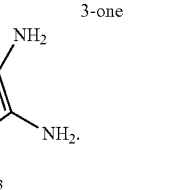

4,5-diamino-2-(2-hydroxyethyl)-1-methyl-1,2-dihydropyrazol-3-one

Among these compounds, the diamino-N,N-dihydropyrazolone derivatives of formula (III) or the addition salts thereof, solvates thereof and solvates of the salts thereof that are particularly preferred are the following compounds:

2,3-diamino-6,7-dihydro-1H,5H-pyrazolo[1,2-a]pyrazol-1-one;
2-amino-3-ethylamino-6,7-dihydro-1H,5H-pyrazolo[1,2-a]pyrazol-1-one;
2-amino-3-isopropylamino-6,7-dihydro-1H,5H-pyrazolo[1,2-a]pyrazol-1-one;
2-amino-3-(pyrrolidin-1-yl)-6,7-dihydro-1H,5H-pyrazolo[1,2-a]pyrazol-1-one;
4,5-diamino-1,2-dimethyl-1,2-dihydropyrazol-3-one;
4,5-diamino-1,2-diethyl-1,2-dihydropyrazol-3-one;
4,5-diamino-1,2-bis(2-hydroxyethyl)-1,2-dihydropyrazol-3-one;
2-amino-3-(2-hydroxyethyl)amino-6,7-dihydro-1H,5H-pyrazolo[1,2-a]pyrazol-1-one;
2-amino-3-dimethylamino-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
4-amino-1,2-diethyl-5-(pyrrolidin-1-yl)-1,2-dihydropyrazol-3-one;
4-amino-5-(3-dimethylaminopyrrolidin-1-yl)-1,2-diethyl-1,2-dihydropyrazol-3-one;
2,3-diamino-6-hydroxy-6,7-dihydro-1H,5H-pyrazolo[1,2-a]pyrazol-1-one.

According to one particular embodiment, the composition of the invention contains an oxidation base chosen from:
4,5-diamino-1,2-diethyl-1,2-dihydropyrazol-3-one;
4-amino-1,2-diethyl-5-(pyrrolidin-1-yl)-1,2-dihydropyrazol-3-one;
4-amino-5-(3-dimethylaminopyrrolidin-1-yl)-1,2-diethyl-1,2-dihydropyrazol-3-one;
2,3-diamino-6-hydroxy-6,7-dihydro-1H,5H-pyrazolo[1,2-a]pyrazol-1-one;
2,3-diamino-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one; and the addition salts thereof, solvates thereof or solvates of the salts thereof.

In the context of the invention, the term "cationic radical present in the compound of formula (IV)" means any linear or branched or cyclic, saturated or unsaturated radical, comprising a quaternary ammonium, this quaternary ammonium being of the type —$N^+RaRbRc$, Ra, Rb and Rc, which may be identical or different, representing a $C_1$-$C_6$ alkyl radical which may be substituted with a hydroxyl. Ra and Rb may together form a 5- to 8-membered heterocycle, in which case the radical Rc is a $C_1$-$C_6$ alkyl radical which may be substituted with a hydroxyl.

As examples of radicals of the type —$N^+RaRbRc$, mention may be made of trimethylammonium, triethylammonium, dimethylethyl ammonium, diethylmethylammonium, diisopropylmethylammonium, diethylpropylammonium, hydroxyethyldiethylammonium, di-β-hydroxyethylmethylammonium, tri-β-hydroxyethylammonium, piperidinium, N-methylpiperidinium, pyrrolidinium, N-methylpyrrolidinium, morpholinium, N-methylmorpholinium, imidazolium, hydroxyethylimidazolium, methylimidazolium, piperazinium and methylpiperazinium radicals.

For the purposes of the present patent application, a "cationic heterocycle" means a 5- to 8-membered heterocycle in which at least one of the ring members is a quaternary ammonium.

Examples of cationic heterocyclic radicals that may be mentioned include imidazolium, pyridinium, piperidinium, piperazinium, pyrrolidinium, morpholinium, pyrimidinium, thiazolium, benzimidazolium, benzothiazolium, oxazolium, benzotriazolium, pyrazolium, triazolium and benzoxazolium radicals.

Preferably, $Z'''_1$ represents a group $NR'''_2$ with $R'''_2$ chosen from a hydrogen atom and a $C_1$-$C_2$ alkyl radical, and more preferentially $NR'''_2$ is chosen from NH and NMe.

Preferably, $R'''_1$ is a $C_1$-$C_8$ alkyl radical substituted or interrupted with a cationic radical, which may or may not be interrupted with one or more oxygen atoms and/or one or more groups $NR'''_2$, optionally substituted with a hydroxyl radical.

Preferably, the cationic radicals are chosen from trimethylammonium, triethylammonium, dimethylethylammonium, diethylmethylammonium, diisopropylmethylammonium, hydroxyethyldiethylammonium, imidazolium, pyridinium, piperidinium, piperazinium, pyrrolidinium, morpholinium, pyrimidinium, thiazolium and benzimidazolium radicals.

Even more preferably, the cationic radicals are chosen from trimethylammonium, imidazolium, piperazinium, piperidinium, morpholinium and pyrrolidinium radicals.

According to a first particularly preferred variant of the invention, $Z'''_1$ is an oxygen atom or $NR'''_2$ with $R'''_2$ chosen from hydrogen and a linear or branched $C_1$-$C_4$ alkyl radical, preferably $R'''_2$ represents H or Me; and $R'''_1$ represents a saturated, linear $C_2$-$C_8$ alkyl radical, which is not interrupted or interrupted with an oxygen atom or with an NH group, optionally substituted with a hydroxyl radical, and substituted or interrupted with a cationic radical chosen from trimethylammonium, imidazolium, piperazinium, piperidinium, pyrrolidinium and morpholinium radicals.

According to a second preferred variant of the invention, $Z'''_1$ is a group $NR'''_2$ and $R'''_1$ and $R'''_2$ form, together with the nitrogen atom to which they are attached, a saturated or unsaturated 5- to 8-membered cationic heterocycle, optionally substituted with one or more radicals chosen from $C_1$-$C_{10}$ alkyl and $C_1$-$C_{10}$ hydroxyalkyl radicals. This heterocycle may contain one or more heteroatoms chosen from N and O, preferably N. According to this variant, $Z'''_1$ is a group $NR'''_2$ and $R'''_1$ and $R'''_2$ form, together with the nitrogen atom to which they are attached, a piperidinium, imidazolium, pyrrolidinium, morpholinium or piperazinium radical substituted with one or more radicals chosen from $C_1$-$C_4$ hydroxyalkyl and $C_1$-$C_4$ alkyl radicals.

According to the third variant, $Z'''_1$ is a group $NR'''_2$ and $R'''_1$ and $R'''_2$ form, together with the nitrogen atom to which they are attached, a saturated or unsaturated, 5- to 8-membered non-cationic heterocycle, substituted with a cationic radical preferably chosen from trimethylammonium, diethylmethylammonium, imidazolium, piperazinium, piperidinium, pyrrolidinium and morpholinium radicals. According to this variant, the saturated or unsaturated, 5- to 8-membered non-cationic heterocycle is preferably chosen from pyrrolidinine, piperidine and morpholine, this ring being substituted with a cationic radical chosen from trimethylammonium, diethylmethylammonium, pyrrolidinium, piperidinium and imidazolium radicals.

Preferably, $R'''_3$ is chosen from a hydrogen atom and $C_1$-$C_4$ alkyl radicals. Even more preferably, $R'''_3$ is a hydrogen atom.

The cationic aminopyridines of formula (IV) may be in free form or in the form of salts, such as addition salts with a mineral acid, preferably chosen from hydrochlorides, hydrobromides, sulfates and phosphates, or with an organic acid, for instance citrates, succinates, tartrates, lactates, tosylates, benzenesulfonates, acetates, para-toluenesulfonates, formates and methanesulfonates.

The cationic aminopyridines of formula (IV) may also be in the form of solvates, for example a hydrate or a solvate of a linear or branched alcohol such as ethanol or isopropanol.

The electrical neutrality of the compounds of formula (IV) is ensured by an organic or mineral, cosmetically acceptable anion or mixture of anions, noted An-.

An- represents an anion or a mixture of anions chosen, for example, from a halide such as chloride, bromide, fluoride or iodide; a hydroxide; a sulfate; a hydrogen sulfate; an alkyl sulfate in which the linear or branched alkyl part is $C_1$-$C_6$, such as the methyl sulfate or ethyl sulfate ion; carbonates and hydrogen carbonates; salts of carboxylic acids, such as formate, acetate, citrate, tartrate and oxalate; alkylsulfonates for which the linear or branched alkyl part is $C_1$-$C_6$, such as the methylsulfonate ion; arylsulfonates for which the aryl part, preferably phenyl, is optionally substituted with one or more $C_1$-$C_4$ alkyl radicals, for instance 4-tolylsulfonate; and alkylsulfonates such as mesylate.

Preferably the cationic aminopyridines of formula (IV) are chosen from the following compounds:

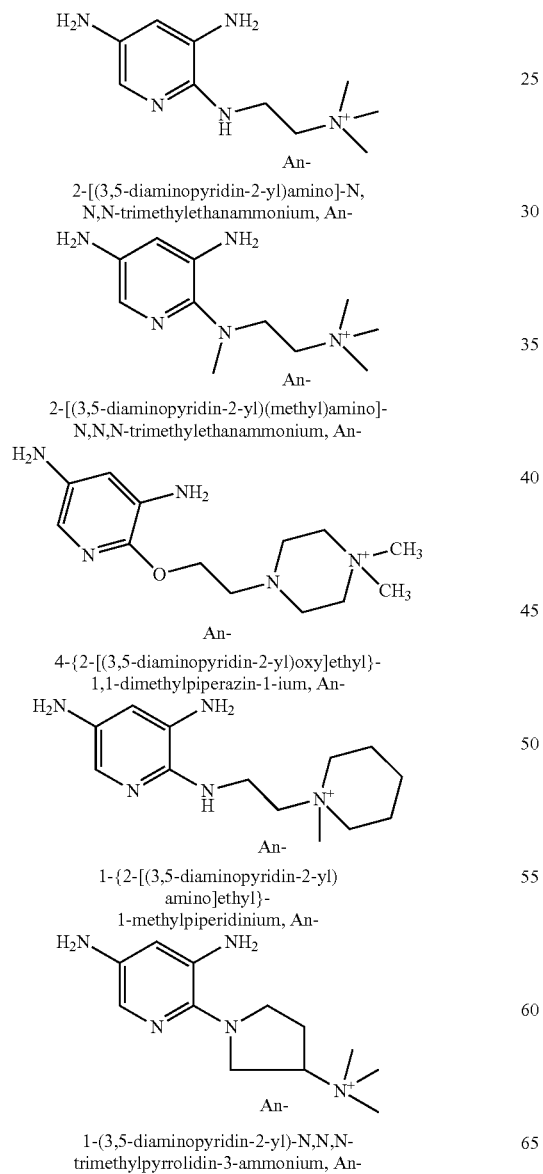
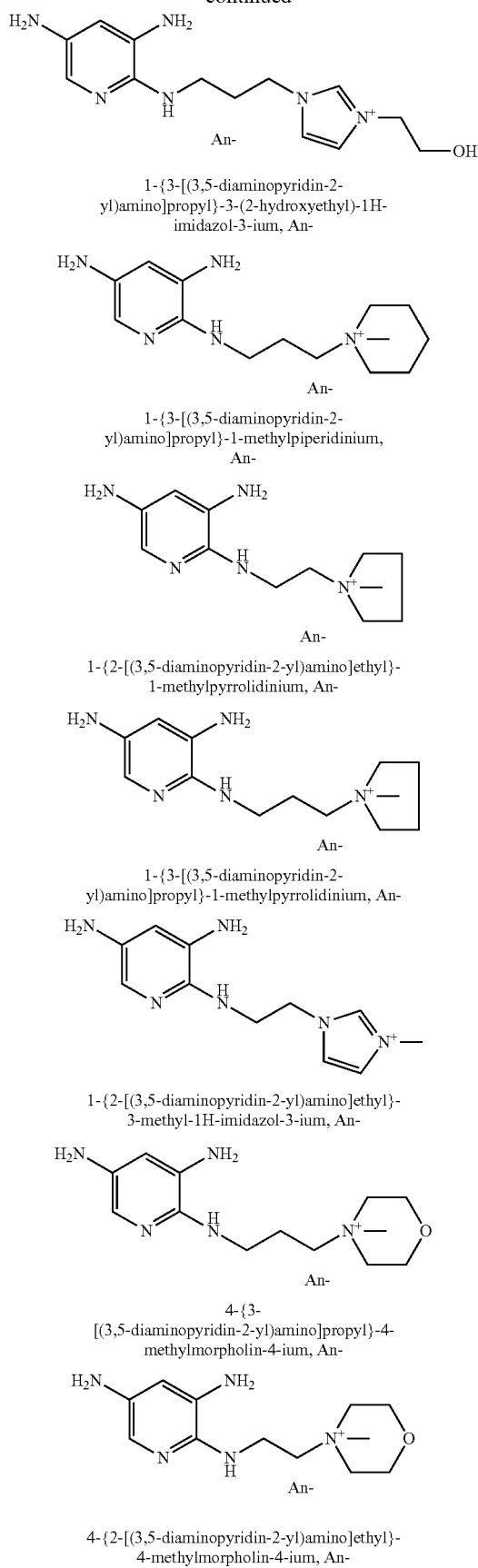

-continued

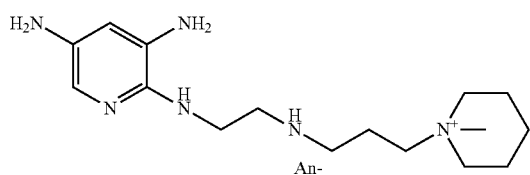

1-[2-({2-[(3,5-diaminopyridin-2-yl)amino]ethyl}amino)ethyl]-1-methylpiperidinium, An-

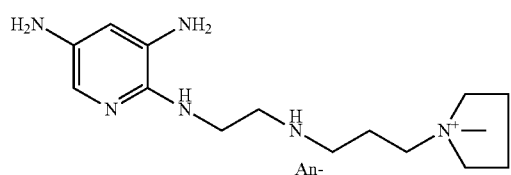

1-[2-({2-[(3,5-diaminopyridin-2-yl)amino]ethyl}amino)ethyl]-1-methylpyrrolidinium, An-

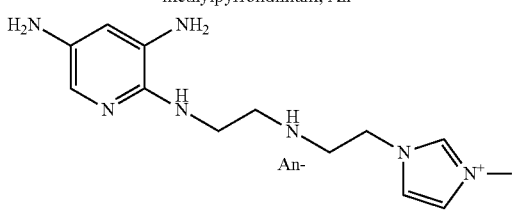

1-[2-({2-[(3,5-diaminopyridin-2-yl)amino]ethyl}amino)ethyl]-3-methyl-1H-imidazol-3-ium, An-

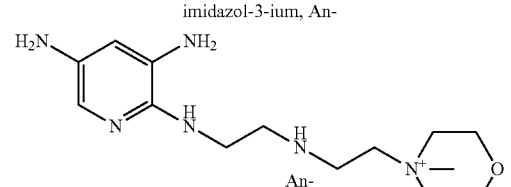

4-[2-({2-[(3,5-diaminopyridin-2-yl)amino]ethyl}amino)ethyl]-4-methylmorpholin-4-ium, An-

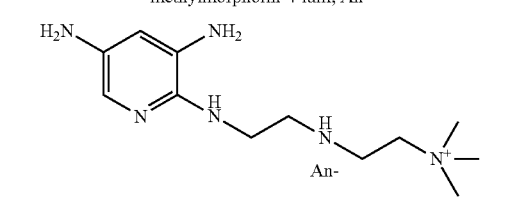

2-({2-[(3,5-diaminopyridin-2-yl)amino]ethyl}amino)-N,N,N-trimethylethanammonium, An-

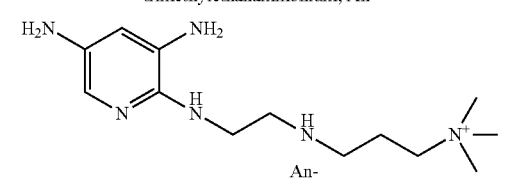

3-({2-[(3,5-diaminopyridin-2-yl)amino]ethyl}amino)-N,N,N-trimethylpropan-1-ammonium, An- -continued

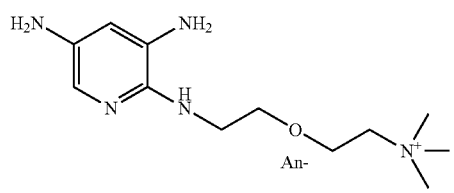

2-{2-[(3,5-diaminopyridin-2-yl)amino]ethoxy}-N,N,N-trimethylethanammonium, An-

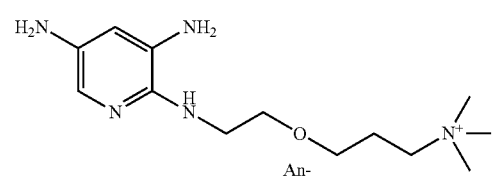

3-{2-[(3,5-diaminopyridin-2-yl)amino]ethoxy}-N,N,N-trimethylpropan-1-ammonium, An-

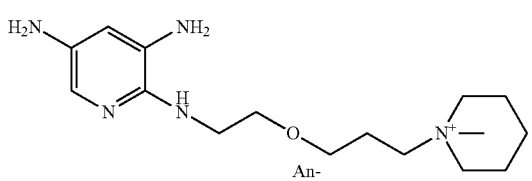

1-(2-{2-[(3,5-diaminopyridin-2-yl)amino]ethyoxy}ethyl)-1-methylpiperidinium, An-

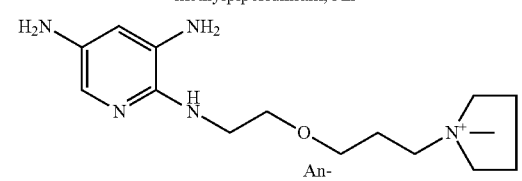

1-(2-{2-[(3,5-diaminopyridin-2-yl)amino]ethoxy}ethyl)-1-methylpyrrolidinium, An-

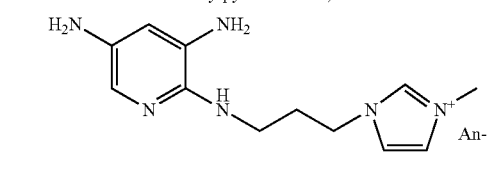

1-{3-[(3,5-diaminopyridin-2-yl)amino]propyl}-3-methyl-1H-imidazol-3-ium, An-

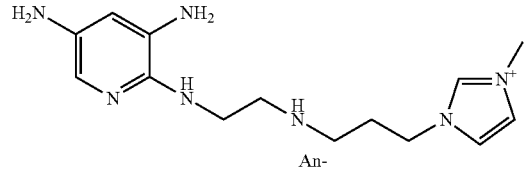

1-[3-({2-[(3,5-diaminopyridin-2-yl)amino]ethyl}amino)propyl]-3-methyl-1H-imidazol-3-ium, An- -continued

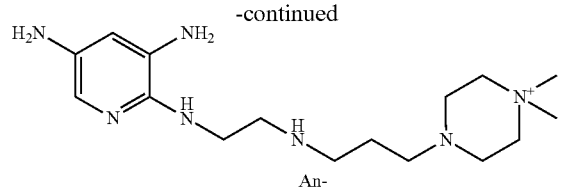

4-[3-({2-[(3,5-diaminopyridin-2-yl)amino]ethyl}amino)propyl]-1,1-dimethylpiperazin-1-ium, An-

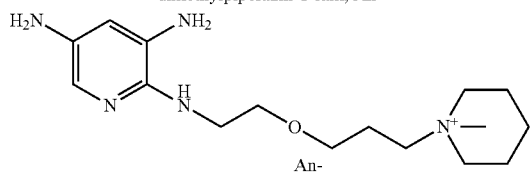

1-(3-{2-[(3,5-diaminopyridin-2-yl)amino]ethoxy}propyl)-1-methylpiperidinium, An-

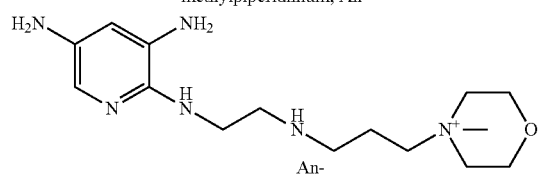

4-[(3-({2-[(3,5-diaminopyridin-2-yl)amino]ethyl}amino)propyl]-4-methylmorpholin-4-ium, An-

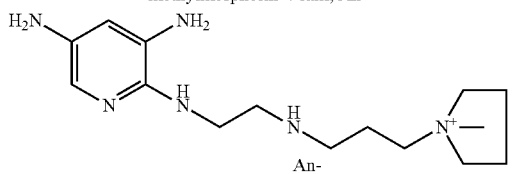

1-[3({2-[(3,5-diaminopyridin-2-yl)amino]ethyl}amino)propyl]-1-methylpyrrolidinium, An-

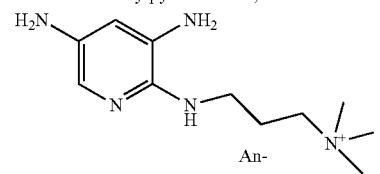

3-[(3,5-diaminopyridin-2-yl)amino]-N,N,N-trimethylpropan-1-ammonium, An-

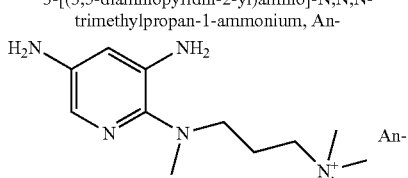

3-[(3,5-diaminopyridin-2-yl)(methyl)amino]-N,N,N-trimethylpropan-1-ammonium, An-

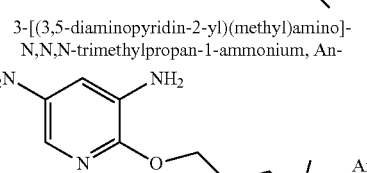

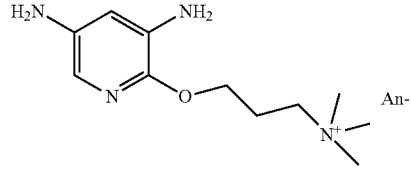

3-[(3,5-diaminopyridin-2-yl)oxy-N,N,N-trimethylpropan-1-ammonium, An-

-continued

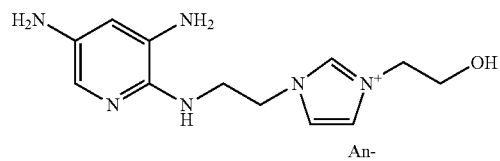

1-{2-[(3,5-diaminopyridin-2-yl)amino]ethyl}-3-(2-hydroxyethyl)-1H-imidazol-3-ium, An-

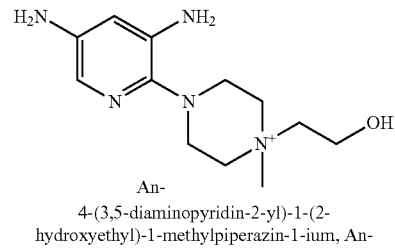

4-(3,5-diaminopyridin-2-yl)-1-(2-hydroxyethyl)-1-methylpiperazin-1-ium, An-

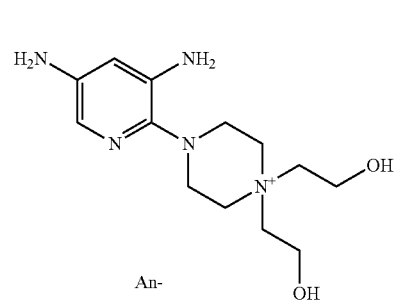

4-(3,5-diaminopyridin-2-yl)-1,1-bis(2-hydroxyethyl)piperazin-1-ium, An-

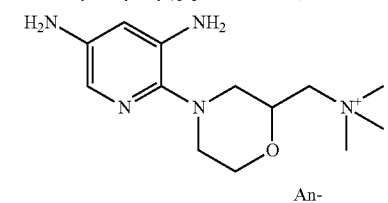

4-(3,5-diaminopyridin-2-yl)(2-trimethylethane)morpholinammonium, An-

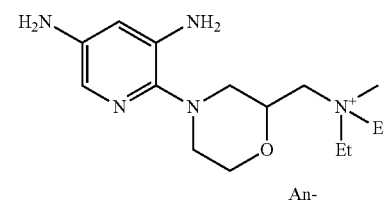

4-(3,5-diaminopyridin-2-yl)(2-methyldiethylethane)morpholinammonium, An-

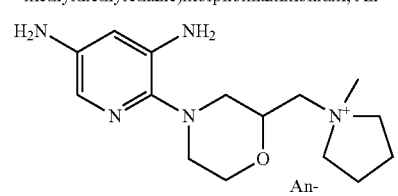

4-(3,5-diaminopyridin-2-yl)morpholine}2-1,1 dimethylpyrrolidinium, An-

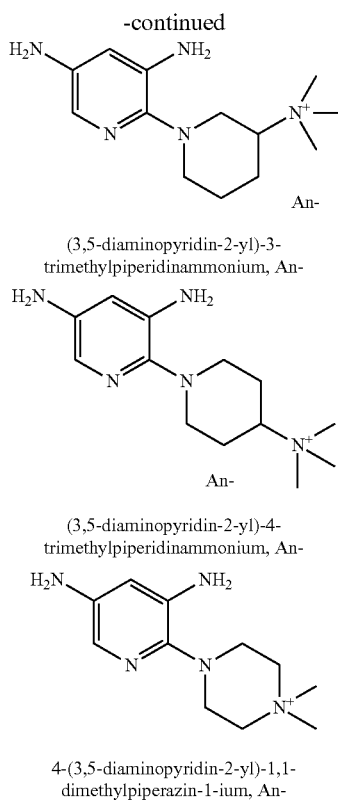

(3,5-diaminopyridin-2-yl)-3-trimethylpiperidinammonium, An- (3,5-diaminopyridin-2-yl)-4-trimethylpiperidinammonium, An- 4-(3,5-diaminopyridin-2-yl)-1,1-dimethylpiperazin-1-ium, An- An- having the same meaning as previously.

According to one particular embodiment of the invention, in formula (V), $R''''_1$ represents a hydrogen atom or a saturated $C_1$-$C_4$ alkyl radical optionally substituted with a hydroxyl radical.

According to another particular embodiment, $R''''_2$ and $R''''_3$, which may be identical or different, represent a hydrogen atom; a $C_1$-$C_4$ alkyl radical optionally substituted with one or more hydroxyl radicals; a carboxyl radical; a $C_1$-$C_4$ alkyl carboxylate radical; a radical $CONR''''_7R''''_8$, preferably $CONH_2$. Preferably, $R''''_2$ and $R''''_3$, which may be identical or different, represent a hydrogen atom; a $C_1$-$C_4$ alkyl radical optionally substituted with one or more hydroxyl radicals.

According to another particular embodiment, $R''''_4$ and $R''''_5$ are identical and represent a hydrogen atom.

According to another particular embodiment, $R''''_6$ represents a linear or branched $C_1$-$C_6$ alkyl radical; a carboxyl radical; a $C_1$-$C_6$ alkyl carboxylate; a carboxamide radical; a $(C_1$-$C_6)$alkoxy$(C_1$-$C_6)$alkyloxy radical; a $C_1$-$C_6$ alkoxy or hydroxy$(C_1$-$C_6)$alkyloxy radical; a radical O-Ak-$NR''''_9R''''_{10}$ with Ak=linear $C_1$-$C_6$ or branched $C_3$-$C_6$ divalent alkylene radical optionally interrupted with a radical $NR''''_7$. Preferably, $R''''_6$ represents a linear or branched $C_1$-$C_6$ alkyl radical; a $(C_1$-$C_6)$alkoxy$(C_1$-$C_6)$alkyloxy radical; a $C_1$-$C_6$ alkoxy or hydroxy$(C_1$-$C_6)$alkyloxy radical; a radical O-Ak-$NR''''_9R''''_{10}$ with Ak=linear $C_1$-$C_6$ or branched $C_3$-$C_6$ divalent alkylene radical optionally interrupted with a radical $NR''''_7$.

According to one particular embodiment, the compounds in accordance with the invention are chosen from the 4-aminoindole derivatives of formula (V'), and also the addition salts thereof, solvates thereof or solvates of the salts thereof:

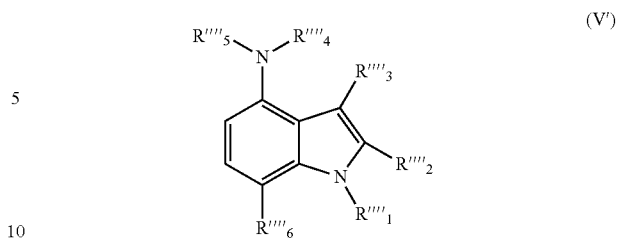

(V')

in which:

$R''''_1$ represents:
- a hydrogen atom;
- a saturated $C_1$-$C_4$ alkyl radical optionally substituted with a hydroxyl radical;

$R''''_2$ and $R''''_3$, which may be identical or different, represent:
- a hydrogen atom;
- a $C_1$-$C_4$ alkyl radical optionally substituted with one or more hydroxyl radicals;
- a carboxyl radical;
- a $C_1$-$C_4$ alkyl carboxylate radical;
- a radical $CONR''''_7R''''_8$, preferably a carboxamide radical $CONH_2$;

$R''''_4$ and $R''''_5$ represent a hydrogen atom;

$R''''_6$ represents:
- a linear or branched $C_1$-$C_6$ alkyl radical;
- a carboxyl radical;
- a $C_1$-$C_6$ alkyl carboxylate;
- a carboxamide radical;
- a $(C_1$-$C_6)$alkoxy$(C_1$-$C_6)$alkyloxy radical;
- a $C_1$-$C_6$ alkoxy radical or a $C_1$-$C_6$ hydroxyalkoxy radical;
- a radical O-Ak-$NR''''_9R''''_{10}$ with Ak=linear $C_1$-$C_6$ or branched $C_3$-$C_6$ divalent alkylene radical, optionally interrupted with one or more oxygen atoms and/or groups $NR''''_7$;

$R''''_7$ and $R''''_8$ represent a hydrogen atom or a $C_1$-$C_6$ alkyl radical optionally substituted with a hydroxyl radical;

$R''''_9$ and $R''''_{10}$, which may be identical or different, represent a saturated linear $C_1$-$C_4$ alkyl radical or an unsaturated linear $C_2$-$C_4$ alkyl radical;

$R''''_9$ and $R''''_{10}$ may form, with the nitrogen that bears them, a saturated or unsaturated 5- to 8-membered heterocycle, one of the chain members possibly being an oxygen atom or a radical $NR''''_{11}$ with $R''''_{11}$=H or $C_1$-$C_4$ alkyl, optionally substituted with OH.

The derivatives of formula (V) may be optionally salified with strong mineral acids, for instance HCl, HBr, HI, $H_2SO_4$ or $H_3PO_4$, or organic acids, for instance acetic acid, lactic acid, tartaric acid, citric acid, succinic acid, benzenesulfonic acid, para-toluenesulfonic acid, formic acid or methanesulfonic acid.

The derivatives of formula (V) may also be in the form of solvates, for example a hydrate or a solvate of a linear or branched alcohol such as ethanol or isopropanol.

As examples of derivatives of formula (V), mention may be made of the compounds presented below:

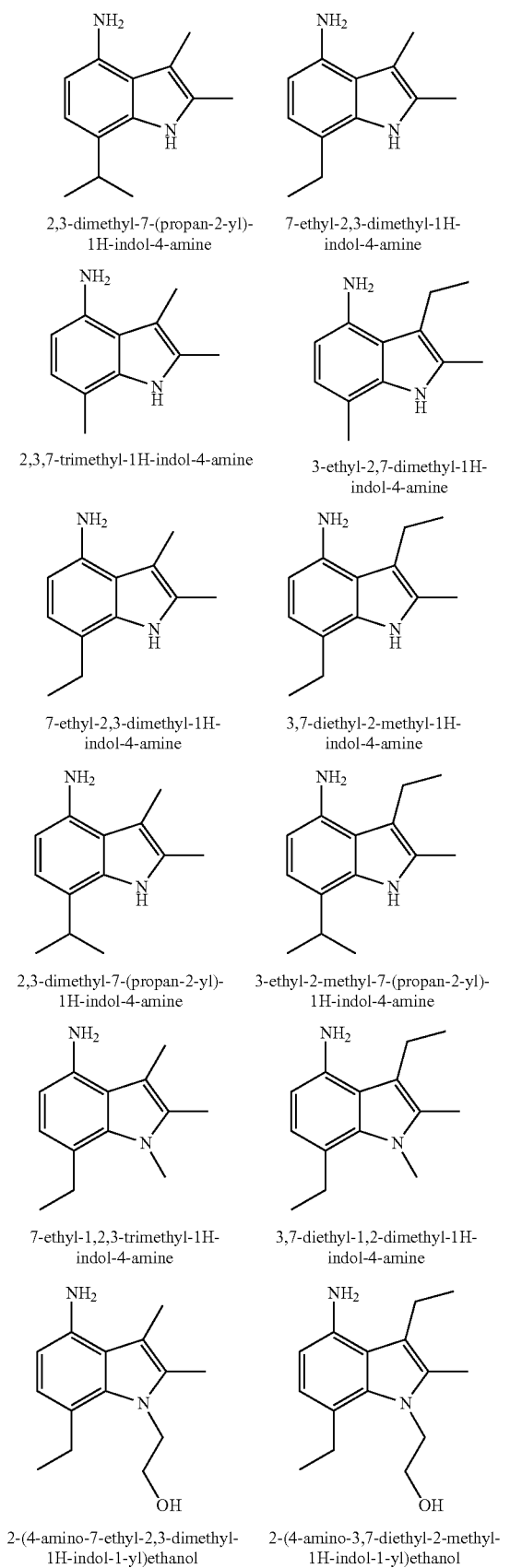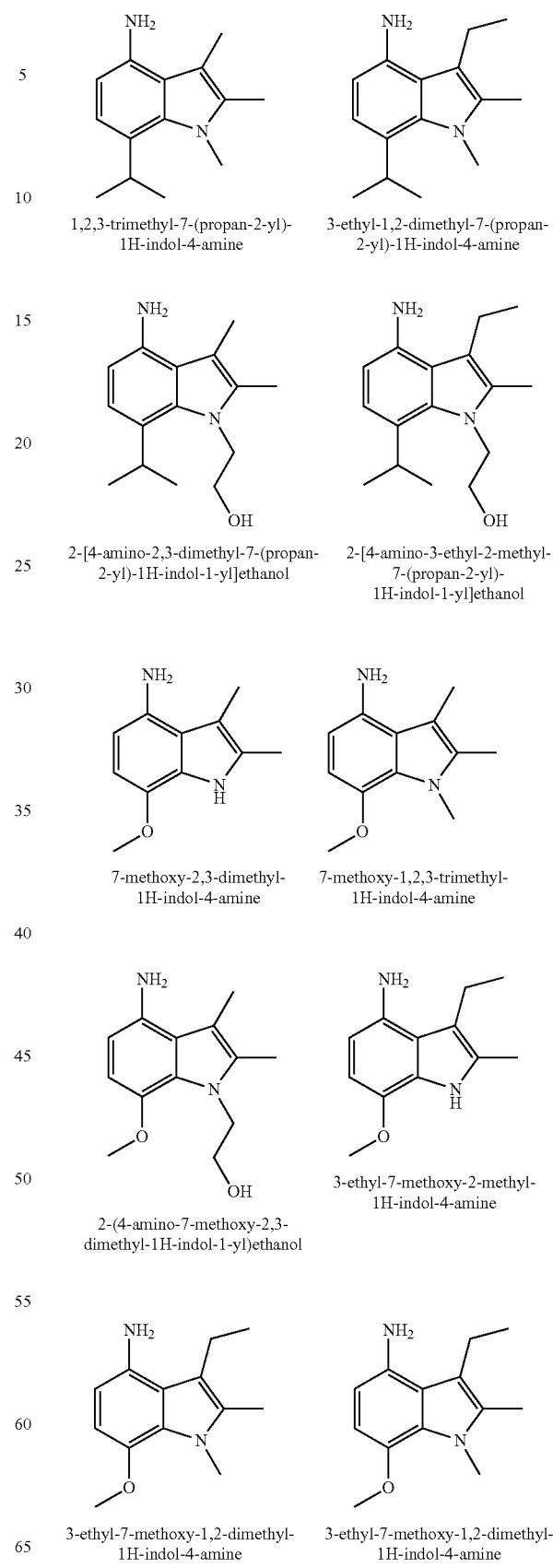

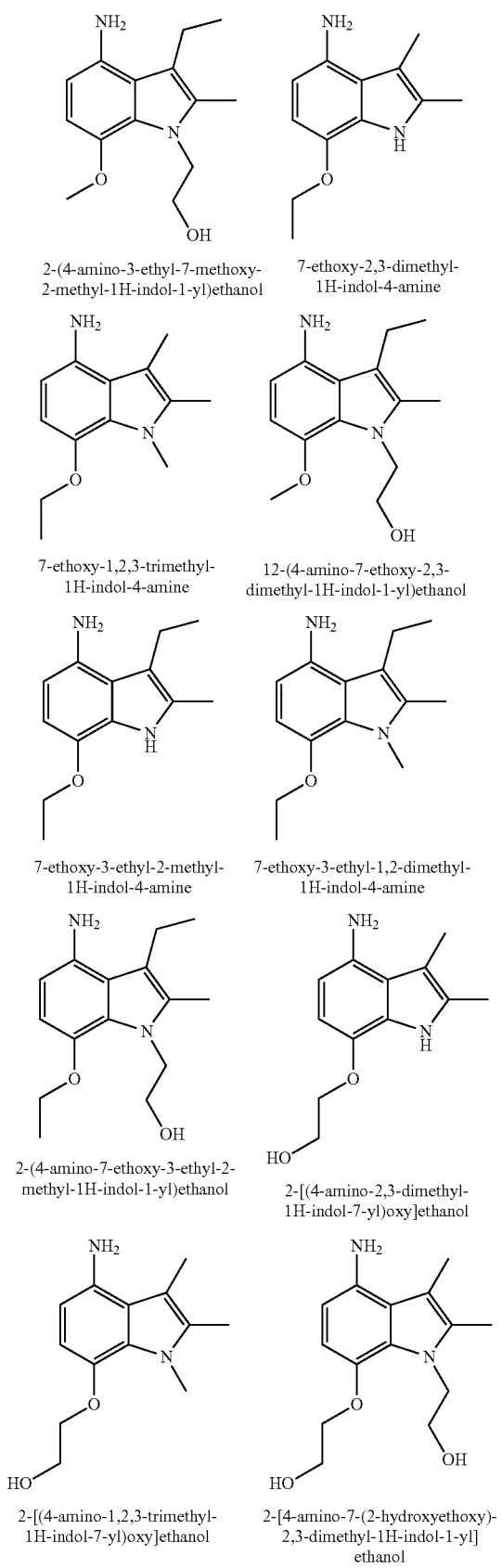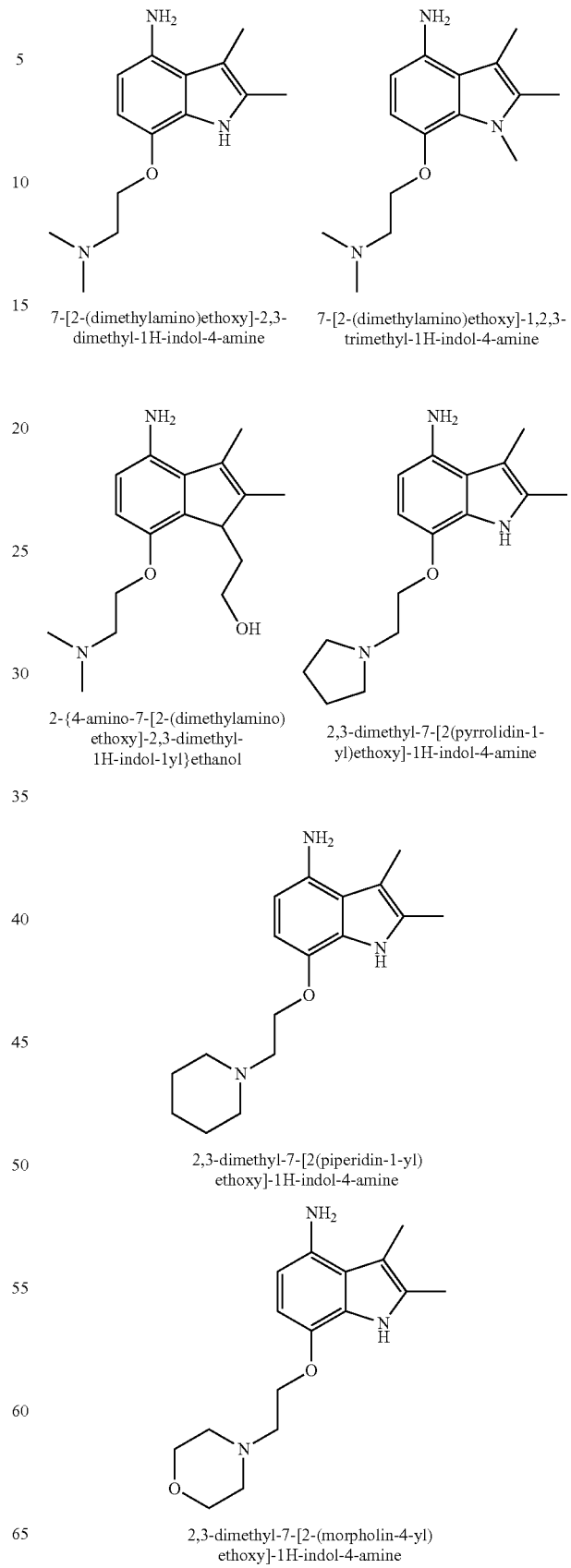

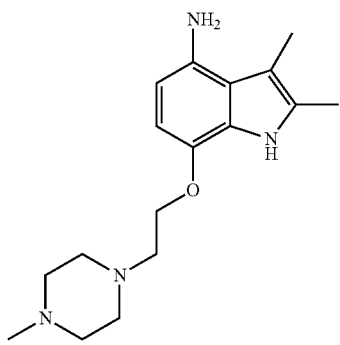

2,3-dimethyl-7-[2-(4-methylpiperazin-1-yl)
ethoxy]-1H-indol-4-amine

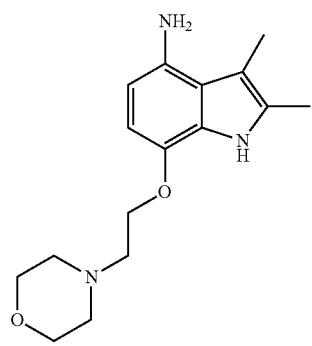

2,3-dimethyl-7-[2-(morpholin-4-yl)
ethoxy]-1H-indol-4-amine

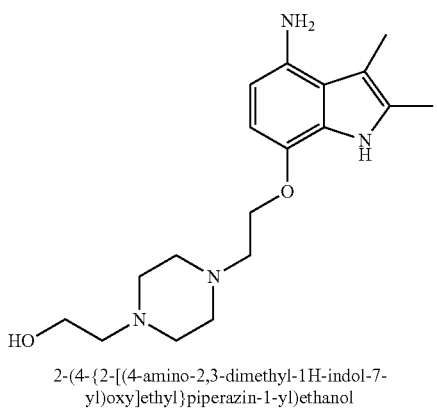

2-(4-{2-[(4-amino-2,3-dimethyl-1H-indol-7-
yl)oxy]ethyl}piperazin-1-yl)ethanol

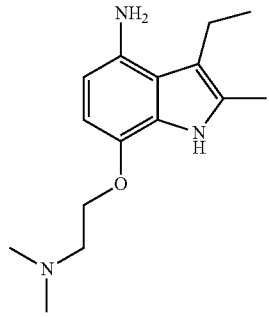

7-[2-(dimethylamino)ethoxy]-3-ethyl-2-
methyl-1H-indol-4-amine

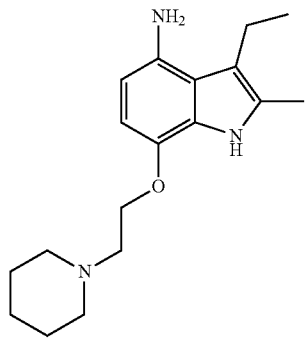

3-ethyl-2-methyl-7-[2-(piperidin-1-yl)
ethoxy]-1H-indol-4-amine

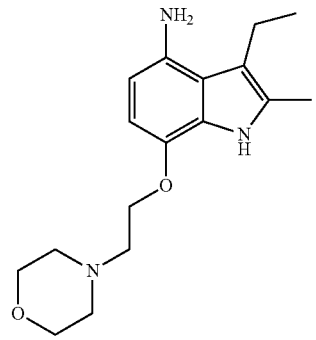

3-ethyl-2-methyl-7-[2-(morpholin-4-yl)
ethoxy]-1H-indol-4-amine

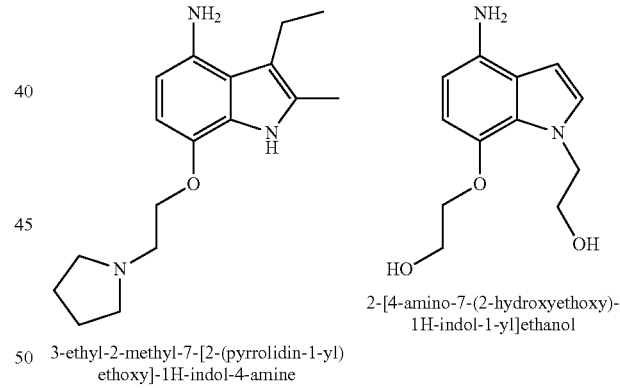

3-ethyl-2-methyl-7-[2-(pyrrolidin-1-yl)
ethoxy]-1H-indol-4-amine

2-[4-amino-7-(2-hydroxyethoxy)-
1H-indol-1-yl]ethanol

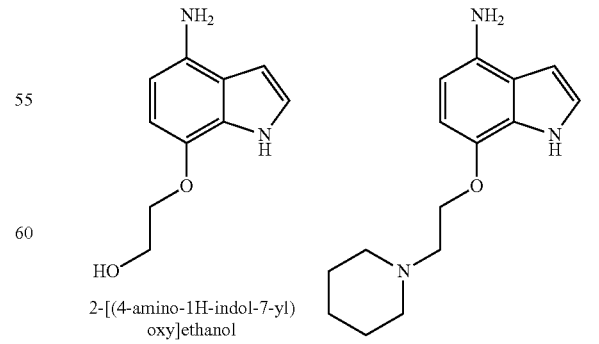

2-[(4-amino-1H-indol-7-yl)
oxy]ethanol

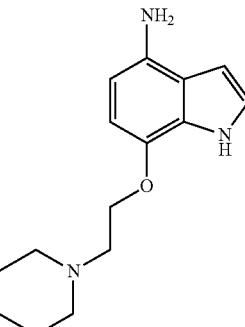

7-[2-(piperidin-1-yl)ethoxy]-
1H-indol-4-amine

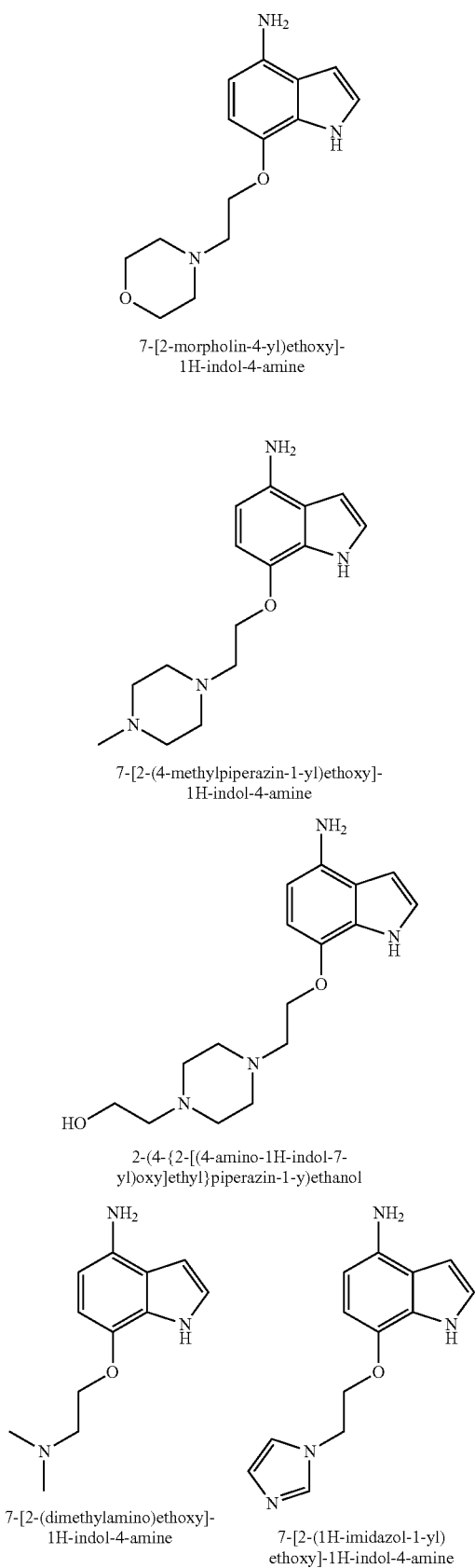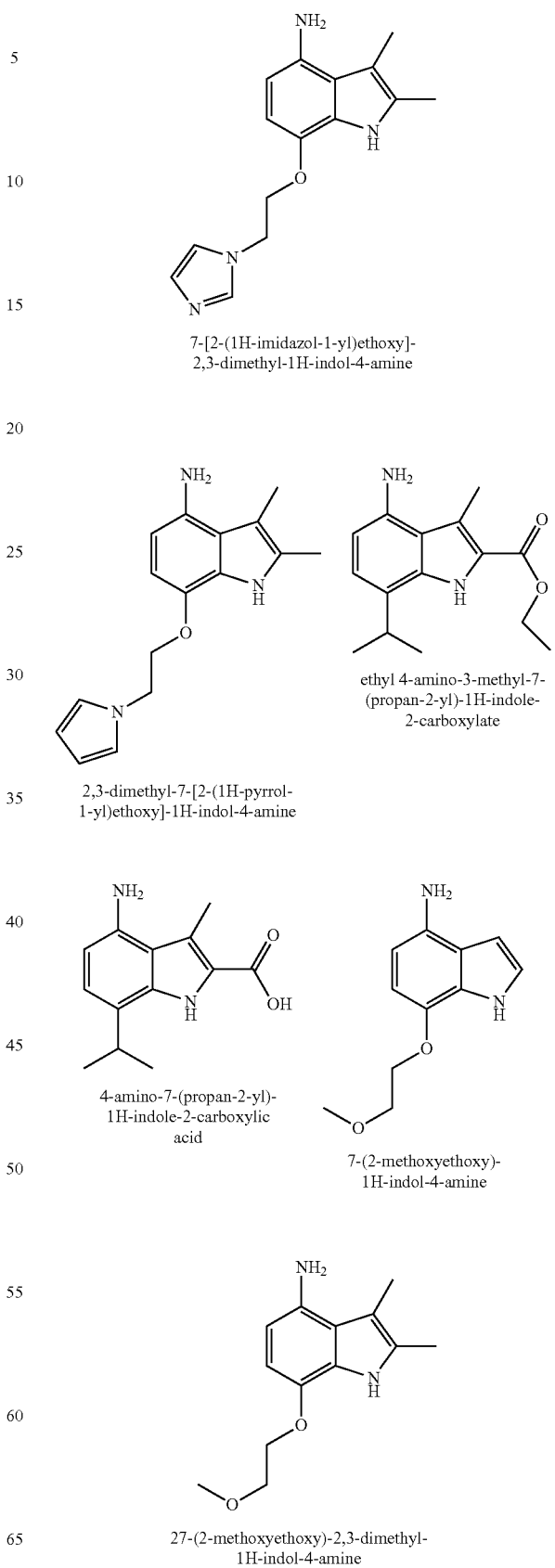

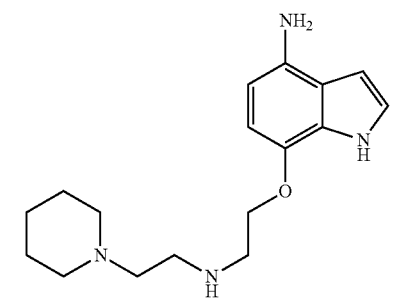

7-(2-{[2-(piperidin-1-yl)ethyl]amino}
ethoxy)-1H-idol-4-amine

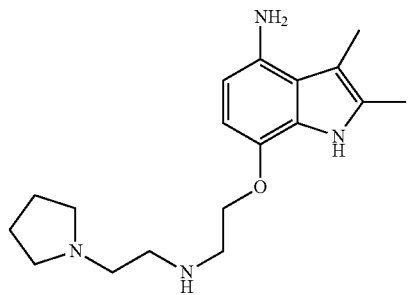

2,3-dimethyl-7-(2-{[2-(pyrrolidin-1-yl)
ethyl]amino}ethoxy)-1H-indol-4-amine

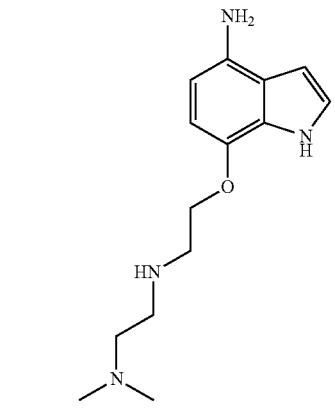

N'-{2-[(4-amino-1H-indol-7-yl)oxy]ethyl}-
N,N-dimethylethane-1,2-diamine

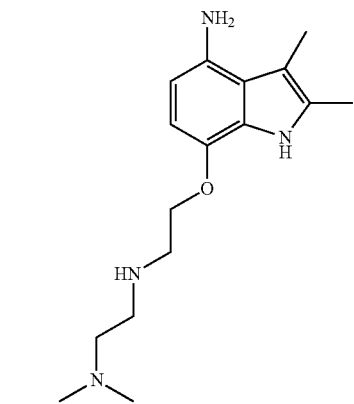

N'-{2-[(4-amino-2,3-dimethyl-1H-indol-7-
yl)oxy]ethyl}-N,N-dimethylethane-
1,2-diamine

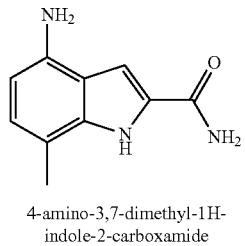

4-amino-3,7-dimethyl-1H-
indole-2-carboxamide

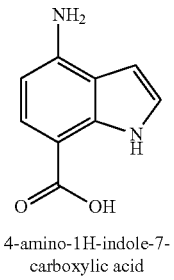

4-amino-1H-indole-7-
carboxylic acid

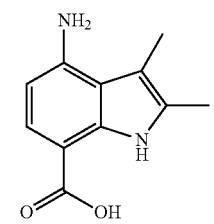

4-amino-2,3-dimethyl-1H-indole-7-
carboxylic acid

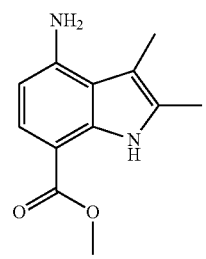

methyl 4-amino-2,3-dimethyl-
1H-indole-7-carboxylate

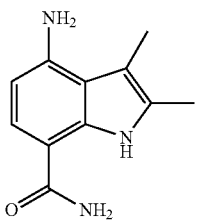

4-amino-2,3-dimethyl-1H-indole-7-
carboxamide

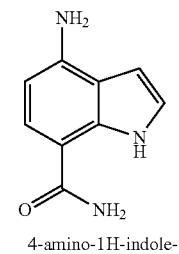

4-amino-1H-indole-7-
carboxamide

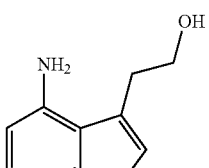

2-(4-amino-7-methyl-1H-
indol-3-yl)ethanol

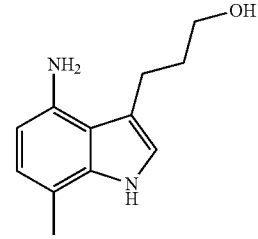

3-(4-amino-7-methyl-1H-
indol-3-yl)propan-1-ol

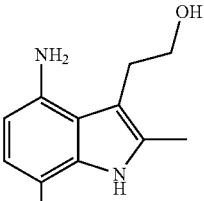

2-(4-amino-2,7-dimethyl-1H-
indol-3-yl)ethanol

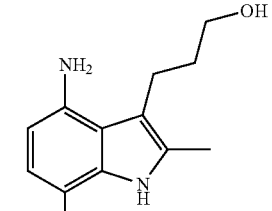

3-(4-amino-2,7-dimethyl-1H-
indol-3-yl)propan-1-ol

-continued

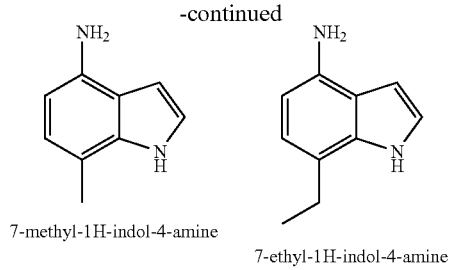

7-methyl-1H-indol-4-amine 7-ethyl-1H-indol-4-amine

Among these compounds, the derivatives of formula (V) that are particularly preferred are the following:

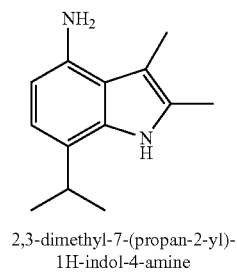

2,3-dimethyl-7-(propan-2-yl)-1H-indol-4-amine

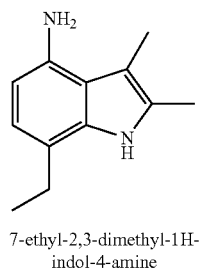

7-ethyl-2,3-dimethyl-1H-indol-4-amine

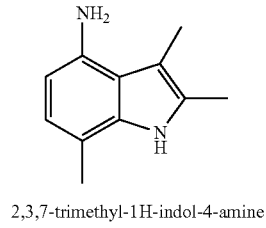

2,3,7-trimethyl-1H-indol-4-amine 3-ethyl-2,7-dimethyl-1H-indol-4-amine

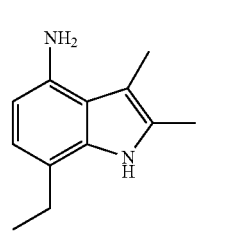

7-ethyl-2,3-dimethyl-1H-indol-4-amine 3,7-diethyl-2-methyl-1H-indol-4-amine

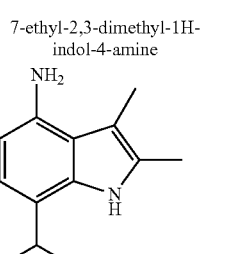
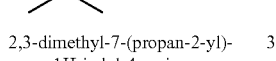

2,3-dimethyl-7-(propan-2-yl)-1H-indol-4-amine 3-ethyl-2-methyl-7-(propan-2-yl)-1H-indol-4-amine

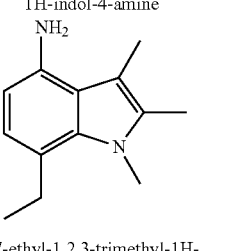
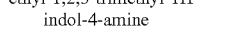

7-ethyl-1,2,3-trimethyl-1H-indol-4-amine 3,7-diethyl-1,2-dimethyl-1H-indol-4-amine -continued

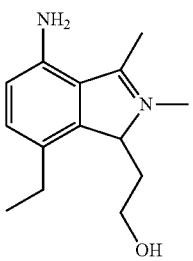

2-(4-amino-7-ethyl-2,3-dimethyl-1H-indol-1-yl)ethanol

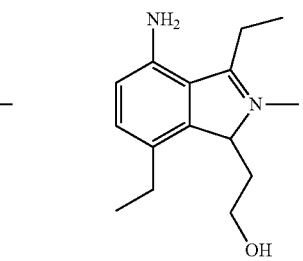

2-(4-amino-3,7-diethyl-2-methyl-1H-indol-1-yl)ethanol

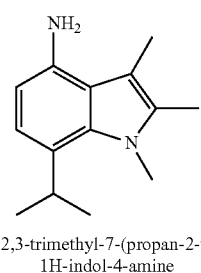
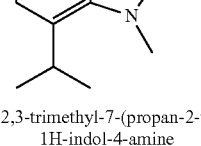

1,2,3-trimethyl-7-(propan-2-yl)-1H-indol-4-amine

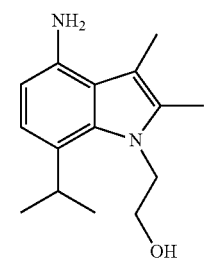
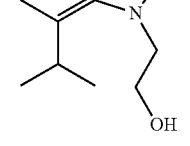

2-[4-amino-2,3-dimethyl-7-(propan-2-yl)-1H-indol-1-yl] ethanol

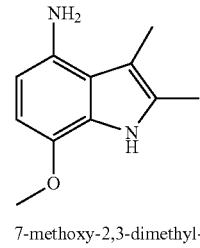

7-methoxy-2,3-dimethyl-1H-indol-4-amine

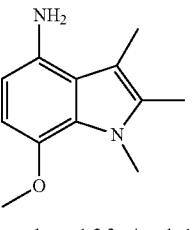

7-methoxy-1,2,3-trimethyl-1H-indol-4-amine

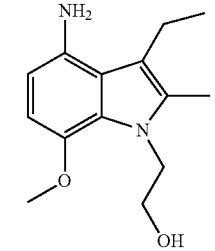
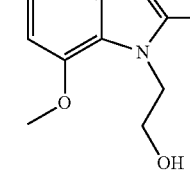

2-(4-amino-3-ethyl-7-methoxy-2-methyl-1H-indol-1-yl)ethanol

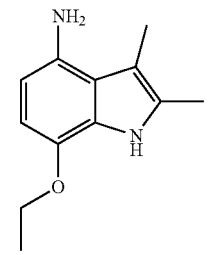
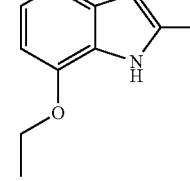

7-ethoxy-2,3-dimethyl-1H-indol-4-amine

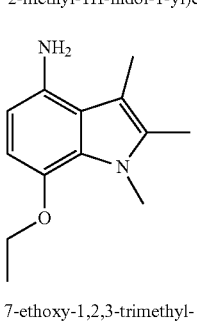

7-ethoxy-1,2,3-trimethyl-1H-indol-4-amine

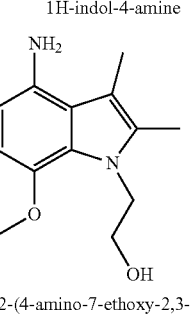

12-(4-amino-7-ethoxy-2,3-dimethyl-1H-indol-1-yl)ethanol

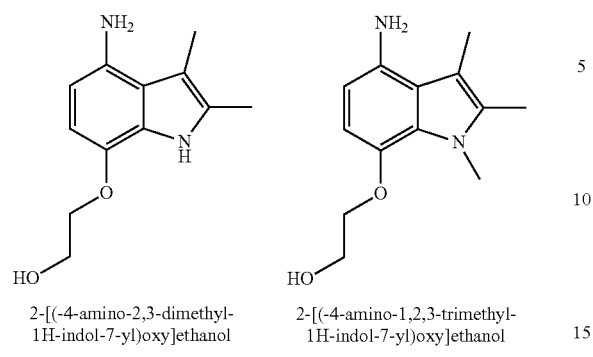

2-[(-4-amino-2,3-dimethyl-1H-indol-7-yl)oxy]ethanol

2-[(-4-amino-1,2,3-trimethyl-1H-indol-7-yl)oxy]ethanol

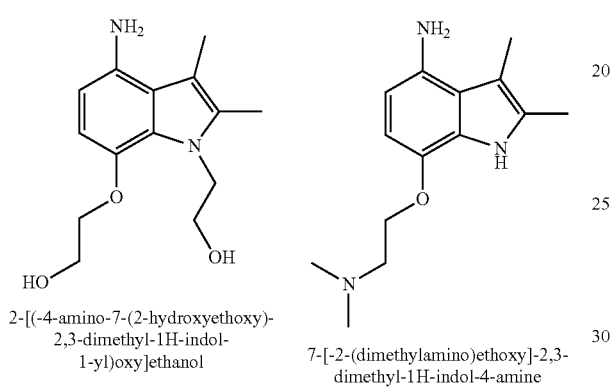

2-[(-4-amino-7-(2-hydroxyethoxy)-2,3-dimethyl-1H-indol-1-yl)oxy]ethanol

7-[-2-(dimethylamino)ethoxy]-2,3-dimethyl-1H-indol-4-amine

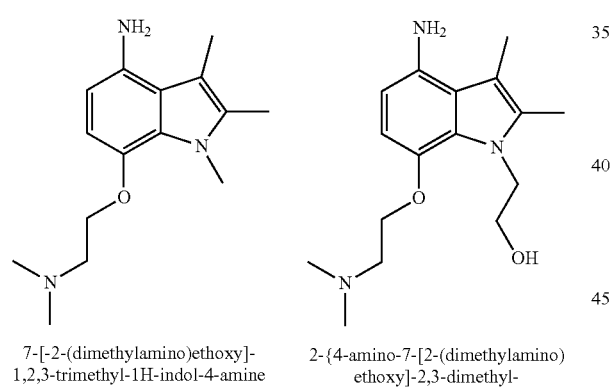

7-[-2-(dimethylamino)ethoxy]-1,2,3-trimethyl-1H-indol-4-amine

2-{4-amino-7-[2-(dimethylamino)ethoxy]-2,3-dimethyl-1H-indol-1-yl}ethanol

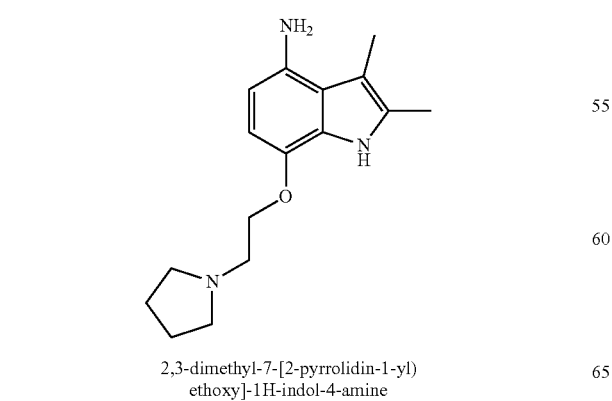

2,3-dimethyl-7-[2-pyrrolidin-1-yl)ethoxy]-1H-indol-4-amine

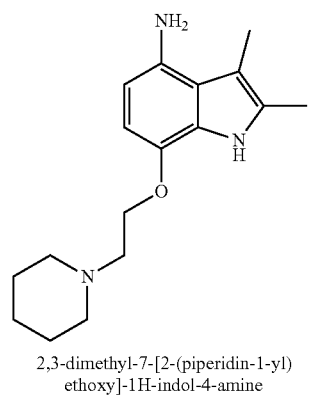

2,3-dimethyl-7-[2-(piperidin-1-yl)ethoxy]-1H-indol-4-amine

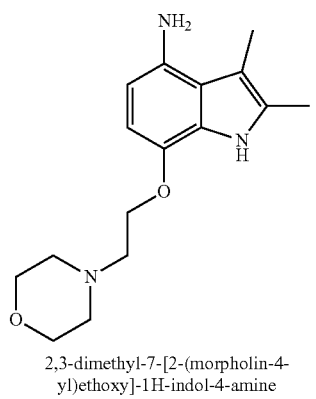

2,3-dimethyl-7-[2-(morpholin-4-yl)ethoxy]-1H-indol-4-amine

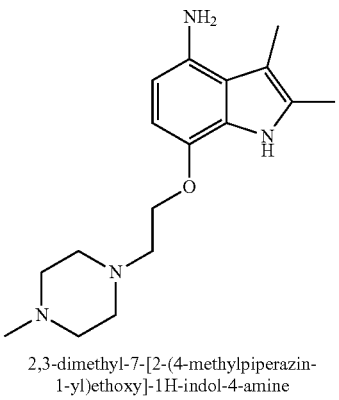

2,3-dimethyl-7-[2-(4-methylpiperazin-1-yl)ethoxy]-1H-indol-4-amine

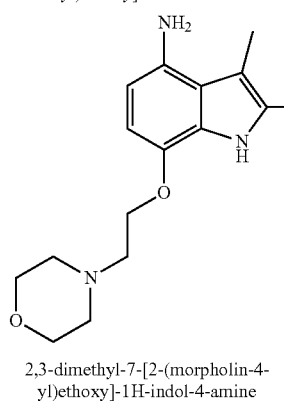

2,3-dimethyl-7-[2-(morpholin-4-yl)ethoxy]-1H-indol-4-amine

-continued

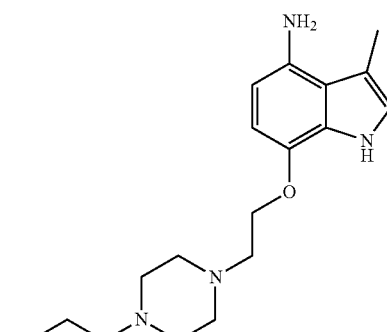

2-(4-{2-[(4-amino-2,3-dimethyl-1H-indol-7-yl)oxy]ethyl}piperazin-1-yl)ethanol

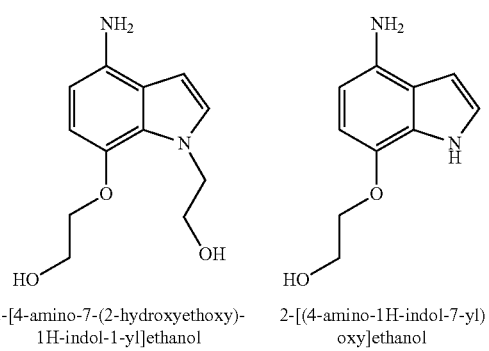

2-[4-amino-7-(2-hydroxyethoxy)-1H-indol-1-yl]ethanol

2-[(4-amino-1H-indol-7-yl)oxy]ethanol

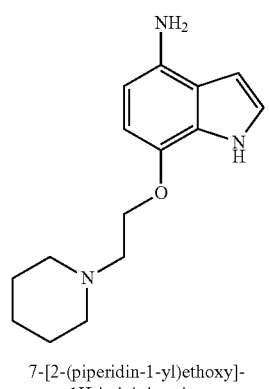

7-[2-(piperidin-1-yl)ethoxy]-1H-indol-4-amine

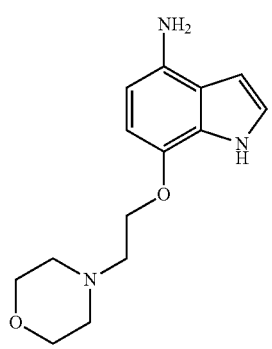

7-[2-(morpholin-4-yl)ethoxy]-1H-indol-4-amine

-continued

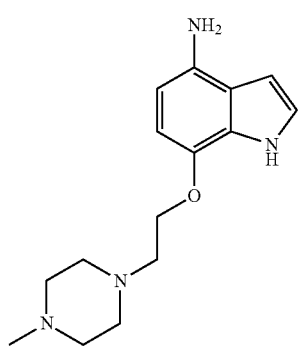

7-[2-(methylpiperazin-1-yl)ethoxy]-1H-indol-4-amine

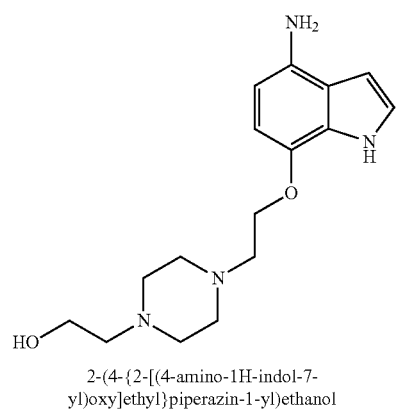

2-(4-{2-[(4-amino-1H-indol-7-yl)oxy]ethyl}piperazin-1-yl)ethanol

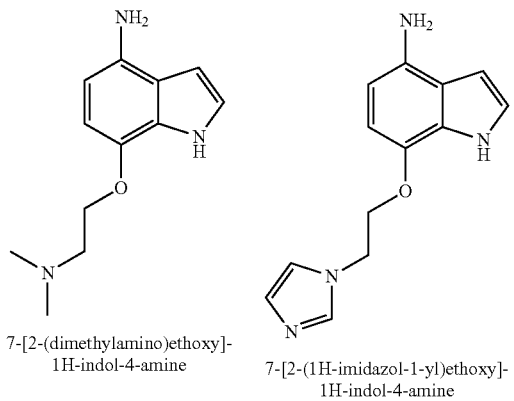

7-[2-(dimethylamino)ethoxy]-1H-indol-4-amine

7-[2-(1H-imidazol-1-yl)ethoxy]-1H-indol-4-amine

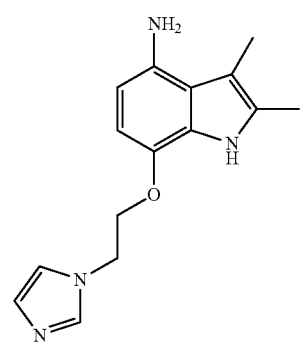

7-[2-(1H-imidazol-1-yl)ethoxy]-2,3-dimethyl-1H-indol-4-amine

-continued

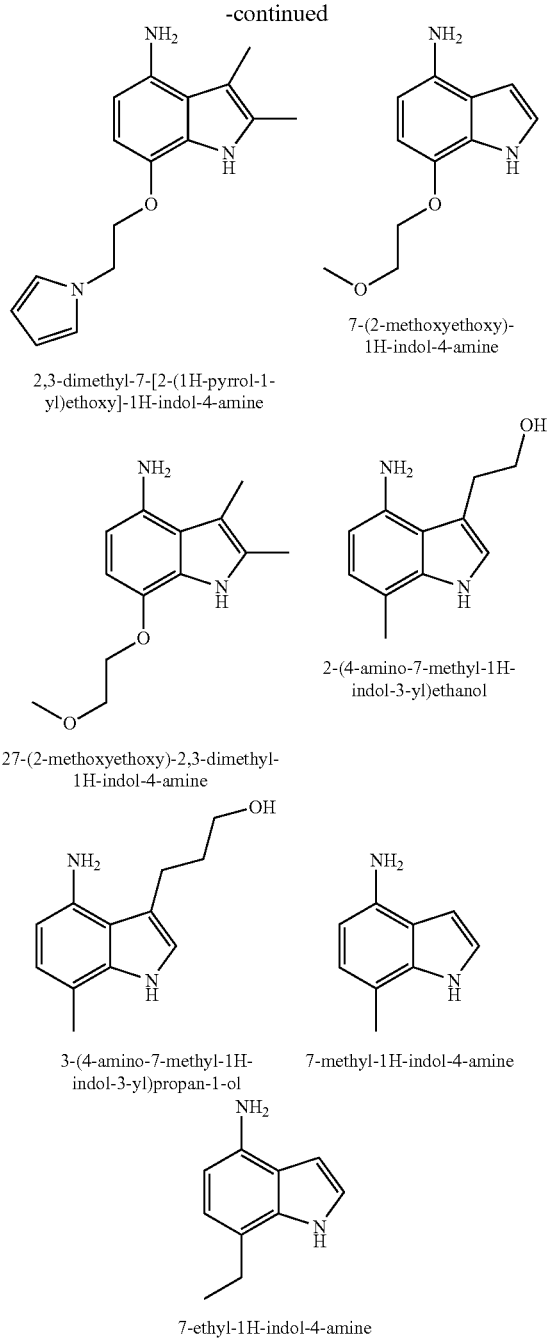

2,3-dimethyl-7-[2-(1H-pyrrol-1-yl)ethoxy]-1H-indol-4-amine 7-(2-methoxyethoxy)-1H-indol-4-amine 27-(2-methoxyethoxy)-2,3-dimethyl-1H-indol-4-amine 2-(4-amino-7-methyl-1H-indol-3-yl)ethanol 3-(4-amino-7-methyl-1H-indol-3-yl)propan-1-ol 7-methyl-1H-indol-4-amine 7-ethyl-1H-indol-4-amine In general, the addition salts of the couplers of formulae (VI) to (IX) that may be used in the context of the invention are especially chosen from addition salts with an acid, such as hydrochlorides, hydrobromides, sulfates, citrates, succinates, tartrates, lactates, tosylates, benzenesulfonates, phosphates and acetates, and the addition salts with a base such as sodium hydroxide, potassium hydroxide, ammonia, amines or alkanolamines.

The compounds of formulae (I) to (IX), and the optional addition salts thereof, optional solvates thereof or optional solvates of the salts thereof are in general each present in an amount of between 0.001% and 10% by weight approximately and preferably between 0.005% and 6% by weight relative to the total weight of the dye composition.

The dye composition of the invention may optionally comprise at least one additional oxidation bases conventionally used for the dyeing of keratin fibres, other than the compounds of formulae (I), (II) and (III).

By way of example, these additional oxidation bases are chosen from para-phenylenediamines, bis(phenyl)alkylenediamines, para-aminophenols, bis-para-aminophenols, ortho-aminophenols, heterocyclic bases other than the bases of formulae (I), (II) and (III), and the addition salts thereof, solvates thereof and solvates of the salts thereof.

Among the para-phenylenediamines, examples that may be mentioned include para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid, solvates thereof or solvates of the salts thereof.

Among the para-phenylenediamines mentioned above, para-phenylenediamine, para-toluenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid, solvates thereof or solvates of the salts thereof are particularly preferred.

Among the bis(phenyl)alkylenediamines, examples that may be mentioned include N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the addition salts thereof with an acid, solvates thereof or solvates of the salts thereof.

Among the para-aminophenols, examples that may be mentioned include para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol, 4-amino-2-fluorophenol, 1-hydroxy-4-methylaminobenzene and 2,2'-methylenebis(4-aminophenol), and the addition salts thereof with an acid, solvates thereof or solvates of the salts thereof.

Among the ortho-aminophenols, examples that may be mentioned include 2-aminophenol, 2-amino-5-methylphenol, 2-amino-6-methylphenol and 5-acetamido-2-aminophenol, and the addition salts thereof with an acid, solvates thereof or solvates of the salts thereof.

Among the heterocyclic bases, examples that may be mentioned include pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the addition salts thereof with an acid, solvates thereof or solvates of the salts thereof.

Among the pyrimidine derivatives that may be mentioned are the compounds described, for example, in patents DE 2 359 399; JP 88-169 571; JP 05-63124; EP 0 770 375 or patent application WO 96/15765, for instance 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, pyrazolopyrimidine derivatives such as those mentioned in patent application FR-A-2 750 048, and among which mention may be made of pyrazolo[1,5-a]pyrimidine-3,7-diamine, 2,5-dimethylpyrazolo[1,5-a]pyrimidine-3,7-diamine, pyrazolo[1,5-a]pyrimidine-3,5-diamine, 2,7-dimethylpyrazolo[1,5-a]pyrimidine-3,5-diamine, 3-aminopyrazolo[1,5-a]pyrimidin-7-ol, 3-aminopyrazolo[1,5-a]pyrimidin-5-ol, 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,-N7,N7-tetramethylpyrazolo[1,5-a]pyrimidine-3,7-diamine and 3-amino-5-methyl-7-imidazolylpropylaminopyrazolo[1,5-a]pyrimidine, and the addition salts thereof with an acid, solvates thereof or solvates of the salts thereof.

Examples of diaminopyrazole bases that may be mentioned include the compounds described in patents DE-A-38 43 892 and DE-A-41 33 957 and patent applications WO 94/08969, WO 94/08970, FR-A-2 733 749 and DE-A-195 43 988, for instance 4,5-diamino-1-methylpyrazole, 4,5-diamino-1-(2-hydroxyethyl)pyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole and 4-amino-5-(2'-aminoethyl)amino-1,3-dimethylpyrazole, the addition salts thereof, solvates thereof or solvates of the salts thereof.

The additional oxidation base(s) are each generally present in an amount of between 0.001% and 10% by weight and preferably between 0.005% and 6% by weight relative to the total weight of the dye composition.

The dye composition according to the invention may contain at least one additional coupler conventionally used for the dyeing of keratin fibres other than the compounds of formulae (IV) to (IX). Among these couplers, mention may be made especially of meta-phenylenediamines, meta-aminophenols other than the compounds of formulae (VI) and (VIII), meta-diphenols, naphthalene-based couplers and heterocyclic couplers other than the compounds of formulae (IV), (V), (VII) and (IX), the addition salts thereof, solvates thereof or solvates of the salts thereof.

Examples of couplers that may be mentioned include 2-methyl-5-aminophenol, 2,4-dichloro-3-aminophenol, 5-amino-4-chloro-o-cresol, 4-chloro-1,3-dihydroxybenzene, 2,4-diamino-1-(3-hydroxyethyloxy)benzene, 2-amino-4-(β-hydroxyethylamino)-1-methoxybenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2 methyl-1-naphthol, 1,5-dihydroxynaphthalene, 2,7-naphthalenediol, 1-acetoxy-2-methylnaphthalene, 6-hydroxyindole, 4-hydroxyindole, 4-hydroxy-N-methylindole, 3,5-diamino-2,6-dimethoxypyridine, 2,6-dihydroxy-3,4-dimethylpyridine, 3-amino-2-methylamino-6-methoxypyridine, 1-N-(β-hydroxyethyl)amino-3,4-methylenedioxybenzene, 2,6-bis(β-hydroxyethylamino)toluene and 3-methyl-1-phenyl-5-pyrazolone, the addition salts thereof with an acid, solvates thereof or solvates of the salts thereof.

In general, the addition salts of the additional oxidation bases and additional couplers that may be used in the context of the invention are especially chosen from addition salts with an acid, such as hydrochlorides, hydrobromides, sulfates, citrates, succinates, tartrates, lactates, tosylates, benzenesulfonates, phosphates and acetates, and the addition salts with a base such as sodium hydroxide, potassium hydroxide, aqueous ammonia, amines or alkanolamines.

The additional coupler(s) are each generally present in an amount of between 0.001% and 10% by weight approximately and preferably between 0.005% and 6% by weight relative to the total weight of the dye composition.

Preferably, the composition according to the invention contains at least one of the following combinations of oxidation dyes, the bases A1 and A2 and the couplers B1, B2, B3, B4, B5 and B6 being as defined previously:

A1 and B1 and B2 and B3
A1 and B1 and B2 and B4
A1 and B1 and B2 and B5
A1 and B1 and B2 and B6
A1 and B1 and B3 and B4
A1 and B1 and B3 and B5
A1 and B1 and B3 and B6
A1 and B1 and B4 and B5
A1 and B1 and B4 and B6
A1 and B1 and B5 and B6
A1 and B2 and B3 and B4
A1 and B2 and B3 and B5
A1 and B2 and B3 and B6
A1 and B2 and B4 and B5
A1 and B2 and B4 and B6
A1 and B2 and B5 and B6
A1 and B3 and B4 and B5
A1 and B3 and B4 and B6
A1 and B4 and B5 and B6
A2 and B1 and B2 and B3
A2 and B1 and B2 and B4
A2 and B1 and B2 and B5

A2 and B1 and B2 and B6
A2 and B1 and B3 and B4
A2 and B1 and B3 and B5
A2 and B1 and B3 and B6
A2 and B1 and B4 and B5
A2 and B1 and B4 and B6
A2 and B1 and B5 and B6
A2 and B2 and B3 and B4
A2 and B2 and B3 and B5
A2 and B2 and B3 and B6
A2 and B2 and B4 and B5
A2 and B2 and B4 and B6
A2 and B2 and B5 and B6
A2 and B3 and B4 and B5
A2 and B3 and B4 and B6
A2 and B4 and B5 and B6
A1 and A2 and B1 and B2
A1 and A2 and B1 and B3
A1 and A2 and B1 and B4
A1 and A2 and B1 and B5
A1 and A2 and B1 and B6
A1 and A2 and B2 and B3
A1 and A2 and B2 and B4
A1 and A2 and B2 and B5
A1 and A2 and B2 and B6
A1 and A2 and B3 and B4
A1 and A2 and B3 and B5
A1 and A2 and B3 and B6
A1 and A2 and B4 and B5
A1 and A2 and B4 and B6
A1 and A2 and B5 and B6.

In one variant of the invention, the compositions of the invention contain as oxidation dyes only compounds chosen from the compounds of the type A1, A2, B1, B2, B3, B4, B5 and B6 as defined previously.

The dye composition in accordance with the invention may also contain one or more direct dyes that may be chosen especially from nitrobenzene dyes, azo direct dyes and methine direct dyes. These direct dyes may be of nonionic, anionic or cationic nature. They may be synthetic or of natural origin.

The medium that is suitable for dyeing, also known as the dye support, generally comprises water or a mixture of water and of one or more organic solvents, for instance $C_1$-$C_4$ lower alkanols such as ethanol and isopropanol, polyols, for instance propylene glycol, dipropylene glycol or glycerol, and polyol ethers, for instance dipropylene glycol monomethyl ether.

The solvent(s) are generally present in proportions that may be between 1% and 40% by weight approximately and even more preferentially between 3% and 30% by weight approximately relative to the total weight of the dye composition.

The dye composition in accordance with the invention may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric polymeric associative thickeners, antioxidants, penetrating agents, sequestering agents, fragrances, buffers, dispersants, conditioning agents, for instance volatile or non-volatile, modified or unmodified silicones, film-forming agents, ceramides, preserving agents and opacifiers.

The above adjuvants are generally present in an amount, for each of them, of between 0.01% and 20% by weight relative to the weight of the composition.

Needless to say, a person skilled in the art will take care to select this or these optional additional compound(s) such that the advantageous properties intrinsically associated with the oxidation dye composition in accordance with the invention are not, or are not substantially, adversely affected by the envisaged addition(s).

The pH of the dye composition in accordance with the invention is generally between 3 and 12 approximately and preferably between 5 and 11 approximately. It may be adjusted to the desired value by means of acidifying or basifying agents usually used in the dyeing of keratin fibres, or alternatively using standard buffer systems.

Among the acidifying agents that may be mentioned, for example, are mineral or organic acids, for instance hydrochloric acid, (ortho)phosphoric acid or sulfuric acid, carboxylic acids, for instance acetic acid, tartaric acid, citric acid and lactic acid, and sulfonic acids.

Among the basifying agents, examples that may be mentioned include aqueous ammonia, alkali metal carbonates, sodium metasilicate, sodium silicate, alkanolamines such as monoethanolamine, diethanolamine, triethanolamine and derivatives thereof, for example monoethanolamine, aminomethylpropanol, triethanolamine, sodium hydroxide or potassium hydroxide, for example sodium hydroxide, sodium pyrrolidinecarboxylate, and the compounds of formula (X) below:

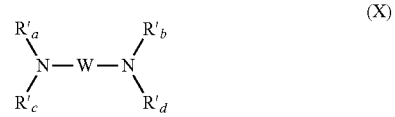

in which W is a propylene residue optionally substituted with a hydroxyl group or a $C_1$-$C_4$ alkyl radical; $R_a$, $R_b$, $R_c$ and $R_d$, which may be identical or different, represent a hydrogen atom or a $C_1$-$C_4$ alkyl or $C_1$-$C_4$ hydroxyalkyl radical.

The composition according to the invention may comprise one or more oxidizing agents.

The oxidizing agents are those conventionally used for the oxidation dyeing of keratin fibres, for example hydrogen peroxide, urea peroxide, alkali metal bromates, persalts such as perborates and persulfates, peracids and oxidase enzymes, among which mention may be made of peroxidases, two-electron oxidoreductases such as uricases, and four-electron oxygenases, for instance laccases. Hydrogen peroxide is particularly preferred.

The composition with or without oxidizing agent according to the invention may be in various forms, such as in the form of liquids, creams or gels, or in any other form that is suitable for dyeing keratin fibres, and especially human hair.

It may result from the mixing at the time of use of several compositions.

In one particular variant, it results from the mixing of two compositions, one comprising at least four oxidation dye precursors including at least one oxidation base chosen from the pyrazolopyridines of formulae (I) and (II) and the diamino-N,N-dihydropyrazolone derivatives of formula (III) and at least one coupler chosen from the cationic 3,5-diaminopyridines of formula (IV) and the 4-aminoindoles of formula (V), 5-amino-6-chloro-2-methylphenol, 6-hydroxybenzomorpholine, 2-methyl-5-hydroxyethylaminophenol and 2-amino-3-hydroxypyridine, and also the addition salts thereof, solvates thereof or solvates of the salts thereof, and another composition comprising at least one oxidizing agent as described previously.

The composition of the invention is thus applied to the hair for the dyeing of keratin fibres, either in unmodified form or in the presence of at least one oxidizing agent for the dyeing of keratin fibres.

The process of the present invention is a process in which the composition free of oxidizing agent according to the present invention as defined previously is applied to the fibres in the presence of an oxidizing agent for a time that is sufficient to develop the desired colouration. The colour may be revealed at acidic, neutral or alkaline pH, and the oxidizing agent may be added to the composition of the invention right at the time of use, or it may be used starting with an oxidizing composition containing it, which is applied simultaneously with or sequentially to the composition of the invention.

According to one particular embodiment, the composition free of oxidizing agent according to the present invention is mixed, preferably at the time of use, with a composition containing, in a suitable dyeing medium, at least one oxidizing agent. The mixture obtained is then applied to the keratin fibres. After a contact time of 3 to 50 minutes approximately and preferably 5 to 30 minutes approximately, the keratin fibres are rinsed, optionally washed with shampoo, rinsed again and then dried.

The oxidizing agents are those described previously.

The oxidizing composition may also contain various adjuvants conventionally used in compositions for dyeing the hair and as defined above.

The pH of the oxidizing composition containing the oxidizing agent is such that, after mixing with the dye composition, the pH of the resulting composition applied to the keratin fibres preferably ranges between 3 and 12 approximately and even more preferentially between 5 and 11. It may be adjusted to the desired value by means of acidifying or basifying agents usually used in the dyeing of keratin fibres and as defined previously.

A subject of the invention is also a multi-compartment dyeing device or "kit", in which a first compartment contains the dye composition free of oxidizing agent of the present invention defined above comprising at least four oxidation dye precursors including at least one oxidation base chosen from the pyrazolopyridines of formulae (I) and (II) and the diamino-N,N-dihydropyrazolone derivatives of formula (III) and at least one coupler chosen from the cationic 3,5-diaminopyridines of formula (IV) and the 4-aminoindoles of formula (V), 5-amino-6-chloro-2-methylphenol, 6-hydroxybenzomorpholine, 2-methyl-5-hydroxyethylaminophenol and 2-amino-3-hydroxypyridine, and also the addition salts thereof, solvates thereof or solvates of the salts thereof, and a second compartment contains at least one oxidizing agent.

A second device is formed from a first compartment containing a composition comprising the oxidation base(s) present in the composition in accordance with the invention, and also the addition salts thereof, solvates thereof or solvates of the salts thereof, and a second compartment containing a composition comprising the coupler(s) present in the composition in accordance with the invention, and also the addition salts thereof, solvates thereof or solvates of the salts thereof.

A third device may optionally comprise the two compartments of the second device plus a third compartment containing a composition comprising at least one oxidizing agent.

These devices may be equipped with a means for dispensing the desired mixture on the hair, such as the devices described in patent FR-2 586 913 in the name of the Applicant.

The compounds of formula (III) are synthesized according to a procedure such as those described in document EP 0 550 656.

The cationic aminopyridines of formula (IV) as defined above may be prepared via various synthetic routes.

They may especially be prepared from the compounds of formula (IV') below:

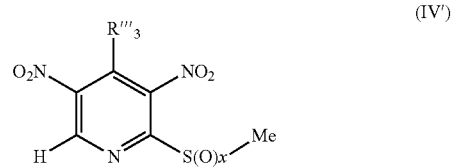

in which $R'''_3$ is chosen from a hydrogen atom, halogens chosen from fluorine, chlorine and bromine, and linear or branched $C_1$-$C_4$ alkyl, carboxyl (—COOH) and ($C_1$-$C_4$) alkoxycarbonyl radicals, and x represents 0; 1 or 2.

More particularly, the cationic aminopyridines of formula (IV) may be prepared from a compound of formula (IV"):

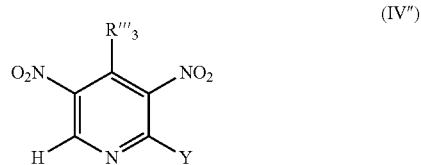

in which Y represents a halogen or a group $SO_2R'''_4$ with $R'''_4$ chosen from $C_1$-$C_4$ alkyls, preferably methyl, a phenyl radical or a methylphenyl radical;

and $R'''_3$ is chosen from a hydrogen atom, halogens chosen from fluorine, chlorine and bromine, and linear or branched $C_1$-$C_4$ alkyl, carboxyl (—COOH) and ($C_1$-$C_4$)alkoxycarbonyl radicals;

according to a process comprising at least the following steps, in this order:

substitution of the group Y with a group $Z''''_1R''''_1$ as defined above;

reduction of the nitro groups.

This process is summarized in the scheme below:

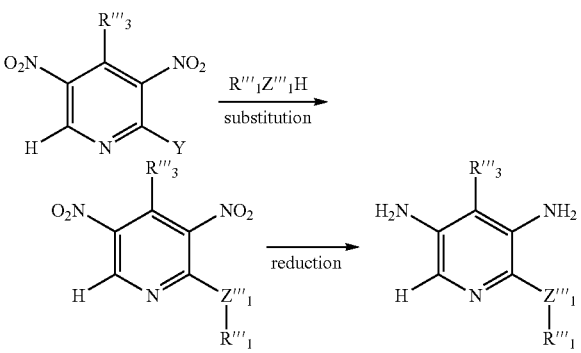

By way of example, when $R'''_1$ represents a $C_1$-$C_{10}$ alkyl radical substituted with a cationic radical, the said alkyl radical being interrupted with one or more oxygen atoms and/or with one or more groups $NR'''_2$, then the synthetic process used may be the following:

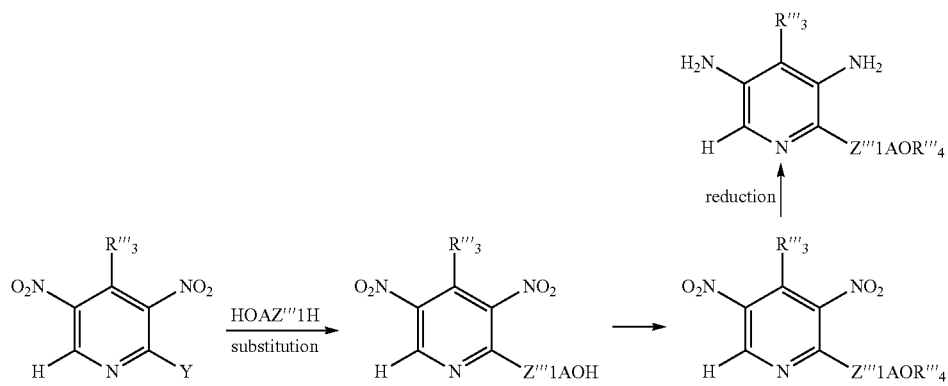

in which A represents a linear or branched alkyl chain optionally interrupted with a heteroatom such as O, N or S.

The substitution reaction is performed in a dipolar solvent such as acetonitrile, THF or in DMF or NMP, or in an alcohol such as ethanol, in the presence of a base such as triethylamine, ethyldiisopropylamine, sodium hydroxide or potassium hydroxide, for example, and one or more HOAZ'''1H for 1 to 24 hours at a temperature from 20° C. to the reflux temperature of the solvent.

The hydroxyl function thus introduced is then substituted with a halide (for example mesyl or tosyl halide) in a solvent such as acetonitrile or THF or in an alcohol such as ethanol, for example, in the presence of a base such as triethylamine, ethyldiisopropylamine, sodium hydroxide or potassium hydroxide, for example, for 1 to 24 hours at a temperature from 20° C. to the reflux temperature of the solvent.

The substitution of the leaving group introduced in the preceding step is performed either by reaction with an aromatic tertiary amine such as methylimidazole to lead directly to the cationic compounds, or by reaction with a particular primary or secondary amine, for instance N,N-dimethylethylenediamine or 2-piperidin-1-ylethanamine to lead to the compounds that are alkylated with at least one equivalent of alkyl halide or of methyl sulfate in a solvent such as THF or acetonitrile or dioxane or ethyl acetate for 15 minutes to 24 hours at a temperature ranging from 15° C. to the reflux temperature of the solvent, to give the cationic nitro compounds.

The reduction of the nitro group of these compounds is performed under standard conditions, for example by performing a hydrogenation reaction under heterogeneous catalysis in the presence of Pd/C, Pd(II)/C, Ni/Ra, etc., or alternatively by performing a reduction reaction with a metal, for example with zinc, iron, tin, etc. (see *Advanced Organic Chemistry*, 3rd Edition, J. March, 1985, Wiley Interscience and *Reduction in Organic Chemistry*, M. Hudlicky, 1983, Ellis Horwood Series Chemical Science).

According to a second particular embodiment, the synthesis of the compounds of formula (V) is performed according to the following scheme:

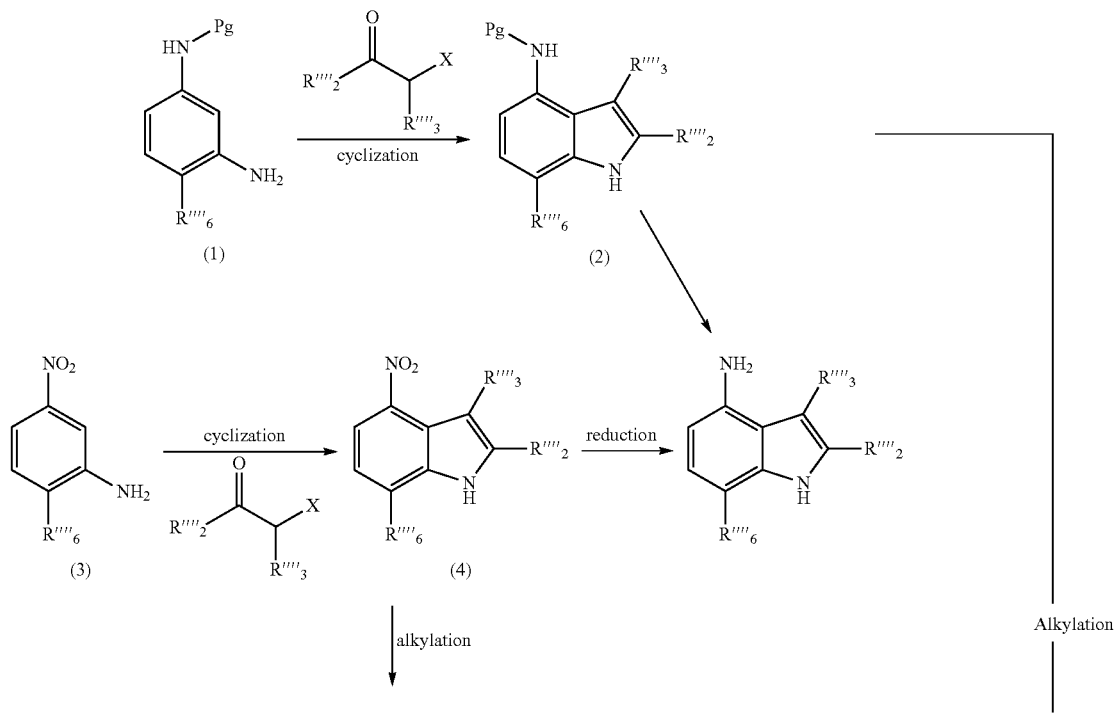

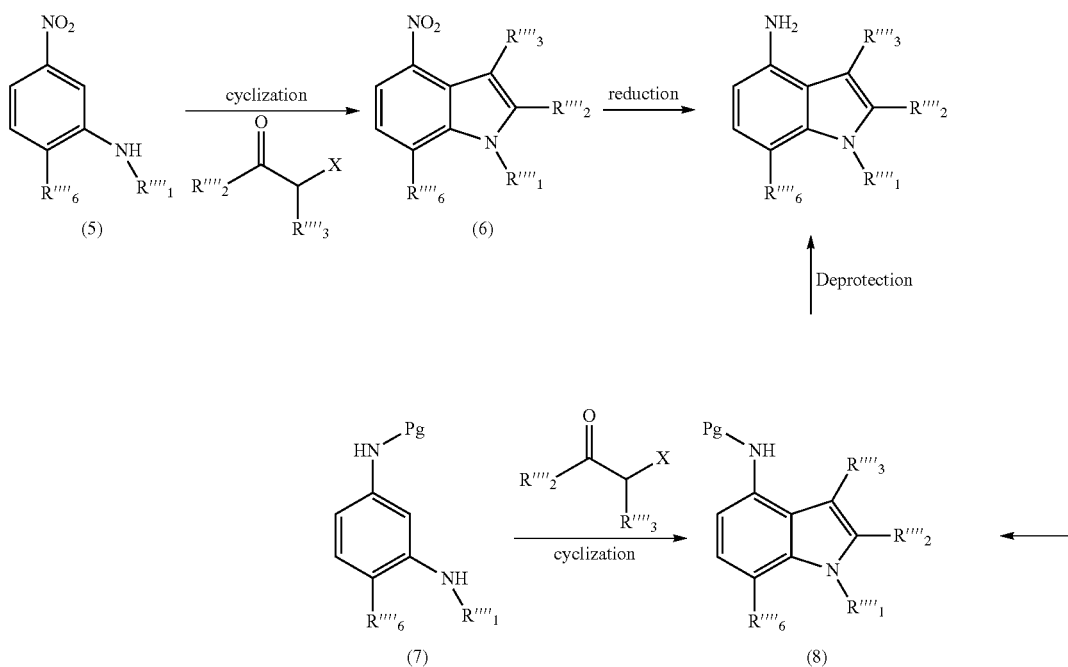

in which:
Pg is a protecting group for the amine function chosen from those mentioned in the publication *Protective Groups in Organic Synthesis*, T. W. Greene, P. G. M. Wutz, John Wiley & Sons, 2nd Ed, 1991;

X denotes a halogen atom such as a fluorine, chlorine, bromine or iodine atom.

According to another particular embodiment, the synthesis of the compounds of formula (V) is performed according to the following scheme:

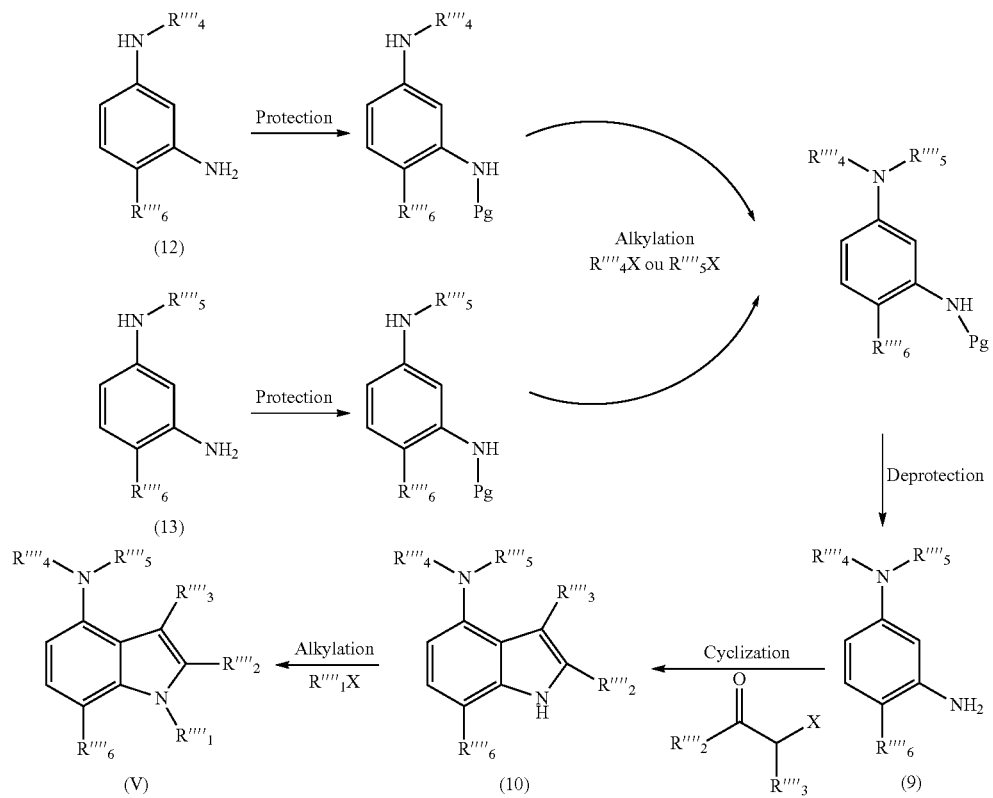

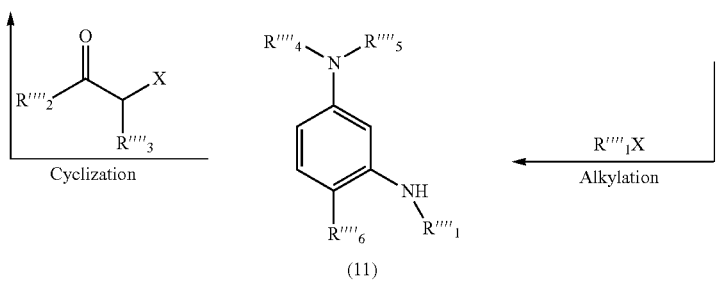

The compounds (2) are obtained from the protected amines (1) via a cyclization reaction of Bischler type performed in a dipolar solvent such as DMF, NMP, acetonitrile or THF, or in an alcohol such as ethanol, for example, optionally in the presence of an organic or mineral base such as triethylamine, ethyldiisopropylamine, sodium hydroxide or potassium hydroxide, with 0.5 to 1 or more equivalents of carbonyl halide R''''$_2$—CO—CHX—R''''$_3$ for 1 to 24 hours at a temperature ranging from 20° C. to the reflux temperature of the solvent. The cyclization reactions of (3) to lead to (4), or of (5) to lead to (6), or of (7) to lead to (8), or of (9) to lead to (10), or of (11) to lead to (V), are performed in the same manner.

The alkylation of compounds (4) is performed with at least one equivalent of alkyl halide R''''$_1$—X in a solvent such as THF or acetonitrile or dioxane or ethyl acetate, in the presence of an organic or mineral base such as triethylamine, ethyldiisopropylamine, sodium hydroxide or potassium hydroxide, for 15 minutes to 24 hours at a temperature ranging from 15° C. to the reflux temperature of the solvent and leads to compounds (6). The alkylation of compounds (2) to give compounds (8), or of (9) to give (11), or of (10) to give (V), is performed according to an identical protocol.

The reduction of the nitro group of the compounds (4) and (6) is performed under standard conditions, for example by performing a hydrogenation reaction under heterogeneous catalysis in the presence of a catalyst such as Pd/C, Pd(II)/C or Ni/Ra, or alternatively by performing a reduction reaction with a metal, for example with zinc, iron or tin (see *Advanced Organic Chemistry*, 3rd Edition, J. March, 1985, Wiley Interscience and *Reduction in Organic Chemistry*, M. Hudlicky, 1983, Ellis Horwood Series Chemical Science).

The cleavage of the protecting group Pg may be performed in acidic or basic medium in a very conventional manner, depending on their nature (see *Protective Groups for Organic Synthesis*, T. W. Greene, P. G. M. Wutz, John Wiley & Sons, 2$^{nd}$ Ed, 1991).

When compounds (9) are not commercially available, they may be obtained, for example, from the diamines (12) or (13).

The examples that follow serve to illustrate the invention without, however, being limiting in nature.

EXAMPLES

Synthesis Examples

Example 1

Synthesis of 2-[(3,5-diaminopyridin-2-yl)amino]-N,N,N-trimethylethanammonium chloride dihydrochloride

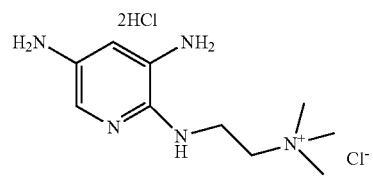

Step 1: Synthesis of N'-(3,5-dinitropyridin-2-yl)-N,N-dimethylethane-1,2-diamine

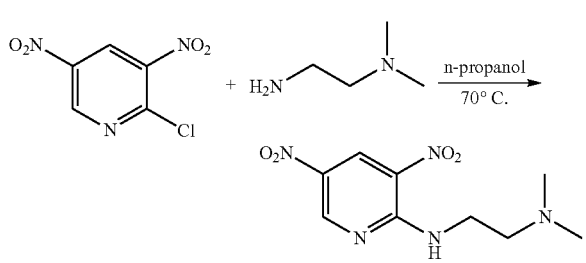

30 ml of ethanol and 10.15 g (0.05 mol) of 2-chloro-3,5-dinitropyridine are successively placed in a 50 ml three-necked flask equipped with a thermometer, a condenser, a bubbler and a dropping funnel, with magnetic stirring. The medium is brought to 40° C., 8.8 g (0.1 mol) of N,N-dimethylethane-1,2-diamine are added dropwise over 5 minutes using the dropping funnel, and the mixture is stirred for 1 hour.

After cooling the reaction medium, it is poured into a mixture of ice and water with stirring.

The yellow solid formed is isolated by filtration on a sinter funnel, washed with water and dried under vacuum at 30° C. in the presence of a desiccant, to constant weight. 10.5 g (yield 82.5%) of the expected compound are thus isolated in the form of a yellow solid.

Analysis by mass spectrometry confirms the expected structure: the quasi-molecular ions $[M+H]^+$ and $[M+Na]^+$ of the expected molecule are mainly detected, $C_9H_{13}N_5O_4$.

Step 2: Synthesis of 2-[(3,5-dinitropyridin-2-yl)amino]-N,N,N-trimethylethanammonium methyl sulfate

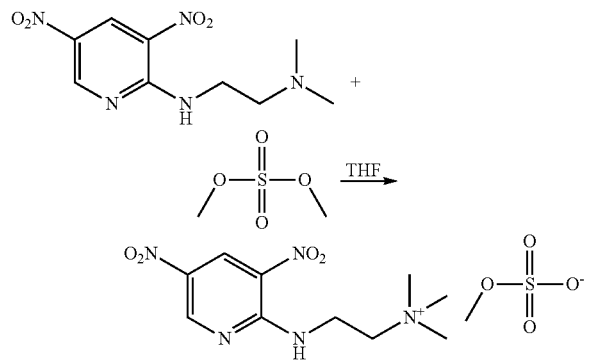

50 ml of ethyl acetate and 6.38 g (25 mmol) of N'-(3,5-dinitropyridin-2-yl)-N,N-dimethylethane-1,2-diamine are successively placed in a 100 ml three-necked flask equipped with a thermometer, a condenser, a bubbler and a dropping funnel, with magnetic stirring. 3.15 g (25 mmol) of dimethyl sulfate are added to this solution, and the mixture is stirred for one hour.

The yellow solid formed is filtered off, drained by suction, washed with ethyl acetate and then dried under vacuum at 50° C. in the presence of a desiccant, to constant mass. 7 g (73% yield) of the expected compound are thus obtained in the form of a yellow solid.

Analysis by mass spectrometry confirms the expected compound, the expected cation $[C_{10}H_{16}N_5O_4]^+$ is mainly detected at m/z, ESP+=270.

Step 3: Synthesis of 2-[(3,5-diaminopyridin-2-yl)amino]-N,N,N-trimethylethanammonium chloride dihydrochloride

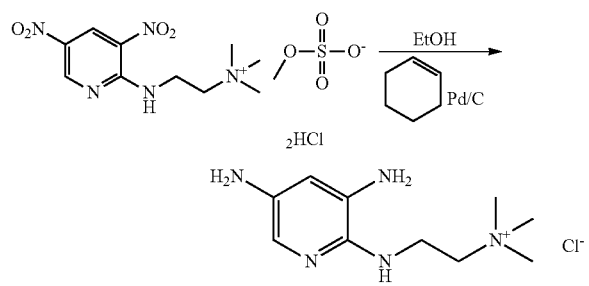

300 ml of ethanol, 20 ml of water, 24 g (62.95 mmol) of 2-[(3,5-dinitropyridin-2-yl)amino]-N,N,N-trimethylethanammonium methyl sulfate and 52 ml (503 mmol) of cyclohexene are successively placed in a 1 liter three-necked flask equipped with a thermometer, a condenser and a bubbler, with magnetic stirring. The medium is brought to 50° C., 12 g of palladium-on-charcoal are introduced portionwise, and the mixture is refluxed for 2 hours.

After cooling under argon, the reaction medium is filtered under a stream of argon on a sinter funnel packed with Celite and a vacuum flask containing 200 ml of 6.0 N hydrochloric 2-propanol at 0° C.

The expected compound crystallizes in the vacuum flask with stirring. The solid is filtered off, rapidly drained under vacuum on a sinter funnel and under argon, and rinsed with a minimum amount of cold iPrOH and then with 3×100 ml of iPr$_2$O. The compound is dried under vacuum at 50° C. in the presence of a desiccant, to constant weight. 17.5 g (87.4% yield) of the expected compound are thus obtained in the form of a beige-coloured solid.

The NMR ($^1$H 400 MHz and $^{13}$C 100.61 MHz DMSO-d$_6$) and mass spectrometry analyses are in accordance with the expected structure.

Example 2

Synthesis of 2-[(3,5-diaminopyridin-2-yl)(methyl)amino]-N,N,N-trimethylethanammonium chloride dihydrochloride

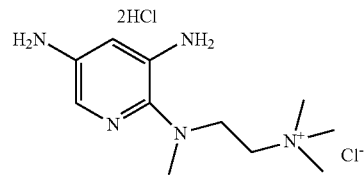 [SMILES: CN(CC[N+](C)(C)C)c1ncc(N)cc1N ; [Cl-]]

Step 1: Synthesis of N-(3,5-dinitropyridin-2-yl)-N,N',N'-trimethylethane-1,2-diamine

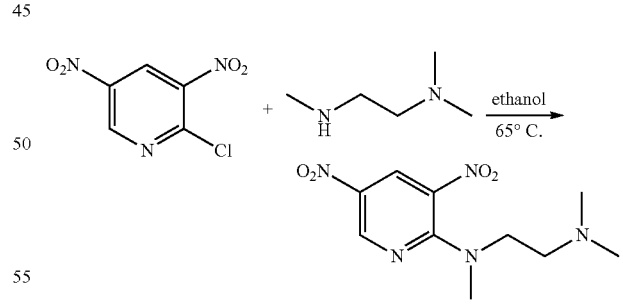

50 ml of ethanol and 12.30 g (60.43 mmol) of 2-chloro-3,5-dinitropyridine are successively placed in a 250 ml three-necked flask equipped with a thermometer, a condenser, a bubbler and a dropping funnel, with magnetic stirring. The medium is brought to 40° C., 9.26 ml (72.52 mmol) of N,N,N'-trimethylethane-1,2-diamine are added dropwise over 5 minutes using the dropping funnel, and the mixture is maintained at 65° C. for 1 hour.

After cooling the reaction medium, it is poured into a mixture of 200 g of ice and water with stirring.

The yellow solid formed is isolated by filtration on a sinter funnel, washed with water and dried under vacuum at 30° C. in the presence of a desiccant, to constant weight. 10.7 g (yield 62%) of yellow solid corresponding to the expected compound are thus isolated.

Analysis by mass spectrometry confirms the expected structure: the quasi-molecular ions [M+H]$^+$ and [M+Na]$^+$ of the expected molecule are mainly detected, $C_{10}H_{15}N_5O_4$.

Step 2: 2-[(3,5-dinitropyridin-2-yl)(methyl)amino]-N,N,N-trimethylethanammonium methyl sulfate

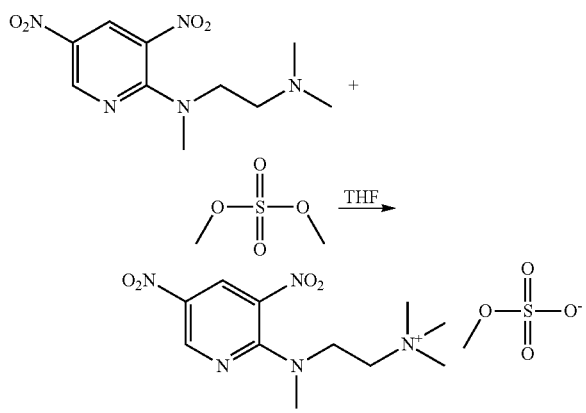

300 ml of ethyl acetate and 15.80 g (60 mmol) of N-(3,5-dinitropyridin-2-yl)-N,N',N'-trimethylethane-1,2-diamine are successively placed in a 500 ml three-necked flask equipped with a thermometer, a condenser, a bubbler and a dropping funnel, with magnetic stirring.

12 g (120 mmol) of dimethyl sulfate are added dropwise to this solution, and the mixture is stirred at reflux for one hour.

After cooling, the yellow solid formed is filtered off on a sinter funnel, drained by suction, washed with ethyl acetate and then dried under vacuum at 50° C. in the presence of a desiccant, to constant mass. 22.3 g (94% yield) of the expected compound are thus obtained in the form of a yellow solid.

Analysis by mass spectrometry confirms the expected structure: the expected cation $[C_{11}H_{18}N_5O_4]^+$ is mainly detected at m/z, ESP+=284.

Step 3: Synthesis of 2-[(3,5-diaminopyridin-2-yl)(methyl)amino]-N,N,N-trimethylethanammonium chloride dihydrochloride

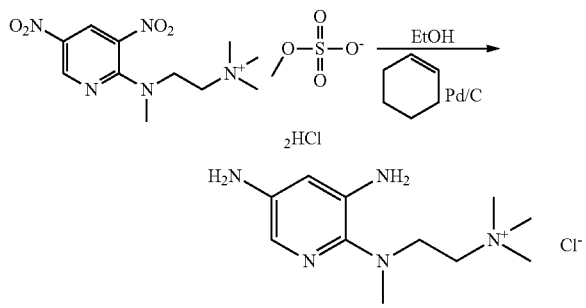

300 ml of ethanol, 5 ml of water, 20 g (50.60 mmol) of 2-[(3,5-dinitropyridin-2-yl)amino]-N,N,N-trimethylethanammonium methyl sulfate and 104 ml of cyclohexene are successively placed in a 1 liter three-necked flask equipped with a thermometer, a condenser and a bubbler, with magnetic stirring.

The medium is brought to 50° C., 5 g of palladium-on-charcoal are introduced portionwise, and the mixture is refluxed for 2 hours.

After cooling under argon, the reaction medium is filtered under a stream of argon on a sinter funnel packed with Celite and a vacuum flask containing 250 ml of 6.0 N hydrochloric 2-propanol at 0° C.

The expected compound which crystallizes in the flask with stirring is filtered off, rapidly drained under vacuum on a sinter funnel and under argon, and rinsed with a minimum amount of cold iPrOH and then with 3×100 ml of iPr$_2$O. The compound is dried under vacuum at 50° C. in the presence of a desiccant, to constant weight. 12.1 g (81% yield) of the expected compound are thus obtained in the form of a beige-coloured solid.

The NMR ($^1$H 400 MHz and $^{13}$C 100.61 MHz DMSO-d$_6$) and mass spectrometry analyses are in accordance with the expected structure.

Example 3

Synthesis of 4-(3,5-diaminopyridin-2-yl)-1,1-dimethylpiperazin-1-ium chloride dihydrochloride

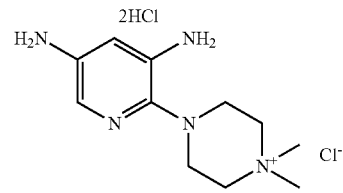

Step 1: Synthesis of 1-(3,5-dinitropyridin-2-yl)-4-methylpiperazine

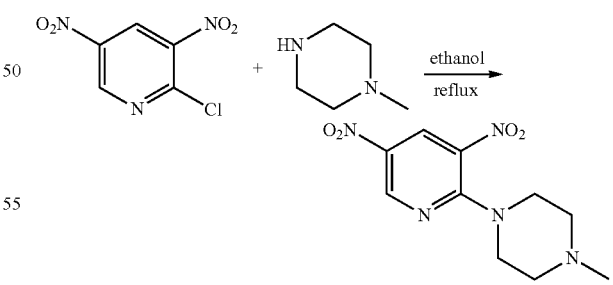

40 ml of ethanol and 5 g (24.57 mmol) of 2-chloro-3,5-dinitropyridine are successively placed in a 250 ml three-necked flask equipped with a thermometer, a condenser, a bubbler and a dropping funnel, with magnetic stirring. The medium is brought to 40° C., 6.15 ml (49.13 mmol) of methylpiperazine are added dropwise over 5 minutes using the dropping funnel, and the mixture is refluxed for 1 hour and then left stirring at room temperature overnight.

A yellow solid crystallizes from the medium; it is isolated by filtration on a sinter funnel, washed with water and dried under vacuum at 30° C. in the presence of a desiccant, to constant weight. 5.7 g (88% yield) of the expected compound are thus obtained in the form of a yellow solid.

Analysis by mass spectrometry confirms the structure of the expected compound. The quasi-molecular ions [M+H]+ and [M+Na]+ of the expected molecule are mainly detected, $C_{10}H_{13}N_5O_4$.

Step 2: Synthesis of 4-(3,5-dinitropyridin-2-yl)-1,1-dimethylpiperazin-1-ium methyl sulfate

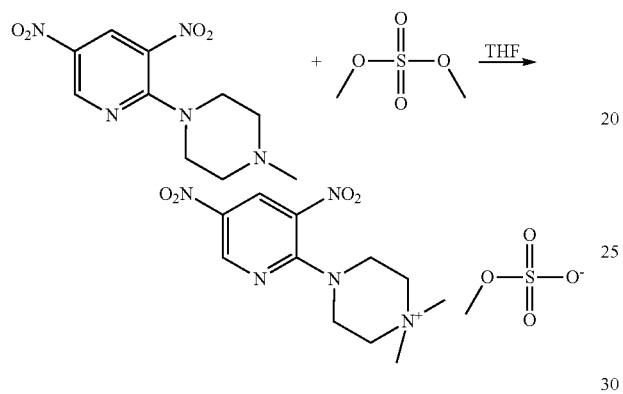

100 ml of THF and 5.5 g (20 mmol) of 1-(3,5-dinitropyridin-2-yl)-4-methylpiperazine are successively placed in a 200 ml three-necked flask equipped with a thermometer, a condenser, a bubbler and a dropping funnel, with magnetic stirring. 4.19 g (40 mmol) of dimethyl sulfate are added dropwise to this solution, and the mixture is stirred at reflux for one hour.

The yellow solid formed is filtered off on a sinter funnel, drained by suction, washed with THF and then dried under vacuum at 50° C. in the presence of a desiccant, to constant mass. 7.4 g (94% yield) of the expected compound are thus obtained in the form of a yellow solid.

Analysis by mass spectrometry confirms the structure of the expected compound. The expected cation $[C_{15}H_{16}N_5O_4]+$ is mainly detected.

Step 3: Synthesis of 4-(3,5-diaminopyridin-2-yl)-1,1-dimethylpiperazin-1-ium chloride hydrochloride

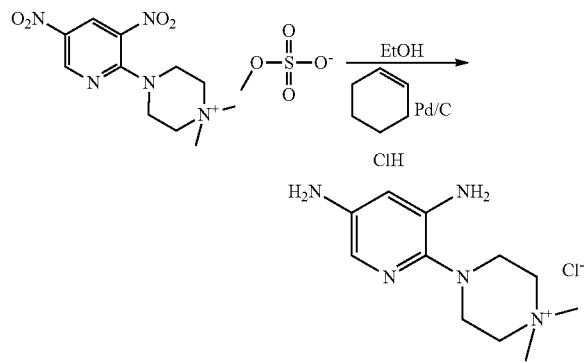

50 ml of ethanol, 1 ml of water, 20 g (50.60 mmol) of 4-(3,5-dinitropyridin-2-yl)-1,1-dimethylpiperazin-1-ium methyl sulfate and 36.56 ml of cyclohexene are successively placed in a 250 ml three-necked flask equipped with a thermometer, a condenser and a bubbler, with magnetic stirring.

The medium is brought to 50° C., 3.5 g of palladium-on-charcoal are introduced portionwise, and the mixture is refluxed for 24 hours.

The reaction medium is filtered under argon on a sinter funnel packed with Celite and a vacuum flask containing 250 ml of 6.0 N hydrochloric 2-propanol at 0° C. The expected compound crystallizes in the flask with stirring; it is filtered off on a centre funnel, drained rapidly by vacuum under argon, and rinsed with a minimum amount of cold iPrOH and then with 3×100 ml of iPr$_2$O. The solid is then dried under vacuum at 50° C. in the presence of a desiccant, to constant weight. 4.6 g (88% yield) of the expected compound are thus obtained in the form of a beige-coloured solid.

The NMR ($^1$H 400 MHz and $^{13}$C 100.61 MHz DMSO-d$_6$) and mass spectrometry analyses are in accordance with the expected structure. The expected cation $[C_{11}H_{20}N_5]^+$ is mainly detected.

Example 4

Synthesis of 1-{2-[(3,5-diaminopyridin-2-yl)amino]ethyl}-1-methylpiperidinium chloride dihydrochloride, 2HCl

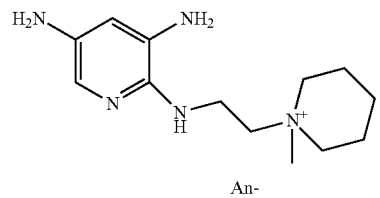 [SMILES: C[N+]1(CCNc2ncc(N)cc2N)CCCCC1]

with An- is Cl$^-$

Step 1: Synthesis of 3,5-dinitro-N-(2-piperidin-1-ylethyl)pyridin-2-amine

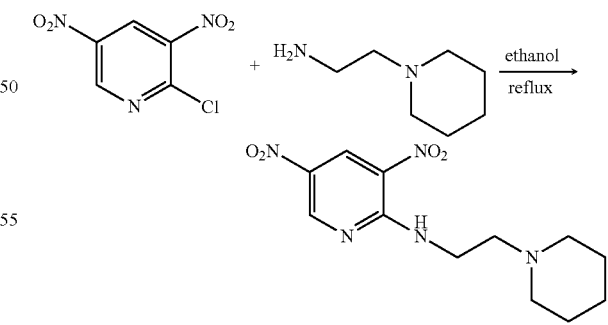

800 ml of ethanol and 10.17 g (50 mmol) of 2-chloro-3,5-dinitropyridine are successively placed in a 250 ml three-necked flask equipped with a thermometer, a condenser, a bubbler and a dropping funnel, with magnetic stirring. This medium is brought to 40° C., 7 ml of 2-aminoethylpiperidine are added dropwise over 5 minutes using the dropping funnel, and the mixture is stirred for 1 hour.

The medium, which has become heterogeneous, is then poured onto 500 g of ice. A yellow solid precipitate is more abundantly; it is isolated by filtration on a sinter funnel, washed with water and dried under vacuum at 30° C. in the presence of a desiccant, to constant weight. 11.5 g (78% yield) of the expected compound are thus obtained in the form of a yellow solid.

Analysis by mass spectrometry confirms the structure of the expected compound: the quasi-molecular ions [M+H]+, [M+Na]+ of the expected molecule $C_{12}H_{17}N_6O_4$ are mainly detected.

Step 2: Synthesis of 1-{2-[(3,5-dinitropyridin-2-yl)amino]ethyl}-1-methylpiperidinium methyl sulfate

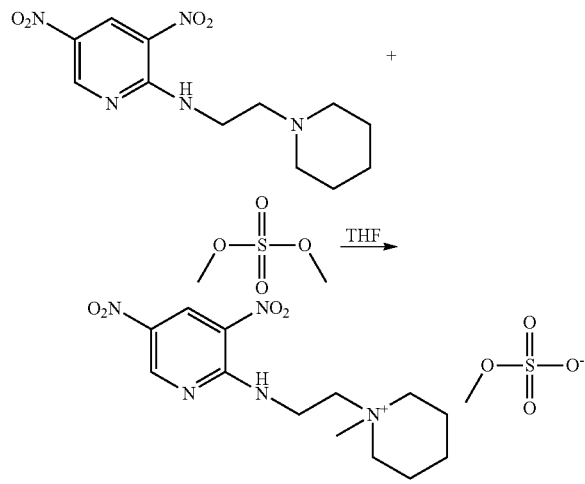

50 ml of ethyl acetate and 6.16 g (20 mmol) of 13,5-dinitro-N-(2-piperidin-1-ylethyl)pyridin-2-amine are successively placed in a 200 ml three-necked flask equipped with a thermometer, a condenser, a bubbler and a dropping funnel, with magnetic stirring.

2.52 g (20 mmol) of dimethyl sulfate are added dropwise to this solution, and the mixture is stirred for one hour.

The yellow solid formed is filtered off on a sinter funnel, drained by suction, washed with ethyl acetate and then dried under vacuum at 50° C. in the presence of a desiccant, to constant mass. 7.6 g (90% yield) of the expected compound are thus obtained in the form of a yellow solid.

Analysis by mass spectrometry confirms the structure of the expected compound. The expected cation $[C_{13}H_{20}N_5O_4]^+$ is mainly detected.

Step 3: Synthesis of 1-{2-[(3,5-diaminopyridin-2-yl)amino]ethyl}-1-methylpiperidinium chloride dihydrochloride

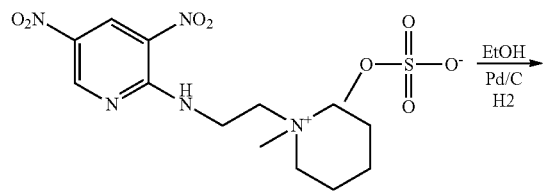

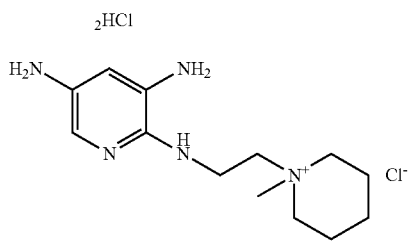

150 ml of ethanol, 5 ml of water, 6 g (14.2 mmol) of 1-{2-[(3,5-dinitropyridin-2-yl)amino]ethyl}-1-methylpiperidinium methyl sulfate and 1.2 g of palladium-on-charcoal are successively placed in a 300 ml hydrogenation autoclave.

After purging the medium with nitrogen and then with hydrogen, the reaction is performed under a hydrogen pressure of 8 bar with an exothermicity of 75° C.

After cooling and purging with hydrogen, the catalyst is removed under nitrogen and the liquors are poured, under nitrogen, into 100 ml of 6N hydrochloric isopropanol.

The beige-coloured solid which crystallizes slowly under cold conditions is rapidly drained under vacuum on a sinter funnel and under argon, and rinsed with a minimum amount of cold iPrOH and then with 3×100 ml of $iPr_2O$. The solid obtained is dried under vacuum at 50° C. in the presence of a desiccant, to constant weight. 4.8 g (94% yield) of the expected compound are thus obtained in the form of a beige-coloured solid.

The NMR ($^1$H 400 MHz and $^{13}$C 100.61 MHz DMSO-$d_6$) and mass spectrometry analyses are in accordance with the expected structure.

The expected cation $[C_{13}H_{24}N_5]^+$ is mainly detected.

Example 5

Synthesis of 1-(3,5-diaminopyridin-2-yl)-N,N,N-trimethylpyrrolidin-3-ammonium chloride hydrochloride

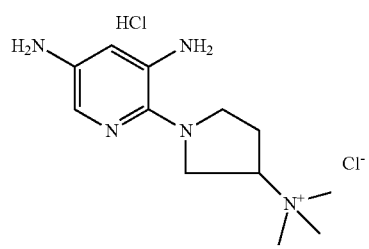 [SMILES: Cl ; C[N+](C)(C)C1CCN(c2ncc(N)cc2N)C1 ; [Cl-]]

The procedure is identical to that described in Example 4, the amine being N-dimethylpyrrolidin-3-amine.

Beige-coloured 1-(3,5-diaminopyridin-2-yl)-N,N,N-trimethylpyrrolidin-3-ammonium chloride hydrochloride is obtained in a yield of 65%.

The NMR ($^1$H 400 MHz and $^{13}$C 100.61 MHz DMSO-$d_6$) and mass spectrometry analyses are in accordance with the expected structure.

The expected cation $[C_{12}H_{22}N_5]^+$ is mainly detected.

Example 6

Synthesis of 1-{3-[(3,5-diaminopyridin-2-yl)amino]propyl}-3-(2-hydroxyethyl)-1H-imidazol-3-ium chloride dihydrochloride

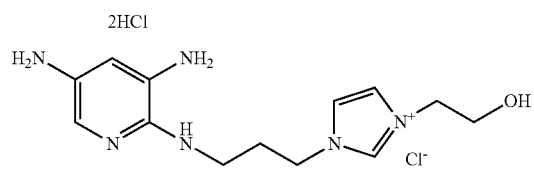 [SMILES: Nc1cnc(NCCCn2cc[n+](CCO)c2)c(N)c1 ; [Cl-]]

The processes performed in an identical manner to Example 4, with substitution using 3-aminopropylimidazole, and cationization using chloroethanol followed by a catalytic reduction in an autoclave.

The NMR ($^1$H 400 MHz and $^{13}$C 100.61 MHz DMSO-$d_6$) and mass spectrometry analyses are in accordance with the expected structure.

The expected cation $[C_{13}H_{21}N_6O]^+$ is mainly detected.

Example 7

Synthesis of 2,3,7-trimethyl-1H-indol-4-amine hydrochloride

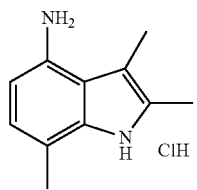

Step 1: synthesis of N-(2,3,7-trimethyl-1H-indol-4-yl)acetamide

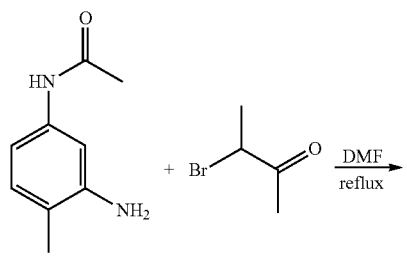

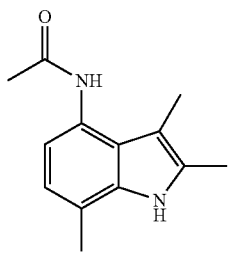

5 g (30 mmol) of N-(3-amino-4-methylphenyl)acetamide are placed in 12 ml of dimethylformamide in a 25 ml three-necked flask equipped with a condenser, a thermometer and a magnetic stirrer, and 3.24 ml (30 mmol) of 3-bromo-2-butanone are added dropwise. The mixture is then maintained at 100° C. for 8 hours until the starting material has totally disappeared.

The reaction medium is cooled and then poured into a mixture of ice and water.

The gummy precipitate formed is taken up in dichloromethane.

The organic phase is then washed with water, after which it is dried over sodium sulfate, and the solvents are then removed on a rotary evaporator under vacuum.

The crude product thus obtained is purified by flash chromatography on a column of silica (eluent: dichloromethane) to give, after removal of the solvent, 1.4 g of a beige-coloured powder corresponding to the expected product (yield=21.2%).

The NMR analyses ($^1$H 400 MHz and $^{13}$C 100.61 MHz DMSO-$d_6$) are in accordance with the expected structure.

The analysis by mass spectrometry confirms the structure of the expected compound $C_{13}H_{16}N_2O$. The quasi-molecular ions [M+H]+, [M+Na]+, [M−H]− of the expected molecule are mainly detected.

Step 2: Synthesis of 2,3,7-trimethyl-1H-indol-4-amine

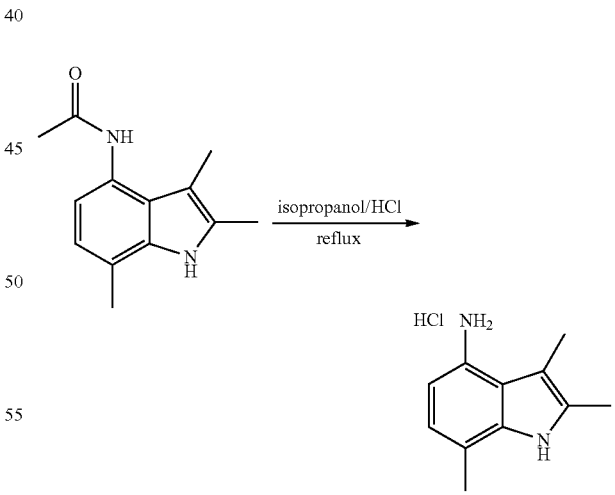

1.4 g (30 mmol) of N-(2,3,7-trimethyl-1H-indol-4-yl)acetamide are placed in 8 ml of a 50% solution of HCl in isopropanol in a 25 ml three-necked flask equipped with a condenser, a thermometer and a magnetic stirrer. The medium is refluxed for 48 hours.

The solvent is then removed under vacuum on a rotary evaporator to give 1.15 g of a grey powder corresponding to the expected compound (yield=64%).

The analysis by mass spectrometry confirms the expected structure $C_{11}H_{14}N_2$. The quasi-molecular ions [M+H]+, [M+Na]+, [M−H]− of the expected molecule are mainly detected.

Example 8

Synthesis of 2,3-dimethyl-7-(propan-2-yl)-1H-indol-4-amine hydrochloride

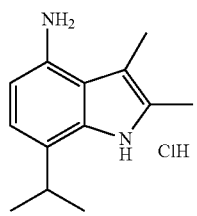

Step 1: synthesis of N-[2,3-dimethyl-7-(propan-2-yl)-1H-indol-4-yl]acetamide

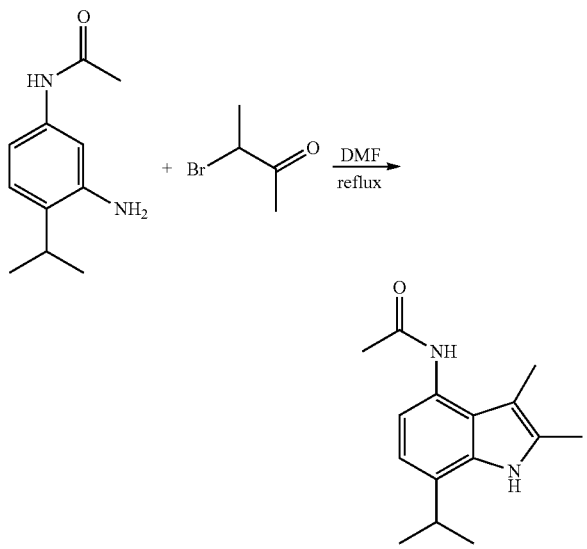

6.7 g (34.8 mmol) of N-[3-amino-4-(1-methylethyl)phenyl]acetamide are placed in 20 ml of dimethylformamide in a 25 ml three-necked flask equipped with a condenser, a thermometer and a magnetic stirrer, and 1.4 ml (13 mmol) of 3-bromo-2-butanone are then added dropwise.

The medium is then maintained at 100° C. for 48 hours, and is then cooled and poured into a mixture of ice and water, with stirring.

The precipitate formed is filtered off and washed thoroughly with water, and then dried under vacuum in the presence of a desiccant.

The crude product thus obtained is purified by flash chromatography on a column of silica (eluent: 95/5 dichloromethane/methanol) to give, after removal of the solvent, 2.87 g of a brown powder corresponding to the expected product (yield=51%).

The NMR analyses ($^1$H 400 MHz and $^{13}$C 100.61 MHz DMSO-$d_6$) are in accordance with the expected structure.

The analysis by mass spectrometry confirms the structure of the expected compound $C_{15}H_{20}N_2O$. The quasi-molecular ions [M+H]+, [M+Na]+, [M−H]− of the expected molecule are mainly detected.

Step 2: Synthesis of 2,3-dimethyl-7-(propan-2-yl)-1H-indol-4-amine hydrochloride

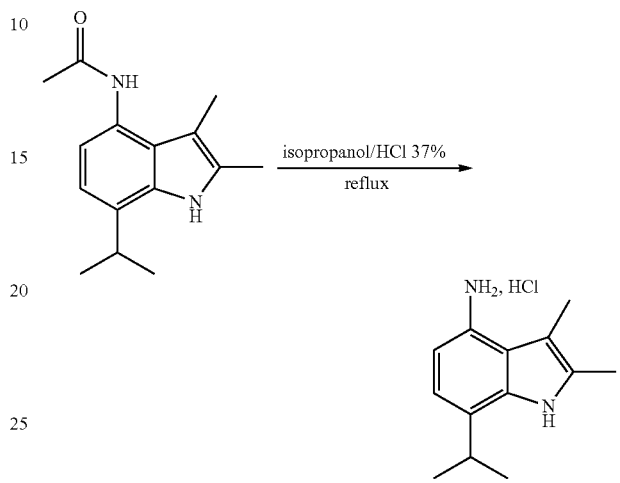

This compound is obtained according to a protocol identical to that described for Example 1, replacing the 6N HCl isopropanol solution with 6 ml of a 37.5% hydrochloric acid solution. For this example, the reaction of 2.87 g of N-[2,3-dimethyl-7-(propan-2-yl)-1H-indol-4-yl]acetamide leads to 2.8 g of a powder corresponding to the expected product (yield=89%).

The NMR analyses ($^1$H 400 MHz and $^{13}$C 100.61 MHz DMSO-$d_6$) are in accordance with the expected structure.

The analysis by mass spectrometry confirms the structure of the expected compound $C_{13}H_{18}N_2$. The quasi-molecular ions [M+H]+, [M+Na]+, [M−H]— of the expected molecule are mainly detected.

Examples of Dyeing

Compositions C1 to C7 below were prepared.

| Composition | C1 | C2 | C3 |
|---|---|---|---|
| 2-[(3-aminopyrazolo[1,5-a]pyridin-2-yl)oxy]ethanol hydrochloride | 0.008 mol | 0.003 mol | — |
| 4-(3-aminopyrazolo[1,5-a]pyridin-2-yl)-1,1-dimethylpiperazin-1-ium chloride hydrochloride | 0.002 mol | 0.0025 mol | 0.004 mol |
| 2,3-diamino-6,7-dihydro-1H,5H-pyrazolo[1,2-a]pyrazol-1-one dimethanesulfonate | — | 0.0015 mol | 0.004 mol |
| 7-methyl-1H-indol-4-amine | 0.008 mol | 0.0035 mol | — |
| 4-(3,5-diaminopyridin-2-yl)-1,1-dimethylpiperazin-1-ium chloride hydrochloride | 0.002 mol | 0.0035 mol | — |
| 2-methyl 5-hydroxyethylaminophenol | — | — | 0.0025 mol |
| 2-amino-3-hydroxypyridine | — | — | 0.0055 mol |
| Dye support | (*) | (*) | (*) |

| Composition | C4 | C5 |
|---|---|---|
| 2-[(3-aminopyrazolo[1,5-a]pyridin-2-yl)oxy]ethanol hydrochloride | 0.003 mol | 0.003 mol |

-continued

| | C4 | C5 |
|---|---|---|
| 4-(3-aminopyrazolo[1,5-a]pyridin-2-yl)-1,1-dimethylpiperazin-1-ium chloride hydrochloride | 0.005 mol | 0.005 mol |
| 2,3-diamino-6,7-dihydro-1H,5H-pyrazolo[1,2-a]pyrazol-1-one dimethanesulfonate | 0.001 mol | 0.002 mol |
| 2-methyl-5-hydroxyethylaminophenol | — | 0.01 mol |
| 5-amino-6-chloro-2-methylphenol | 0.009 mol | — |
| Dye support | (*) | (*) |

| Composition | C6 | C7 |
|---|---|---|
| 2-[(3-aminopyrazolo[1,5-a]pyridin-2-yl)oxy]ethanol hydrochloride | 0.008 mol | 0.004 mol |
| 2,3-diamino-6,7-dihydro-1H,5H-pyrazolo[1,2-a]pyrazol-1-one dimethanesulfonate | — | 0.004 mol |
| 6-hydroxybenzomorpholine | 0.002 mol | — |
| 2-methyl-5-hydroxyethylaminophenol | 0.004 mol | 0.0035 mol |
| 2-amino-3-hydroxypyridine | — | 0.001 mol |
| 5-amino-6-chloro-2-methylphenol | 0.002 mol | 0.0035 mol |
| Dye support | (*) | (*) |

| | |
|---|---|
| Oleyl alcohol polyglycerolated with 2 mol of glycerol | 4 g AM |
| Oleyl alcohol polyglycerolated with 4 mol of glycerol (78% AM) | 6 g AM |
| Oleic acid | 3 g |
| Oleylamine 2 OE sold under the name Ethomeen O12 by the company Akzo | 7 g AM |
| Diethylaminopropyl laurylaminosuccinate, sodium salt, at 55% AM | 3 g AM |
| Oleyl alcohol | 5 g |
| (50% linear 70/30 C13/C15)alkyl ether carboxylic acid monoethanolamide (2 OE) | 10 g AM |
| Propylene glycol | 9.5 g |
| Ethyl alcohol | 5 g |
| Hexylene glycol | 9.3 g |
| Sodium metabisulfite as an aqueous solution containing 35% AM | 0.455 g AM |
| Ammonium acetate | 0.8 g |
| Antioxidant, sequestrant | qs |
| Fragrance, preservative | qs |
| Aqueous ammonia containing 20% NH$_3$ | 10.2 g |
| Demineralized water | qs100 g |

Dye support: (*)
AM: Active Material

Mode of Application

Compositions C1 to C7 were diluted extemporaneously with 1 times their weight of 20-volumes aqueous hydrogen peroxide solution.

The mixtures thus obtained were then applied to locks of natural grey hair containing 90% white hairs, at a rate of 10 g of mixture per 1 g of hair. After a leave-on time of 30 minutes at room temperature, the hair was then rinsed, washed with a standard shampoo and dried.

Results

The hair colourations were evaluated visually.

| Composition | Tone depth | Tint |
|---|---|---|
| C1 | Dark chestnut-brown | Iridescent ash |
| C2 | Dark chestnut-brown | Ash-blue |
| C3 | Dark blond | Coppery golden |
| C4 | Light chestnut-brown | Iridescent mahogany |
| C5 | Dark blond | Coppery |
| C6 | Blond | Bright red |
| C7 | Blond | Bright coppery |

The colourations obtained are particularly strong and very chromatic.

The invention claimed is:

1. A composition for dyeing keratin fibers, comprising, in a cosmetically acceptable dyeing medium, at least four oxidation dye precursors, including:
   A) at least one oxidation base chosen from:
      A1) pyrazolopyridines of formula (I), pyrazolopyridines of formula (II), and the addition salts, solvates and solvates of the salts thereof:

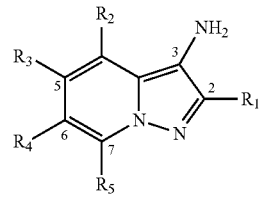

(I)

wherein:

$R_1$, $R_2$, $R_3$, $R_4$ and $R_5$, which may be identical or different, are chosen from hydrogen atoms, halogen atoms; radicals —NHSO$_3$H; hydroxyl radicals; radicals ($C_1$-$C_4$)alkyl; radicals ($C_1$-$C_4$)alkoxy; radicals ($C_1$-$C_4$)alkylthio; mono($C_1$-$C_4$)alkylamino; radicals di($C_1$-$C_4$)alkylamino wherein the two alkyl groups may form, together with the nitrogen atom to which they are attached, a ring that is optionally interrupted with at least one atom chosen from nitrogen, oxygen and sulfur atoms; heterocycles; nitro radicals; phenyl radicals; carbonyl radicals; ($C_1$-$C_4$)alkoxycarbonyl radicals; carboxamido radicals; cyano radicals; amino radicals; sulfonyl radicals; radicals —CO$_2$H, radicals —SO$_3$H; radicals —PO$_3$H$_2$; radicals —PO$_4$H$_2$; and groups

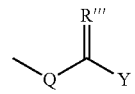

wherein R''' is chosen from oxygen and nitrogen atoms, Q is chosen from oxygen atoms, groups NH and NH($C_1$-$C_4$)alkyl, and Y is chosen from hydroxyl, amino, $C_1$-$C_4$ alkyl, ($C_1$-$C_4$) alkoxy, ($C_1$-$C_4$)alkylamino and di($C_1$-$C_4$)alkylamino radicals;

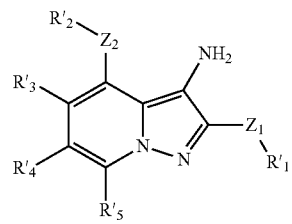

(II)

wherein:

$Z_1$ and $Z_2$, which may be identical or different, are chosen from:
   covalent single bonds;
   divalent radicals chosen from:
      radicals —O(CH$_2$)$_p$—, wherein p is an integer ranging from 0 to 6;
      radicals —NR'$_6$(CH$_2$)$_q$(C$_6$H$_4$)$_t$—, wherein q is an integer ranging from 0 to 6, t is chosen from 0 and 1, and R'$_6$ is chosen from hydrogen atoms and C$_1$-C$_6$ alkyl radicals optionally substituted with at least one hydroxyl group;

Z$_1$ may also be chosen from divalent radicals —S—, —SO— and —SO$_2$— when R'$_1$ is a methyl radical;

R'$_1$ and R'$_2$, which may be identical or different, are chosen from:
- hydrogen atoms;
- C$_1$-C$_{10}$ alkyl radicals, which are optionally substituted and optionally interrupted with a group chosen from heteroatoms, O, N, Si, S, SO and SO$_2$;
- halogen atoms;
- SO$_3$H radicals;
- 5- to 8-membered rings which are chosen from substituted and unsubstituted, saturated, unsaturated and aromatic, optionally comprising at least one heteroatom and groups chosen from N, O, S, SO$_2$ and —CO—, the ring optionally being cationic and optionally substituted with a cationic radical;
- groups —N$^+$R$_{17}$R$_{18}$R$_{19}$, wherein R$_{17}$, R$_{18}$ and R$_{19}$ are independently chosen from linear and branched C$_1$-C$_5$ alkyls optionally substituted with at least one hydroxyl group;

when Z$_1$ or, respectively, Z$_2$ is a covalent bond, then R'$_1$ or, respectively, R'$_2$ may be chosen from:
- optionally substituted C$_1$-C$_6$ alkylcarbonyl radicals; and
- —O—CO—R, —CO—O—R, NR—CO—R' and —CO—NRR', wherein R and R' independently are chosen from hydrogen atoms and optionally substituted C$_1$-C$_6$ alkyl radicals;

R'$_3$, R'$_4$ and R'$_5$ are independently chosen from:
- hydrogen atoms;
- hydroxyl radicals;
- C$_1$-C$_6$ alkoxy radicals;
- C$_1$-C$_6$ alkylthio radicals;
- amino radicals;
- monoalkylamino radicals;
- C$_1$-C$_6$ dialkylamino radicals wherein the alkyl radicals may form, with the nitrogen atom to which they are attached, a saturated, unsaturated, aromatic or non-aromatic 5- to 8-membered heterocycle, which may comprise at least one group chosen from heteroatoms, N, O, S, SO$_2$ and CO, the heterocycle optionally being cationic, and optionally substituted with a cationic radical;
- optionally substituted C$_1$-C$_6$ alkylcarbonyl radicals;
- radicals —O—CO—R, —CO—O—R, NR—CO—R' and —CO—NRR' wherein R and R' independently are chosen from hydrogen atoms and optionally substituted C$_1$-C$_6$ alkyl radicals;
- halogen atoms;
- —NHSO$_3$H radicals;
- optionally substituted C$_1$-C$_4$ alkyl radicals; and
- saturated, unsaturated and aromatic, optionally substituted carbon-based rings;

R'$_3$, R'$_4$ and R'$_5$, may form in pairs a partially saturated or unsaturated ring;

X is chosen from ions and group of ions that provide the electronegativity of the derivative of formula (II);

with the proviso that at least one of the groups R'$_1$ and R$_2$ is a cationic radical; and A2) diamino-N,N-dihydropyrazolone derivatives of formula (III), and the addition salts, solvates and solvates of the salts thereof:

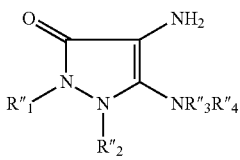

(III)

wherein:

R"$_1$, R"$_2$, R"$_3$ and R"$_4$, which may be identical or different, are chosen from:
- linear and branched C$_1$-C$_6$ alkyl radicals optionally substituted with at least one radical chosen from radicals OR"$_5$, radicals NR"$_6$R"$_7$, carboxyl radicals, sulfonic radicals, carboxamido radicals CONR"$_6$R"$_7$, sulfonamido radicals SO$_2$NR"$_6$R"$_7$, heteroaryls, aryls optionally substituted with at least one group chosen from (C$_1$-C$_4$)alkyl, hydroxyl, C$_1$-C$_2$ alkoxy, amino and (di)alkyl(C$_1$-C$_2$)amino groups;
- aryl radicals optionally substituted with at least one group chosen from (C$_1$-C$_4$)alkyl, hydroxyl, C$_1$-C$_2$ alkoxy, amino and (di)alkyl(C$_1$-C$_2$)amino groups;
- 5- and 6-membered heteroaryl radicals, optionally substituted with at least one radical chosen from (C$_1$-C$_4$)alkyl and (C$_1$-C$_2$)alkoxy;

R"$_3$ and R"$_4$ may also independently be chosen from hydrogen atoms;

R"$_5$, R"$_6$ and R"$_7$ independently are chosen from:
- hydrogen atoms;
- linear and branched C$_1$-C$_4$ alkyl radicals optionally substituted with at least one radical chosen from hydroxyl radicals, C$_1$-C$_2$ alkoxy radicals, carboxamido radicals CONR"$_8$R"$_9$, sulfonyl radicals SO$_2$R"$_8$, and aryl radicals optionally substituted with a group chosen from (C$_1$-C$_4$)alkyl, hydroxyl, C$_1$-C$_2$ alkoxy, amino and (di)alkyl(C$_1$-C$_2$)amino groups;

R"$_6$ and R"$_7$, may also independently be chosen from carboxamido radicals CONR"$_8$R"$_9$ and sulfonyl radicals SO$_2$R"$_8$;

R"$_8$ and R"$_9$ are independently chosen from hydrogen atoms; linear and branched C$_1$-C$_4$ alkyl radicals optionally substituted with at least one radicals chosen from hydroxyl and C$_1$-C$_2$ alkoxy radicals;

R"$_1$ and R"$_2$ and R"$_3$ and R"$_4$ may form, with the nitrogen atoms to which they are attached, a saturated or unsaturated 5- to 7-membered heterocycle optionally substituted with at least one radical chosen from halogen atoms, amino radicals, (di)alkyl(C$_1$-C$_4$)amino radicals, hydroxyl radicals, carboxyl radicals, carboxamido radicals, (C$_1$-C$_2$)alkoxy radicals, and C$_1$-C$_4$ alkyl radicals optionally substituted with at least one radicals chosen from hydroxyl, amino, (di)alkylamino, alkoxy, carboxyl and sulfonyl radicals;

R"$_3$ and R"$_4$ may also form, together with the nitrogen atom to which they are attached, a 5- or 7-membered heterocycle wherein the carbon atoms may be replaced with an optionally substituted atom chosen from oxygen and nitrogen atoms;

and

B) at least one coupler chosen from:

B1) derivatives of cationic aminopyridines of formula (IV) and the addition salts, solvates and solvates of the salts thereof:

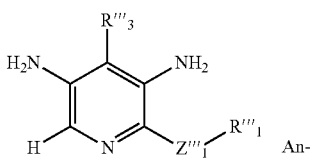

(IV)

wherein the group $Z'''_1R'''_1$ bears a cationic charge;
$Z'''_1$ is chosen from oxygen atoms and $NR'''_2$ groups;
$R'''_2$ is chosen from hydrogen atoms, linear and branched $C_1$-$C_4$ alkyl radicals, benzyl radicals, and acetyl radicals;
$R'''_1$ is chosen from
  saturated, linear and branched $C_1$-$C_{10}$ alkyl radicals, optionally substituted and optionally interrupted with a cationic radical, optionally interrupted with at least one oxygen atom and with at least one group $NR'''_2$, optionally substituted with at least one radical chosen from hydroxyl, alkoxy and $C_1$-$C_4$ hydroxyalkyl radicals; and
  $R'''_1$ is chosen from saturated, and saturated and aromatic 5- to 8-membered heterocycles optionally substituted with at least one radical chosen from $C_1$-$C_4$ alkyl, hydroxyl, $C_1$-$C_4$ alkoxy, amino, $(C_1$-$C_4)$alkylamino, di$(C_1$-$C_4)$alkylamino, thio, $(C_1$-$C_4)$alkylthio, carboxyl, $(C_1$-$C_4)$alkylcarbonyl, sulfonyl, amido and $C_1$-$C_4$ hydroxyalkyl radicals;
provided that when $Z'''_1$ is $NR'''_2$, then
  $R'''_1$ and $R'''_2$ may form, together with the nitrogen atom to which they are attached, a cationic, saturated or unsaturated 5- to 8-membered heterocycle, optionally substituted with at least one radical chosen from $C_1$-$C_{10}$ alkyl radicals, hydroxyl, $C_1$-$C_4$ alkoxy, amino, $(C_1$-$C_4)$alkylamino, di$(C_1$-$C_4)$alkylamino, thio, $(C_1$-$C_4)$alkylthio, carboxyl, $(C_1$-$C_4)$alkylcarbonyl, sulfonyl, amido and $C_1$-$C_4$ hydroxyalkyl radicals, wherein the heterocycle optionally comprises at least one heteroatom chosen from N and O; and
  $R'''_1$ and $R'''_2$ may form, together with the nitrogen atom to which they are attached, a non-cationic, saturated or unsaturated 5- to 8-membered heterocycle, substituted with a cationic radical and optionally substituted with at least one radical chosen from $C_1$-$C_{10}$ alkyl radicals, hydroxyl, $C_1$-$C_4$ alkoxy, amino, $(C_1$-$C_4)$alkylamino, di$(C_1$-$C_4)$alkylamino, thio, $(C_1$-$C_4)$alkylthio, carboxyl, $(C_1$-$C_4)$alkylcarbonyl, sulfonyl, amido and $C_1$-$C_4$ hydroxyalkyl radicals;
$R'''_3$ is chosen from hydrogen atoms, halogens chosen from fluorine, chlorine and bromine, linear and branched $C_1$-$C_4$ alkyl radicals, carboxyl (—COOH) and $(C_1$-$C_4)$alkoxycarbonyl radicals;
An- is chosen from at least one anion;
  B2) 4-aminoindole derivatives of formula (V), and addition salts, solvates and solvates of the salts thereof:

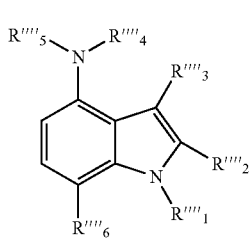

(V)

wherein:
$R''''_1$ is chosen from:
  hydrogen atoms; and
  linear and branched, saturated $C_1$-$C_6$ alkyl radicals, optionally interrupted with an group chosen from oxygen atoms and radicals $NR''''_7$, optionally substituted with a radical chosen from OH and $NR''''_7R''''_8$;
$R''''_2$ and $R''''_3$ independently are chosen from:
  hydrogen atoms;
  $C_1$-$C_6$ alkyl radicals, optionally substituted with at least one hydroxyl radical;
  $C_1$-$C_6$ alkyl carboxylate radicals;
  carboxyl radicals; and
  radicals $CONR''''_7R''''_8$;
$R''''_4$ and $R''''_5$ independently are chosen from:
  hydrogen atoms; and
  $C_1$-$C_6$ alkyl radicals;
$R''''_6$ is chosen from:
  halogen atoms;
  linear and branched $C_1$-$C_{10}$ alkyl radicals, optionally interrupted with a heteroatom chosen from O and $NR''''_9$, and optionally substituted with at least one radical, which may be identical or different, chosen from OH and $NR''''_7R''''_8$;
  carboxyl radicals;
  $C_1$-$C_{10}$ alkyl carboxylate radicals;
  radicals $CONR''_7R''_8$;
  $C_1$-$C_{10}$ alkoxy radicals and $C_1$-$C_{10}$ (poly)hydroxyalkoxy radicals;
  (poly)$(C_1$-$C_{10})$alkoxy$(C_1$-$C_{10})$alkyloxy radicals; and
  radicals O-Ak-$NR''''_9R''''_{10}$ wherein Ak is chosen from linear $C_1$-$C_8$ and branched $C_3$-$C_8$ divalent alkylene radicals, optionally interrupted with at least one group chosen from oxygen atom and groups $NR''''_7$;
$R''''_7$ and $R''''_8$, which may be identical or different, are chosen from:
  hydrogen atoms;
  $C_1$-$C_8$ alkyl radicals optionally substituted with at least one hydroxyl radical;
$R''''_9$ and $R''''_{10}$, which may be identical or different, are chosen from linear and branched, saturated and unsaturated $C_1$-$C_4$ alkyl radicals;
$R''''_9$ and $R''''_{10}$ may form, with the nitrogen that bears them, a saturated or unsaturated 5- to 8-membered heterocycle, one of the chain members optionally being chosen from oxygen atoms and radicals $NR''''_{11}$ wherein $R''''_{11}$ is chosen from hydrogen atoms and $C_1$-$C_4$ alkyl radicals, optionally substituted with at least one radical chosen from OH and $NR''''_7R''''_8$;
  B3) 5-amino-6-chloro-2-methylphenol of formula (VI), and addition salts, solvates and solvates of the salts thereof:

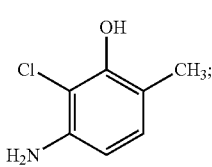

(VI)

B4) 6-hydroxybenzomorpholine of formula (VII), and addition salts, solvates and solvates of the salts thereof:

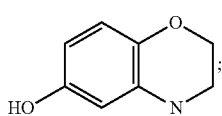
(VII)

B5) 2-methyl-5-hydroxyethylaminophenol of formula (VIII), and addition salts, solvates and solvates of the salts thereof:

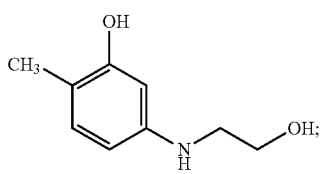
(VIII)

and

B6) 2-amino-3-hydroxypyridine of formula (IX), and addition salts, solvates and solvates of the salts thereof:

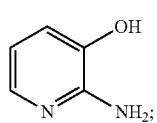
(IX)

and

C) a basifying agent chosen from monoethanolamine.

2. The composition according to claim 1, wherein the compounds of formula (I) are chosen from the compounds of the formula:

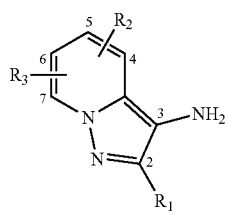

wherein:

$R_1$, $R_2$ and $R_3$ independently are chosen from hydrogen atoms; halogen atoms; hydroxyl radicals; ($C_1$-$C_4$)alkyl radicals; ($C_1$-$C_4$)alkylthio radicals; ($C_1$-$C_4$)alkoxy radicals; —NHSO$_3$H radicals; amino radicals; ($C_1$-$C_4$)alkylamino radicals; di($C_1$-$C_4$)alkylamino radicals wherein the two alkyl groups may form, together with the nitrogen atom to which they are attached, a ring that is optionally interrupted with at least one atom chosen from nitrogen, oxygen and sulfur atoms; heterocycles; sulfonamide radicals, carbonyl radicals, ($C_1$-$C_4$)alkoxycarbonyl radicals, carboxamido radicals, and groups of the formula:

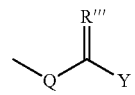

wherein R''' is chosen from oxygen and nitrogen atoms, Q is chosen from oxygen atoms, groups NH and NH($C_1$-$C_4$)alkyl groups, and Y is chosen from hydroxyl, amino, $C_1$-$C_4$ alkyl, ($C_1$-$C_4$)alkoxy, ($C_1$-$C_4$)alkylamino and di($C_1$-$C_4$)alkylamino radicals.

3. The composition according to claim 1, wherein the 3-aminopyrazolo[1,5-a]pyridines of formula (I) are chosen from:
pyrazolo[1,5-a]pyridin-3-ylamine;
2-acetylaminopyrazolo[1,5-a]pyridin-3-ylamine;
2-morpholin-4-ylpyrazolo[1,5-a]pyridin-3-ylamine;
3-aminopyrazolo[1,5-a]pyridine-2-carboxylic acid;
2-methoxypyrazolo[1,5-a]pyridin-3-ylamino;
(3-aminopyrazolo[1,5-a]pyridin-7-yl)methanol;
2-(3-aminopyrazolo[1,5-a]pyridin-5-yl)ethanol;
2-(3-aminopyrazolo[1,5-a]pyridin-7-yl)ethanol;
(3-aminopyrazolo[1,5-a]pyridin-2-yl)methanol;
3,6-diaminopyrazolo[1,5-a]pyridine;
3,4-diaminopyrazolo[1,5-a]pyridine;
pyrazolo[1,5-a]pyridine-3,7-diamine;
7-morpholin-4-ylpyrazolo[1,5-a]pyridin-3-ylamine;
pyrazolo[1,5-a]pyridine-3,5-diamine;
5-morpholin-4-ylpyrazolo[1,5-a]pyridin-3-ylamine;
2-[(3-aminopyrazolo[1,5-a]pyridin-5-yl)(2-hydroxyethyl)amino]ethanol;
2-[(3-aminopyrazolo[1,5-a]pyridin-7-yl)(2-hydroxyethyl)amino]ethanol;
3-aminopyrazolo[1,5-a]pyridin-5-ol;
3-aminopyrazolo[1,5-a]pyridin-4-ol;
3-aminopyrazolo[1,5-a]pyridin-6-ol;
3-aminopyrazolo[1,5-a]pyridin-7-ol;
2-methoxy-6,7-dimethylpyrazolo[1,5-a]pyridin-3-amine;
2-[(3-aminopyrazolo[1,5-a]pyridin-2-yl)oxy]ethanol;
4-ethyl-2-methoxy-7-methylpyrazolo[1,5-a]pyridin-3-amine hydrochloride;
1-(3-aminopyrazolo[1,5-a]pyridin-2-yl)pyrrolidin-3-ol;
2,2'-[(3-aminopyrazolo[1,5-a]pyridin-2-yl)imino]diethanol;
2-[(3-aminopyrazolo[1,5-a]pyridin-2-yl)amino]ethanol;
N2-(2-pyridin-3-ylethyl)pyrazolo[1,5-a]pyridine-2,3-diamine;
and addition salts, solvates and solvates of the salts thereof.

4. The composition according to claim 1, wherein the compound of formula (II) is:

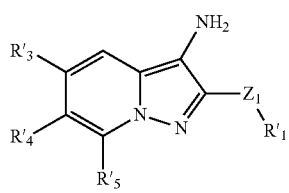

wherein $Z_1$ is chosen from:
covalent single bonds;
divalent radicals chosen from:
radicals —O(CH$_2$)$_p$—, wherein p is an integer ranging from 0 to 6;

radicals —NR'₆(CH₂)_q(C₆H₄)_t—, wherein q is an integer ranging from 0 to 6, t is chosen from 0 and 1, and R'₆ is chosen from hydrogen atoms and $C_1$-$C_6$ alkyl radicals optionally substituted with at least one hydroxyl group; and —S—, —SO— and —SO₂— when R'₁ is a methyl radical;

R'₁ is chosen from hydrogen atoms;

$C_1$-$C_{10}$ alkyl radicals, which are optionally substituted and optionally interrupted with a group chosen from heteroatoms, O, N, Si, S, SO and SO₂;

halogen atoms;

SO₃H radicals;

5- to 8-membered rings which are chosen from substituted and unsubstituted, saturated, unsaturated and aromatic, optionally comprising at least one heteroatom and groups chosen from N, O, S, SO₂ and —CO—, the ring optionally being cationic and optionally substituted with a cationic radical;

groups —N⁺R₁₇R₁₈R₁₉, wherein R₁₇, R₁₈ and R₁₉ are independently chosen from linear and branched $C_1$-$C_5$ alkyls optionally substituted with at least one hydroxyl group;

when Z₁ is a covalent bond, then R'₁ may be chosen from:

optionally substituted $C_1$-$C_6$ alkylcarbonyl radicals; and

—O—CO—R, —CO—O—R, NR—CO—R' and —CO—NRR', wherein R and R' independently are chosen from hydrogen atoms and optionally substituted $C_1$-$C_6$ alkyl radicals;

R'₃, R'₄ and R'₅ independently are chosen from:

hydrogen atoms;

hydroxyl radicals;

$C_1$-$C_6$ alkoxy radicals;

$C_1$-$C_6$ alkylthio radicals;

amino radicals;

monoalkylamino radicals;

$C_1$-$C_6$ dialkylamino radicals wherein the alkyl radicals may form, with the nitrogen atom to which they are attached, a saturated, unsaturated, aromatic or non-aromatic 5- to 8-membered heterocycle, which may comprise at least one group chosen from heteroatoms, N, O, S, SO₂ and CO, the heterocycle optionally being cationic, and optionally substituted with a cationic radical;

optionally substituted $C_1$-$C_6$ alkylcarbonyl radicals;

radicals —O—CO—R, —CO—O—R, NR—CO—R' and —CO—NRR' wherein R and R' independently are chosen from hydrogen atoms and optionally substituted $C_1$-$C_6$ alkyl radicals;

halogen atoms;

—NHSO₃H radicals;

optionally substituted $C_1$-$C_4$ alkyl radicals; and saturated, unsaturated and aromatic, optionally substituted carbon-based rings;

R'₃, R'₄ and R'₅, may form in pairs a partially saturated or unsaturated ring.

5. The composition according to claim 1, wherein the pyrazolopyridines of formula (II) are chosen from:

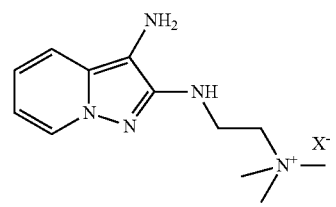

salt of [2-(3-aminopyrazolo[1,5-a]pyridin-2-ylamino)ethyl]trimethylammonium

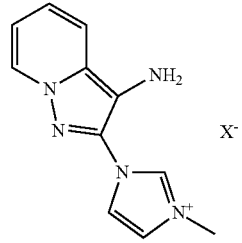

salt of 3-(3-aminopyrazolo[1,5-a]pyridin-2-yl)-1-methyl-3H-imidazol-1-ium

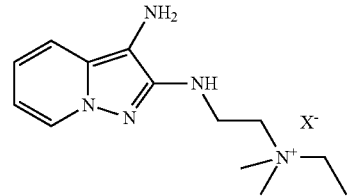

salt of [2-(3-aminopyrazolo[1,5-a]pyridin-2-ylamino)ethyl]ethyldimethylammonium

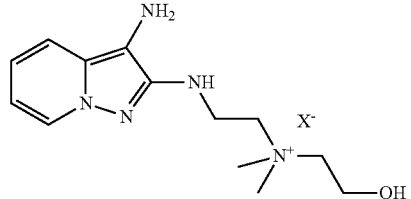

salt of [2-(3-aminopyrazolo[1,5-a]pyridin-2-ylamino)ethyl](2-hydroxyethyl)dimethylammonium

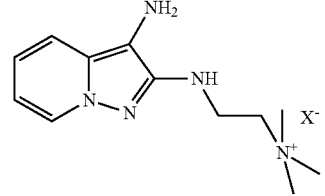

salt of [3-(3-aminopyrazolo[1,5-a]pyridin-2-ylamino)propyl]trimethylammonium

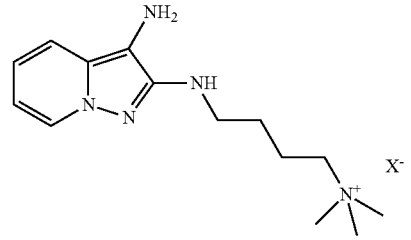

salt of [4-(3-aminopyrazolo[1,5-a]pyridin-2-ylamino)butyl]trimethylammonium

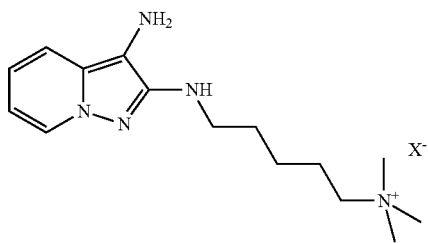

salt of [5-(3-aminopyrazolo[1,5-a]pyridin-2-ylamino)pentyl]trimethylammonium

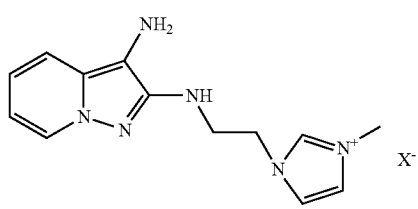

salt of 3-[2-(3-aminopyrazolo[1,5-a]pyridin-2-ylamino)ethyl-1-methyl-3H-imidazol-1-ium

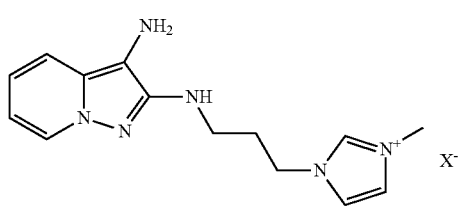

salt of 3-[3-(3-aminopyrazolo[1,5-a]pyridin-2-ylamino)propyl]-1-methyl-3H-imidazol-1-ium

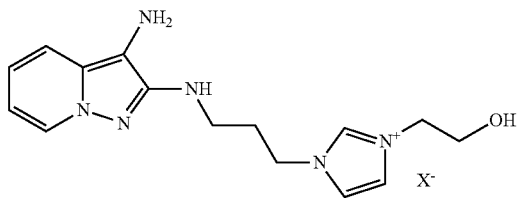

salt of 3-[3-(3-aminopyrazolo[1,5-a]pyridin-2-ylamino)propyl]-1-(2-hydroxyethyl)-3-H-imidazol-1-ium

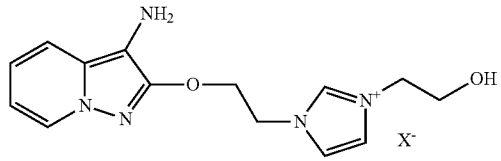

salt of 3-[2-(3-aminopyrazolo[1,5-a]pyridin-2-yloxy)ethyl]-1-(2-hydroxyethyl-3H-imidazol-1-ium

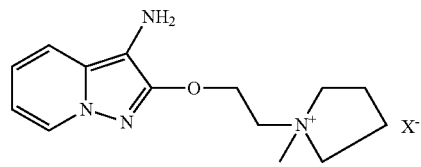

salt of 1-{2-[(3-aminopyrazolo[1,5-a]pyridin-2-yl)oxy]ethyl}-1-methylpyrrolidinium

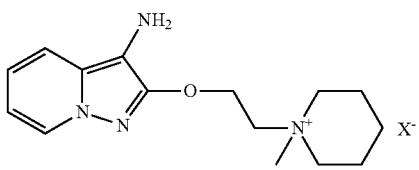

salt of 1-{2-[(3-aminopyrazolo[1,5-a]pyridin-2-yl)oxy]ethyl}-1-methylpiperidinium

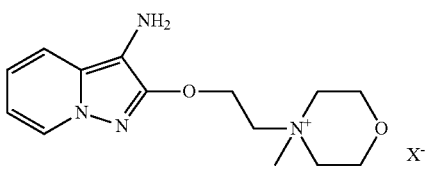

salt of 4-{2-[(3-aminopyrazolo[1,5-a]pyridin-2-yl)oxy]ethyl}-4-methylmorpholin-4-ium

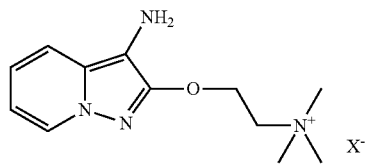

salt of {2-[(3-aminopyrazolo[1,5-a]pyridin-2-yl)oxy]ethyl}trimethylammonium

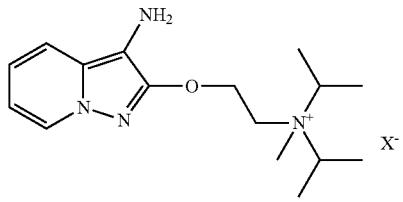

salt of {2-[(3-aminopyrazolo[1,5-a]pyridin-2-yl)oxy]ethyl}diisopropylmethylammonium

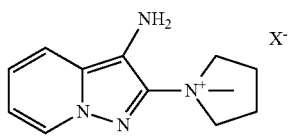

salt of 1-(3-aminopyrazolo[1,5-a]pyridin-2-yl)-1-methylpyrrolidinium

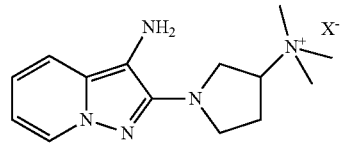

salt of [1-(3-aminopyrazolo[1,5-a]pyridin-2-yl)pyrrolidin-3-yl]trimethylammonium

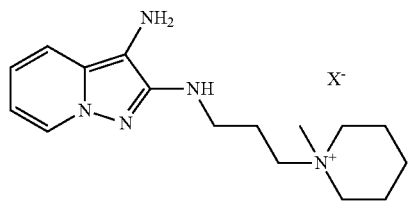

salt of 1-[3-(3-aminopyrazolo[1,5-a]pyridin-2-ylamino)propyl]-1-methylpiperidinium

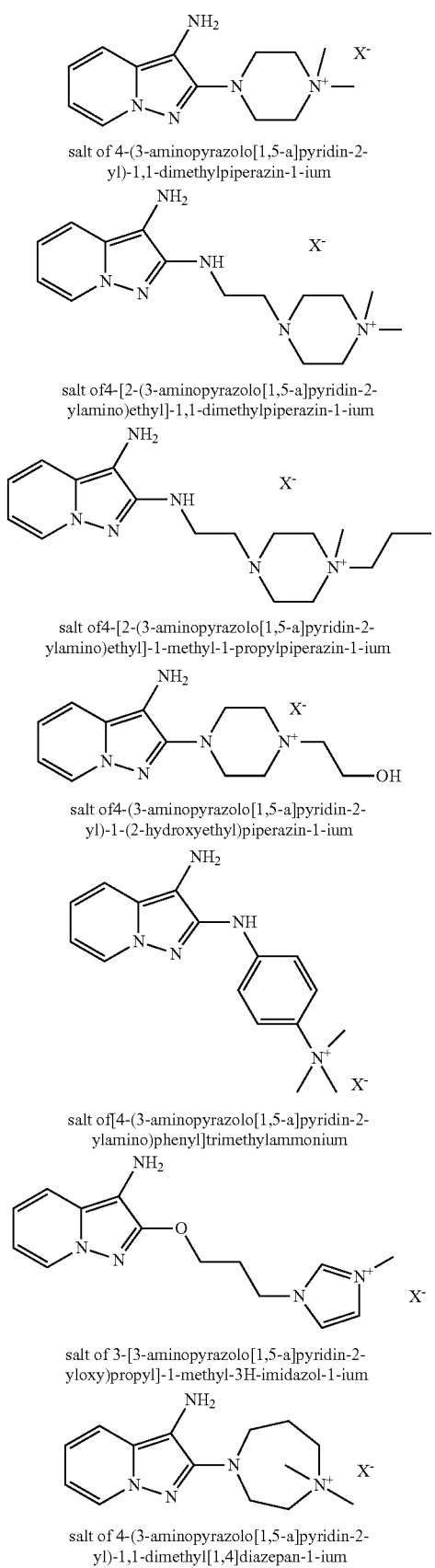

salt of 4-(3-aminopyrazolo[1,5-a]pyridin-2-yl)-1,1-dimethylpiperazin-1-ium salt of 4-[2-(3-aminopyrazolo[1,5-a]pyridin-2-ylamino)ethyl]-1,1-dimethylpiperazin-1-ium salt of 4-[2-(3-aminopyrazolo[1,5-a]pyridin-2-ylamino)ethyl]-1-methyl-1-propylpiperazin-1-ium salt of 4-(3-aminopyrazolo[1,5-a]pyridin-2-yl)-1-(2-hydroxyethyl)piperazin-1-ium salt of [4-(3-aminopyrazolo[1,5-a]pyridin-2-ylamino)phenyl]trimethylammonium salt of 3-[3-aminopyrazolo[1,5-a]pyridin-2-yloxy)propyl]-1-methyl-3H-imidazol-1-ium salt of 4-(3-aminopyrazolo[1,5-a]pyridin-2-yl)-1,1-dimethyl[1,4]diazepan-1-ium

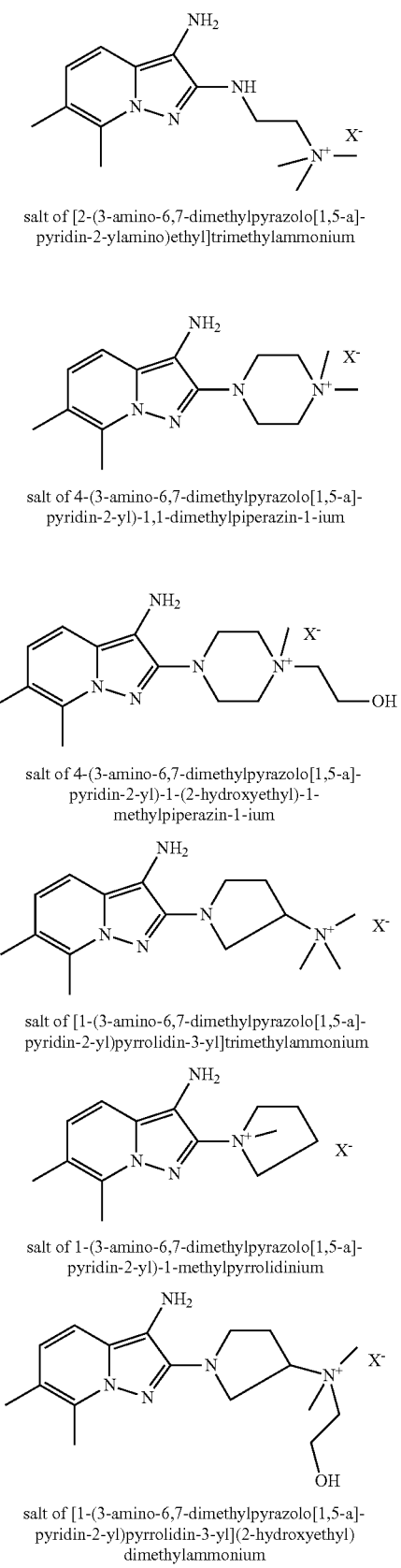

salt of [2-(3-amino-6,7-dimethylpyrazolo[1,5-a]-pyridin-2-ylamino)ethyl]trimethylammonium salt of 4-(3-amino-6,7-dimethylpyrazolo[1,5-a]-pyridin-2-yl)-1,1-dimethylpiperazin-1-ium salt of 4-(3-amino-6,7-dimethylpyrazolo[1,5-a]-pyridin-2-yl)-1-(2-hydroxyethyl)-1-methylpiperazin-1-ium salt of [1-(3-amino-6,7-dimethylpyrazolo[1,5-a]-pyridin-2-yl)pyrrolidin-3-yl]trimethylammonium salt of 1-(3-amino-6,7-dimethylpyrazolo[1,5-a]-pyridin-2-yl)-1-methylpyrrolidinium salt of [1-(3-amino-6,7-dimethylpyrazolo[1,5-a]-pyridin-2-yl)pyrrolidin-3-yl](2-hydroxyethyl)dimethylammonium

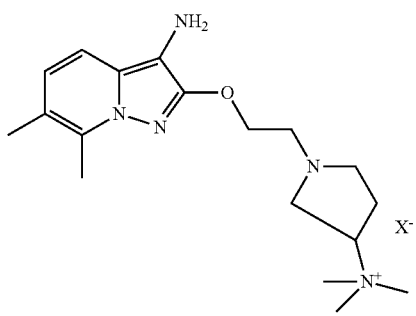

salt of {1-[2-(3-amino-6,7-dimethylpyrazolo[1,5-a]-pyridin-2-yloxy)ethyl]pyrrolidin-3-yl} trimethylammonium

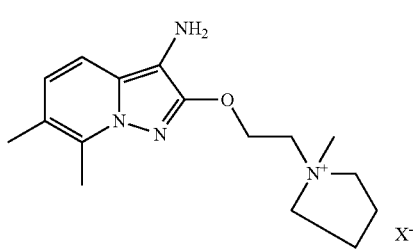

salt of 1{2-[(3-amino-6,7-dimethylpyrazolo[1,5-a] pyridin-2-yl)oxy]ethyl}-1-methylpyrrolidinium

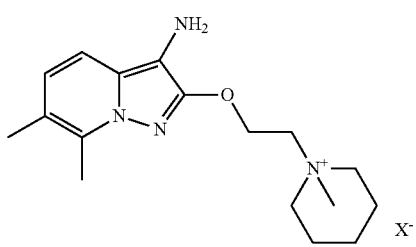

salt of 1{2-[(3-amino-6,7-dimethylpyrazolo[1,5-a]-pyridin-2-yl)oxy]ethyl}-1-methylpiperidinium

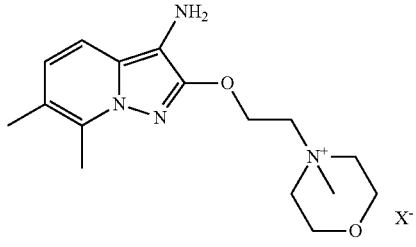

salt of 4-{2-[(3-amino-6,7-dimethylpyrazolo[1,5-a]-pyridin-2-yl)oxy]ethyl}-4-methylmorpholin-4-ium

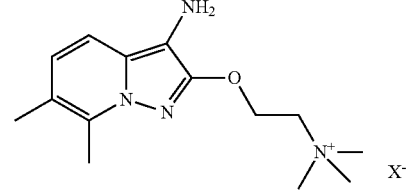

salt of {2-[(3-amino-6,7-dimethylpyrazolo[1,5-a]-pyridin-2-yl)oxy]ethyl}trimethylammonium

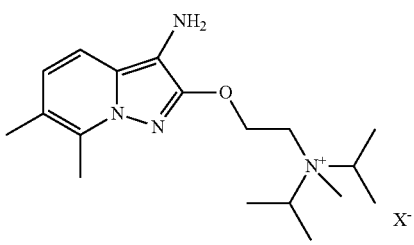

salt of {2-[(3-amino-6,7-dimethylpyrazolo[1,5-a]-pyridin-2-yl)oxy]ethyl}diisopropylmethylammonium

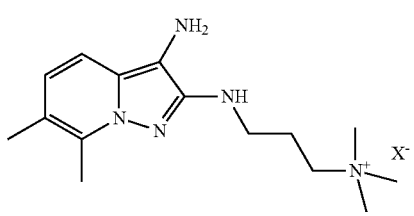

salt of [3-(3-amino-6,7-dimethylpyrazolo[1,5-a]-pyridin-2-ylamino)propyl]trimethylammonium

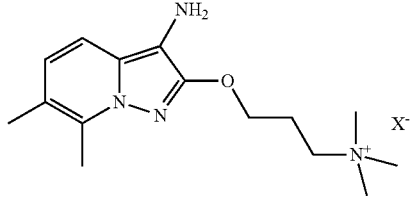

salt of [3-(3-amino-6,7-dimethylpyrazolo[1,5-a]-pyridin-2-yloxy)propyl]trimethylamonium

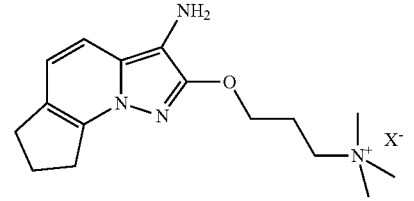

salt of [3-(3-amino-7,8-dihydro-6H-cyclopenta[e] pyrazolo[1,5-a]-pyridin-2-yloxy)propyl] trimethylammonium

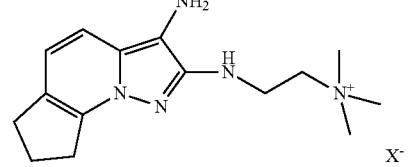

salt of {2-[(3-amino-7,8-dihydro-6H-cyclopenta[e] pyrazolo[1,5-a]-pyridin-2-yl)amino] ethyl}trimethylammonium

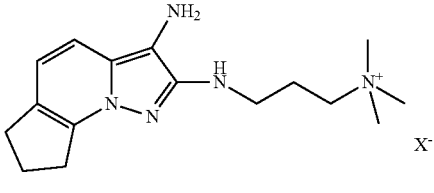

salt of {3-[(3-amino-7,8-dihydro-6H-cyclopenta[e] pyrazolo[1,5-a]-pyridin-2-yl)amino] propyl}trimethylammonium

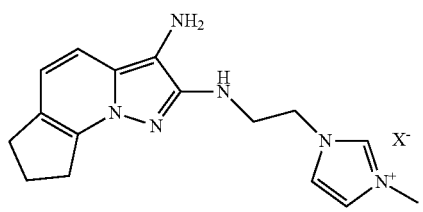

salt of 1-{2-[(3-amino-7,8-dihydro-6H-cyclopenta[e]
pyrazolo[1,5-a]-pyridin-2-yl)amino]ethyl}-
3-methyl-1H-imidazol-3-ium

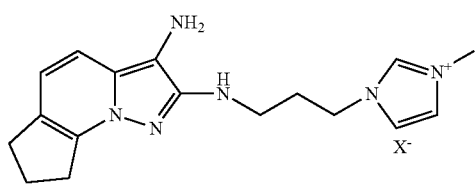

salt of 1-{3-[(3-amino-7,8-dihydro-6H-cyclopenta[e]
pyrazolo[1,5-a]-pyridin-2-yl)amino]
propyl}-3-methyl-1H-imidazol-3-ium

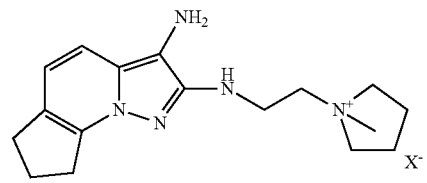

salt of 1-{2-[(3-amino-7,8-dihydro-6H-cyclopenta[e]
pyrazolo[1,5-a]-pyridin-2-yl)amino]
ethyl}-1-methylpyrrolidinium

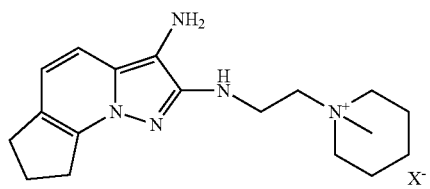

salt of 1-{2-[(3-amino-7,8-dihydro-6H-cyclopenta[e]
pyrazolo[1,5-a]-pyridin-2-yl)amino]
ethyl}-1-methylpiperidinium

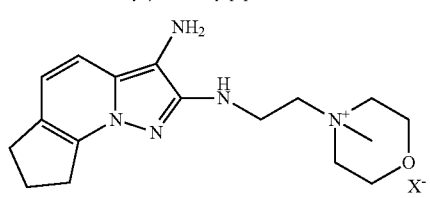

salt of 4-{2-[(3-amino-7,8-dihydro-6H-cyclopenta[e]
pyrazolo[1,5-a]-pyridin-2-yl)amino]
ethyl}-4-methylmorpholin-4-ium

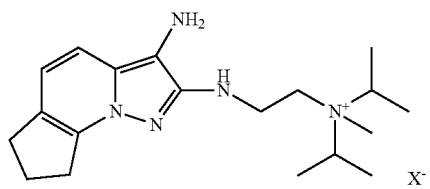

salt of {2-[(3-amino-7,8-dihydro-6H-cyclopenta[e]
pyrazolo[1,5-a]-pyridin-2-yl)amino]
ethyl}diisopropylmethylammonium

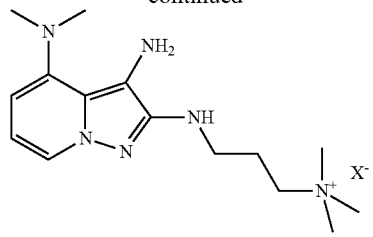

salt of [3-(3-amino-4-dimethylaminopyrazolo
[1,5-a]-pyridin-2-ylamino)propyl]
trimethylammonium

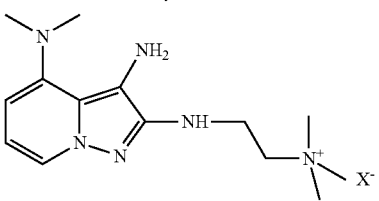

salt of [2-(3-amino-4-dimethylaminopyrazolo
[1,5-a]-pyridin-2-ylamino)ethyl]
trimethylammonium

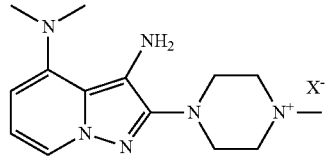

salt of 4-(3-amino-4-dimethylaminopyrazolo
[1,5-a]-pyridin-2-yl)-1-methylpiperazin-1-ium

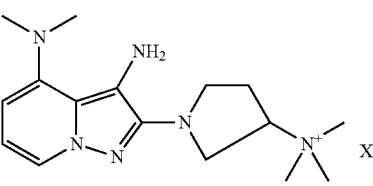

salt of [1-(3-amino-4-dimethylaminopyrazolo
[1,5-a]-pyridin-2-yl)pyrrolidin-3-yl]
trimethylammonium

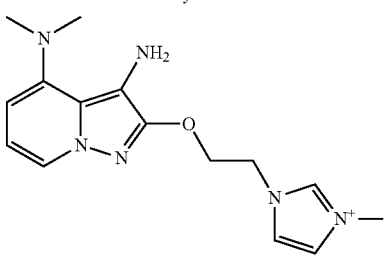

salt of 3-[2-(3-amino-4-dimethylaminopyrazolo
[1,5-a]-pyridin-2-yloxy)ethyl]-1-methyl-3H-
imidazol-1-ium

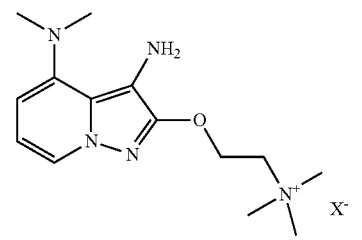

salt of [2(3-amino-4-dimethylaminopyrazolo
[1,5-a]-pyridin-2-yloxy)ethyl]
trimethylammonium -continued

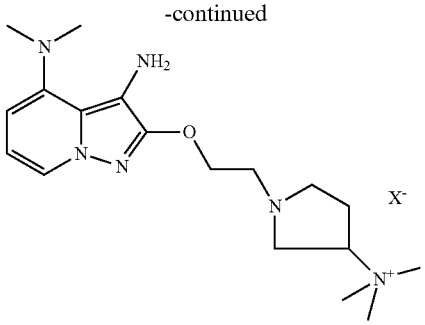

salt of {1-[2(3-amino-4-dimethylaminopyrazolo
[1,5-a]-pyridin-2-yloxy)ethyl]pyrrolidin-3-yl}
trimethylammonium

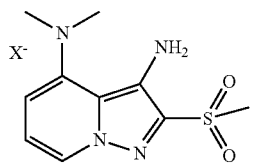

salt of (3-amino-2-methanesulfonylpyrazolo
[1,5-a]-pyridin-4-yl)trimethylammonium

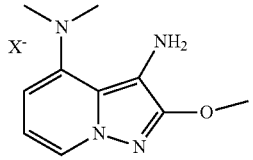

salt of (3-amino-2-methoxy-pyrazolo
[1,5-a]pyridin-4-yl)trimethylammonium and the addition salts thereof, solvates thereof or solvates of the salts thereof, and wherein X is chosen from ions and group of ions that provide the electronegativity of the derivative of formula (II).

6. The composition according to claim 1, wherein the pyrazolopyridines of formulae (I) and (II) are chosen from:

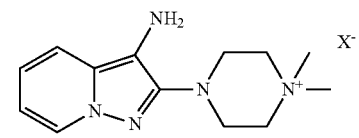

salt of 4-(3-amino-pyrazolo[1,5-a]pyridin-2-
yl)-1,1-dimethyl-piperazin-1-ium

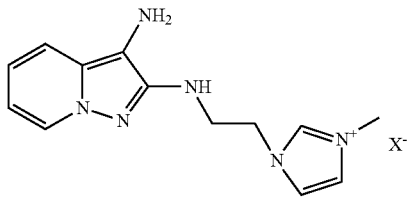

Salt of 3-[2-(3-amino-pyrazolo[1,5-a]pyridin-2-
ylamino)ethyl]-1-methyl-3H-imidazol-1-ium, and 2-[(3-aminopyrazolo[1,5-a]pyridin-2-yl)oxy]ethanol, and addition salts, solvates and solvates of the salts thereof, and wherein X is chosen from ions and group of ions that provide the electronegativity of the derivative of the formula.

7. The composition according to claim 1, wherein $R''_1$ and $R''_2$ are independently chosen from $C_1$-$C_6$ alkyl radicals optionally substituted with a radical chosen from hydroxyl radicals, ($C_1$-$C_2$)alkoxy radicals, amino radicals, (di)($C_1$-$C_2$) alkylamino radicals; phenyl radical radicals, methoxyphenyl radicals, ethoxyphenyl radicals, and benzyl radicals.

8. The composition according to claim 1, wherein $R''_1$ and $R''_2$ form, together with the nitrogen atoms to which they are attached, an optionally substituted saturated or unsaturated 5- or 6-membered ring, optionally substituted with at least one radical chosen from $C_1$-$C_4$ alkyl, hydroxyl, ($C_1$-$C_2$)alkoxy, carboxyl, carboxamido, amino and (di)($C_1$-$C_2$)alkylamino radicals.

9. The composition according to claim 1, wherein $R''_3$ and $R''_4$ are independently chosen from hydrogen atoms; linear and branched $C_1$-$C_6$ alkyl radicals optionally substituted with at least one radical chosen from hydroxyl, ($C_1$-$C_2$)alkoxy, amino and (di)($C_1$-$C_2$)alkylamino radicals; and phenyl radicals optionally substituted with at least one radical chosen from hydroxyl, amino and ($C_1$-$C_2$)alkoxy radicals.

10. The composition according to claim 1, wherein $R''_3$ and $R''_4$ form, together with the nitrogen atom to which they are attached, a 5- or 7-membered ring chosen from pyrrolidine, 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-aminopyrrolidine, 3-methylaminopyrrolidine, 3-dimethylaminopyrrolidine, 4-amino-3-hydroxypyrrolidine, 3-hydroxy-4-(2-hydroxyethyl)aminopyrrolidine, piperidine, 2,6-dimethylpiperidine, 2-carboxypiperidine, 2-carboxamidopiperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamidohomopiperidine, homopiperazine, N-methylhomopiperazine and N-(2-hydroxyethyl)homopiperazine.

11. The composition according to claim 1, wherein the diamino-N,N-dihydropyrazolone derivatives of formula (III) are chosen from:
 2,3-diamino-6,7-dihydro-1H,5H-pyrazolo[1,2-a]pyrazol-1-one;
 2-amino-3-ethylamino-6,7-dihydro-1H,5H-pyrazolo[1,2-a]pyrazol-1-one;
 2-amino-3-isopropylamino-6,7-dihydro-1H,5H-pyrazolo[1,2-a]pyrazol-1-one;
 2-amino-3-(pyrrolidin-1-yl)-6,7-dihydro-1H,5H-pyrazolo[1,2-a]pyrazol-1-one;
 4,5-diamino-1,2-dimethyl-1,2-dihydropyrazol-3-one;
 4,5-diamino-1,2-diethyl-1,2-dihydropyrazol-3-one;
 4,5-diamino-1,2-bis(2-hydroxyethyl)-1,2-dihydropyrazol-3-one;
 2-amino-3-(2-hydroxyethyl)amino-6,7-dihydro-1H,5H-pyrazolo[1,2-a]pyrazol-1-one;
 2-amino-3-dimethylamino-6,7-dihydro-1H,5H-pyrazolo[1,2-a]pyrazol-1-one;
 2,3-diamino-5,6,7,8-tetrahydro-1H,6H-pyridazino[1,2-a]pyrazol-1-one;
 4-amino-1,2-diethyl-5-(pyrrolidin-1-yl)-1,2-dihydropyrazol-3-one;
 4-amino-5-(3-dimethylaminopyrrolidin-1-yl)-1,2-diethyl-1,2-dihydropyrazol-3-one;
 2,3-diamino-6-hydroxy-6,7-dihydro-1H,5H-pyrazolo[1,2-a]pyrazol-1-one;
 and addition salts, solvates and solvates of the salts thereof.

12. The composition according to claim 1, wherein, in formula (IV), the cationic radical is chosen from linear and branched, cyclic, saturated and unsaturated radicals, comprising a quaternary ammonium of —N⁺RaRbRc, wherein Ra, Rb and Rc independently are chosen from $C_1$-$C_6$ alkyl radicals optionally substituted with a hydroxyl, and Ra and Rb optionally together form a 5- to 8-membered heterocycle, and when Ra and Rb together form a 5- to 8-membered heterocycle, the radical Rc is a $C_1$-$C_6$ alkyl radical optionally substituted with a hydroxyl.

13. The composition according to claim 1, wherein $R'''_1$ is chosen from $C_1$-$C_8$ alkyl radicals substituted or interrupted with a cationic radical, optionally interrupted with at least one oxygen atom and optionally interrupted with at least one group $NR'''_2$, optionally substituted with a hydroxyl radical.

14. The composition according to claim 1, wherein $Z'''_1$ is chosen from oxygen atoms and $NR'''_2$ wherein $R'''_2$ is chosen from hydrogen atoms and linear and branched $C_1$-$C_4$ alkyl radicals, and $R'''_1$ is chosen from saturated linear $C_2$-$C_8$ alkyl radicals, optionally interrupted with an oxygen atom and optionally interrupted with an NH group, optionally substituted with a hydroxyl radical, and substituted or interrupted with a cationic radical chosen from trimethylammonium, imidazolium, piperazinium, piperidinium, pyrrolidinium and morpholinium radicals.

15. The composition according to claim 1, wherein $Z'''_1$ is a group $NR'''_2$ and $R'''_1$ and $R'''_2$ form, together with the nitrogen atom to which they are attached, a saturated or unsaturated, 5- to 8-membered cationic heterocycle, optionally substituted with at least one radical chosen from $C_1$-$C_{10}$ alkyl radicals and $C_1$-$C_{10}$ hydroxyalkyl radicals.

16. The composition according to claim 1, wherein $Z'''_1$ is a group $NR'''_2$ and $R'''_1$ and $R'''_2$ form, together with the nitrogen atom to which they are attached, a saturated or unsaturated, 5- to 8-membered non-cationic heterocycle, substituted with a cationic radical.

17. The composition according to claim 1, wherein the derivatives of cationic aminopyridines of formula (IV) are chosen from: 2-[(3,5-diaminopyridin-2-yl)amino]-N,N,N-trimethylethanammonium, 2-[(3,5-diaminopyridin-2-yl)(methyl)amino]-N,N,N-trimethylethanammonium, 1-{2-[(3,5-diaminopyridin-2-yl)amino]ethyl}-1-methylpiperidinium, 1-(3,5-diaminopyridin-2-yl)-N,N,N-trimethylpyrrolidin-3-ammonium, 1-{3-[(3,5-diaminopyridin-2-yl)amino]propyl}-3-(2-hydroxyethyl)-1H-imidazol-3-ium, 1-{3-[(3,5-diaminopyridin-2-yl)amino]propyl}-1-methylpiperidinium, 1-{2-[(3,5-diaminopyridin-2-yl)amino]ethyl}-1-methylpyrrolidinium, 1-{3-[(3,5-diaminopyridin-2-yl)amino]propyl}-1-methylpyrrolidinium, 1-{2-[(3,5-diaminopyridin-2-yl)amino]ethyl}-3-methyl-1H-imidazol-3-ium, 4-{3-[(3,5-diaminopyridin-2-yl)amino]propyl}-4-methylmorpholin-4-ium, 4-{2-[(3,5-diaminopyridin-2-yl)amino]ethyl}-4-methylmorpholin-4-ium, 1-[2-({2-[(3,5-diaminopyridin-2-yl)amino]ethyl}amino)ethyl]-1-methylpiperidinium, 1-[2-({2-[(3,5-diaminopyridin-2-yl)amino]ethyl}amino)ethyl]-1-methylpyrrolidinium, 1-[2-({2-[(3,5-diaminopyridin-2-yl)amino]ethyl}amino)ethyl]-3-methyl-1H-imidazol-3-ium, 4-[2-({2-[(3,5-diaminopyridin-2-yl)amino]ethyl}amino)ethyl]-4-methylmorpholin-4-ium, 2-({2-[(3,5-diaminopyridin-2-yl)amino]ethyl}amino)-N,N,N-trimethylethanammonium, 3-({2-[(3,5-diaminopyridin-2-yl)amino]ethyl}amino)-N,N,N-trimethylpropan-1-ammonium, 2-{2-[(3,5-diaminopyridin-2-yl)amino]ethoxy}-N,N,N-trimethylethanammonium, 3-{2-[(3,5-diaminopyridin-2-yl)amino]ethoxy}-N,N,N-trimethylpropan-1-ammonium, 1-(2-{2-[(3,5-diaminopyridin-2-yl)amino]ethoxy}ethyl)-1-methylpiperidinium, 1-(2-{2-[(3,5-diaminopyridin-2-yl)amino]ethoxy}ethyl)-1-methylpyrrolidinium, 1-{3-[(3,5-diaminopyridin-2-yl)amino]propyl}-3-methyl-1H-imidazol-3-ium, 1-[3-({2-[(3,5-diaminopyridin-2-yl)amino]ethyl}amino)propyl]-3-methyl-1H-imidazol-3-ium, 4-[3-({2-[(3,5-diaminopyridin-2-yl)amino]ethyl}amino)propyl]-1,1-dimethylpiperazin-1-ium, 1-(3-{2-[(3,5-diaminopyridin-2-yl)amino]ethoxy}propyl)-1-methylpiperidinium, 4-[3-({2-[(3,5-diaminopyridin-2-yl)amino]ethyl}amino)propyl]-4-methylmorpholin-4-ium, 3-({2-[(3,5-diaminopyridin-2-yl)amino]ethyl}amino)-N-ethyl-N-methyl-N-propylpropan-1-ammonium, 3-[(3,5-diaminopyridin-2-yl)amino]-N,N,N-trimethylpropan-1-ammonium, 3-[(3,5-diaminopyridin-2-yl)(methyl)amino]-N,N,N-trimethylpropan-1-ammonium, 3-[(3,5-diaminopyridin-2-yl)oxy]-N,N,N-trimethylpropan-1-ammonium, 1-{2-[(3,5-diaminopyridin-2-yl)amino]ethyl}-3-(2-hydroxyethyl)-1H-imidazol-3-ium, 4-(3,5-diaminopyridin-2-yl)-1-(2-hydroxyethyl)-1-methylpiperazin-1-ium, 4-(3,5-diaminopyridin-2-yl)-1,1-bis(2-hydroxyethyl)piperazin-1-ium, 4-(3,5-diaminopyridin-2-yl)-(2-trimethylethan)-morpholin-ammonium, 4-(3,5-diaminopyridin-2-yl)-(2-methyldiethylethan)-morpholin-ammonium, 4-(3,5-diaminopyridin-2-yl) morpholin}2-1,1 dimethylpyrrolidinium, (3,5-diaminopyridin-2-yl)-3-trimethyl piperidin-ammonium, (3,5-diaminopyridin-2-yl)-4-trimethyl piperidin-ammonium, and 4-(3,5-diaminopyridin-2-yl)-1,1-dimethylpiperazin-1-ium.

18. The composition according to claim 1, wherein the 4-aminoindole derivatives of formula (V) are chosen from the derivatives of formula (V'):

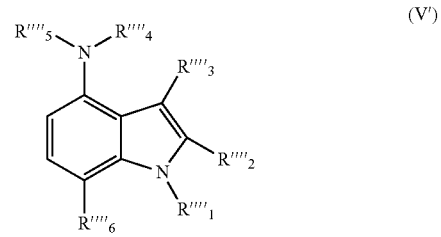

wherein:

$R''_1$ is chosen from:
  hydrogen atoms; and
  saturated $C_1$-$C_4$ alkyl radicals optionally substituted with a hydroxyl radical;

$R''_2$ and $R''_3$, which may be identical or different, are chosen from:
  hydrogen atoms;
  $C_1$-$C_6$ alkyl radicals optionally substituted with at least one hydroxyl radical;
  carboxyl radicals;
  $C_1$-$C_4$ alkyl carboxylate radicals; and
  radicals $CONR''''_7R''''_8$, $R''_4$ and $R''_5$ are hydrogen atoms;

$R''_6$ is chosen from:
  linear and branched $C_1$-$C_6$ alkyl radicals;
  carboxyl radicals;
  $C_1$-$C_6$ alkyl carboxylates;
  carboxamide radicals;
  $(C_1$-$C_6)$alkoxy$(C_1$-$C_6)$alkyloxy radicals;
  $C_1$-$C_6$ alkoxy radicals and $C_1$-$C_6$ hydroxyalkoxy radicals; and
  radicals $O$-Ak-$NR''''_9R''''_{10}$ wherein Ak is chosen from linear $C_1$-$C_6$ and branched $C_3$-$C_6$ divalent alkylene radicals, optionally interrupted with a radical $NR''''_7$;

R''''$_7$ and R''''$_8$ independently are chosen from hydrogen atoms and $C_1$-$C_6$ alkyl radicals optionally substituted with a hydroxyl radical;

R''''$_9$ and R''''$_{10}$, which may be identical or different, are chosen from saturated linear $C_1$-$C_4$ alkyl radicals and unsaturated linear $C_2$-$C_4$ alkyl radicals;

R''''$_9$ and R''''$_{10}$ may form, with the nitrogen that bears them, a saturated or unsaturated 5- to 8-membered heterocycle, one of the chain members optionally being chosen from oxygen atoms and radicals NR''''$_{11}$ wherein R''''$_{11}$ is chosen from hydrogen atoms and $C_1$-$C_4$ alkyl radicals, optionally substituted with OH.

19. The composition according to claim 1, wherein the 4-aminoindole derivatives of formula (V) are chosen from:

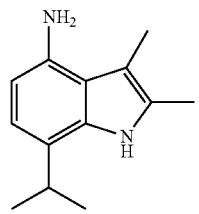

2,3-dimethyl-7-(propan-2-yl)-1H-indol-4-amine

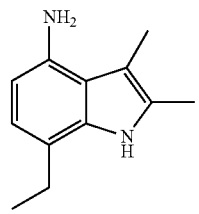

7-ethyl-2,3-dimethyl-1H-indol-4-amine

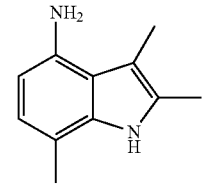

2,3,7-trimethyl-1H-indol-4-amine

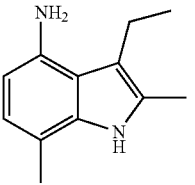

3-ethyl-2,7-dimethyl-1H-indol-4-amine

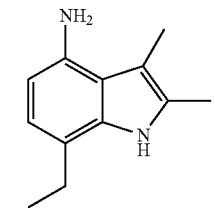

7-ethyl-2,3-dimethyl-1H-indol-4-amine

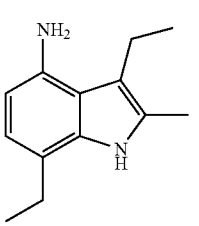

3,7-diethyl-2-methyl-1H-indol-4-amine

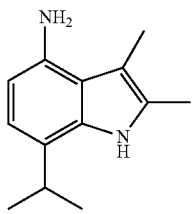

2,3-dimethyl-7-(propan-2-yl)-1H-indol-4-amine

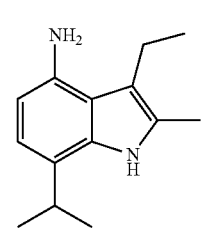

3-ethyl-2-methyl-7-(propan-2yl)-1H-indol-4-amine

-continued

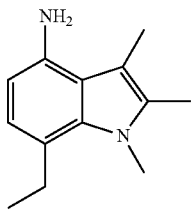

7-ethyl-1,2,3-trimethyl-1H-indol-4-amine

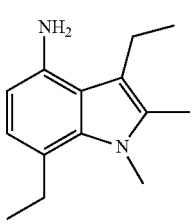

3,7-diethyl-1,2-dimethyl-1H-indol-4-amine

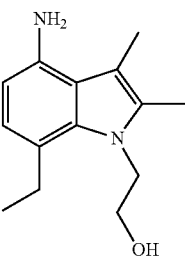

2-(4-amino-7-ethyl-2,3-dimethyl-1H-indol-1-yl)ethanol

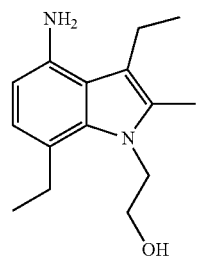

2-(4-amino-3,7-diethyl-2-methyl-1H-indol-1-yl)ethanol

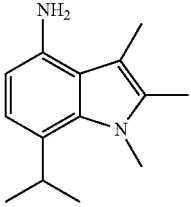

1,2,3-trimethyl-7-(propan-2-yl)-1H-indol-4-amine

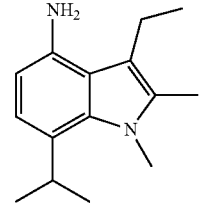

3-ethyl-1,2-dimethyl-7-(propan-2-yl)-1H-indol-4-amine

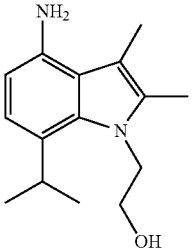

2-[4-amino-2,3-dimethyl-7-(propan-2-yl)-1H-indol-1-yl]ethanol

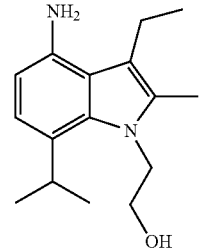

2-[4-amino-3-ethyl-2-methyl-7-(propan-2-yl)-1H-indol-1-yl]ethanol

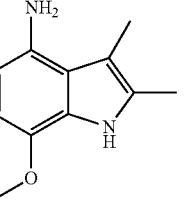

7-methoxy-2,3-dimethyl-1H-indol-4-amine

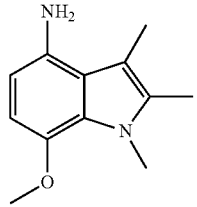

7-methoxy-1,2,3-trimethyl-1H-indol-4-amine

-continued

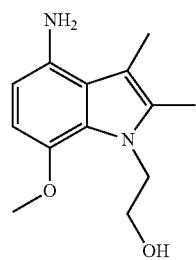

2-(4-amino-7-methoxy-2,3-dimethyl-1H-indol-1-yl]ethanol

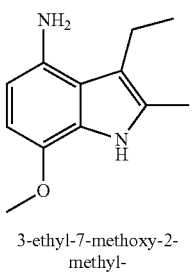

3-ethyl-7-methoxy-2-methyl-1H-indol-4-amine

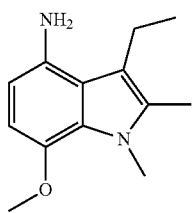

3-ethyl-7-methoxy-1,2-dimethyl-1H-indol-4-amine 3-ethyl-7-methoxy-1,2-dimethyl-1H-indol-4-amine

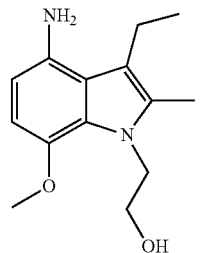

2-(4-amino-3-ethyl-7-methoxy-2-methyl-1H-indol-1-yl]ethanol 7-ethoxy-2,3-dimethyl-1H-indol-4-amine

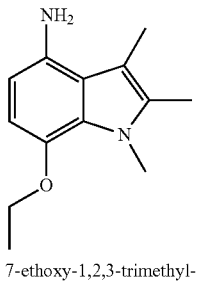

7-ethoxy-1,2,3-trimethyl-1H-indol-4-amine 12-(4-amino-7-ethoxy-2,3-dimethyl-1H-indol-1-yl)ethanol

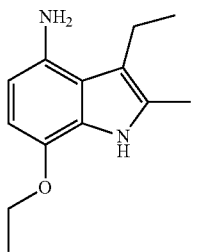

7-ethoxy-3-ethyl-2-methyl-1H-indol-4-amine 7-ethoxy-3-ethyl-1,2-dimethyl-1H-indol-4-amine -continued

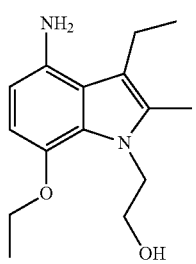

2-(4-amino-7-ethoxy-3-ethyl-2-methyl-1H-indol-1-yl)ethanol

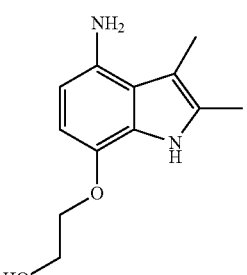

2-[(4-amino-2,3-dimethyl-1H-indol-7-yl)oxy]ethanol

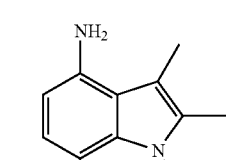

2-[(4-amino-1,2,3-trimethyl-1H-indol-7-yl)oxy]ethanol

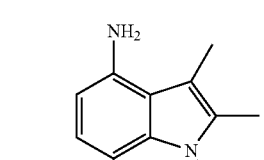

2-[4-amino-7-(2-hydroxyethoxy)-2,3-dimethyl-1H-indol-1-yl]ethanol

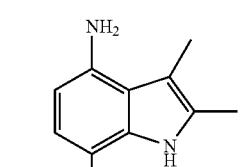

7-[2-(dimethylamino)ethoxy]-2,3-dimethyl-1H-indol-4-amine

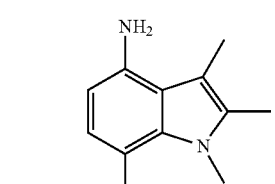

7-[2-(dimethylamino)ethoxy]-1,2,3-trimethyl-1H-indol-4-amine

2-{4-amino-7-[2-(dimethylamino)ethoxy]-2,3-dimethyl-1H-indol-1-yl}ethanol

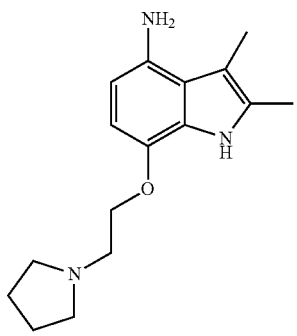

2,3-dimethyl-7-[2-(pyrrolidin-1-yl)ethoxy]-1H-indol-4-amine

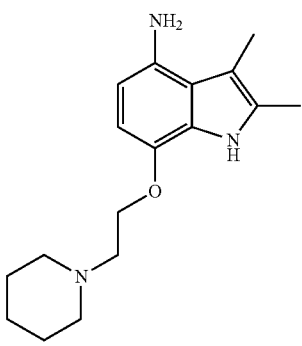

2,3-dimethyl-7-[2-(piperidin-1-yl)ethoxy]-1H-indol-4-amine

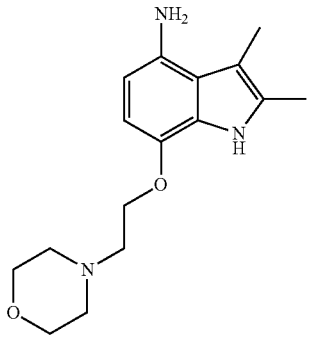

2,3-dimethyl-7-[2-(morpholin-4-yl)ethoxy]-1H-indol-4-amine

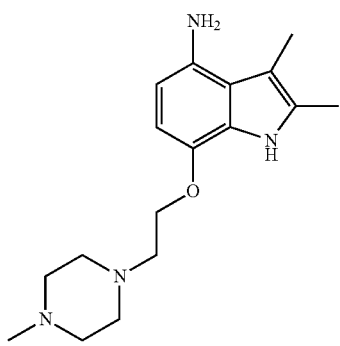

2,3-dimethyl-7-[2-(4-methylpiperazin-1-yl)ethoxy]-1H-indol-4-amine

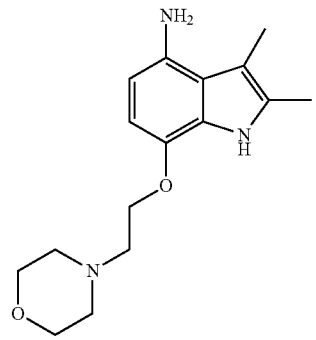

2,3-dimethyl-7-[2-(morpholin-4-yl)ethoxy]-1H-indol-4-amine

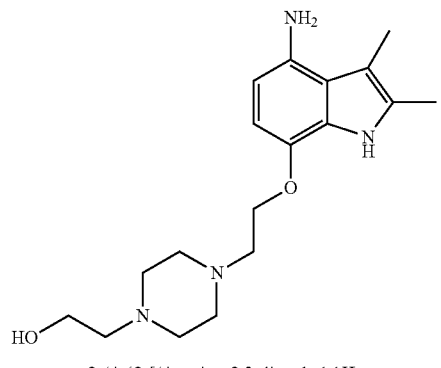

2-(4-{2-[(4-amino-2,3-dimethyl-1H-indol-7-yl)oxy]ethyl}piperazin-1-yl)ethanol

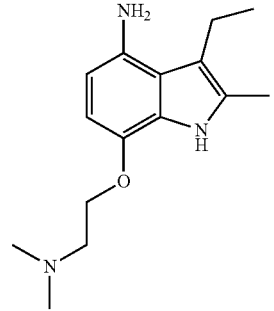

7-[2-(dimethylamino)ethoxy]-3-ethyl-2-methyl-1H-indol-4-amine

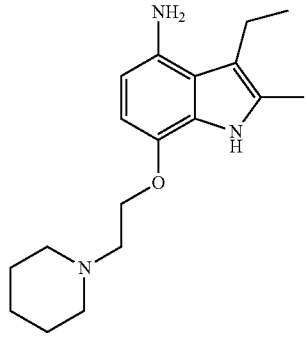

3-ethyl-2-methyl-7-[2-(piperidin-1-yl)ethoxy-1H-indol-4-amine

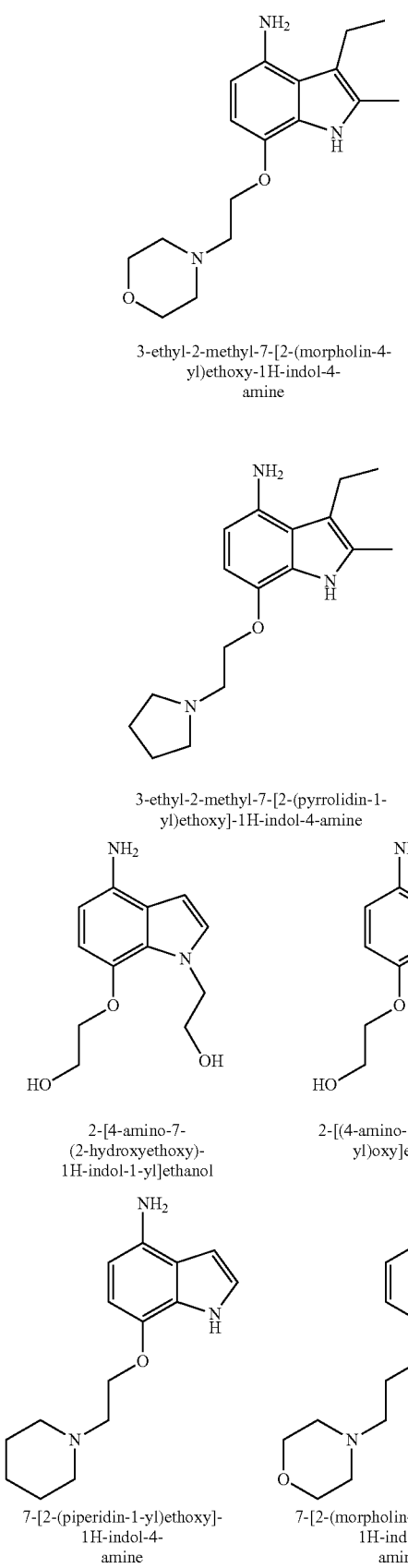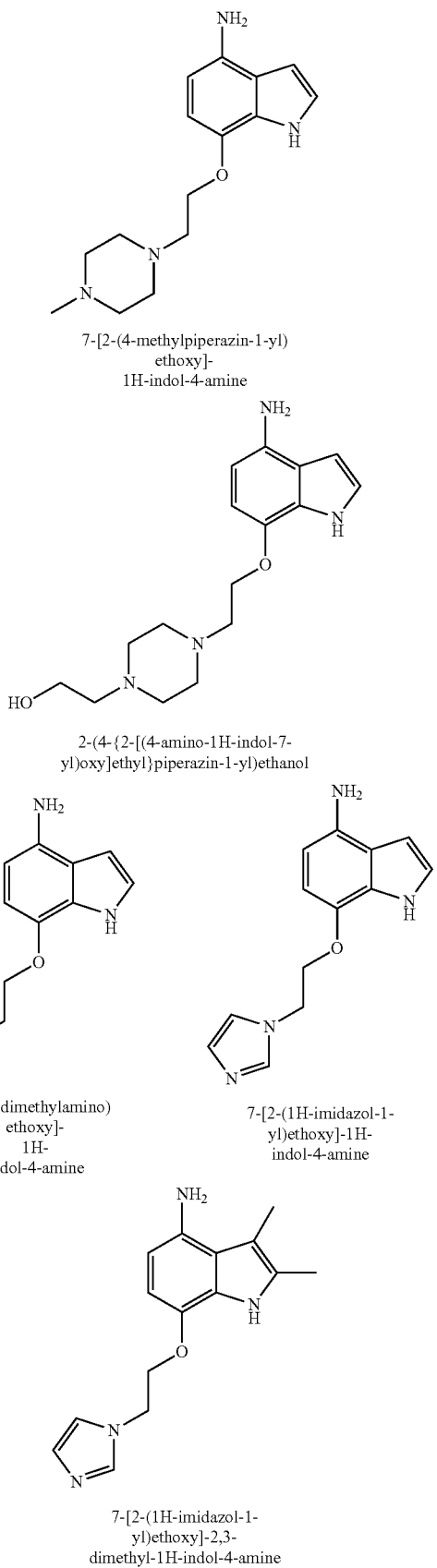

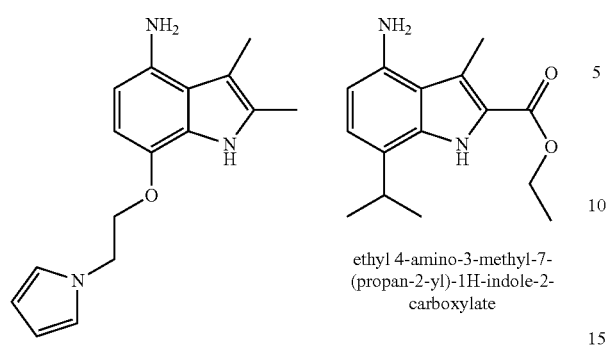

2,3-dimethyl-7-[2-(1H-pyrrol-1-yl)ethoxy]-1H-indol-4-amine ethyl 4-amino-3-methyl-7-(propan-2-yl)-1H-indole-2-carboxylate

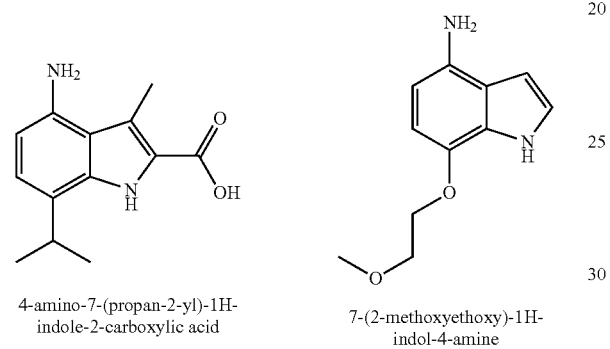

4-amino-7-(propan-2-yl)-1H-indole-2-carboxylic acid 7-(2-methoxyethoxy)-1H-indol-4-amine

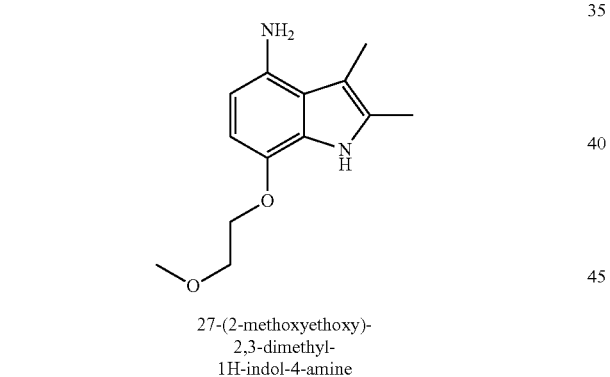

27-(2-methoxyethoxy)-2,3-dimethyl-1H-indol-4-amine

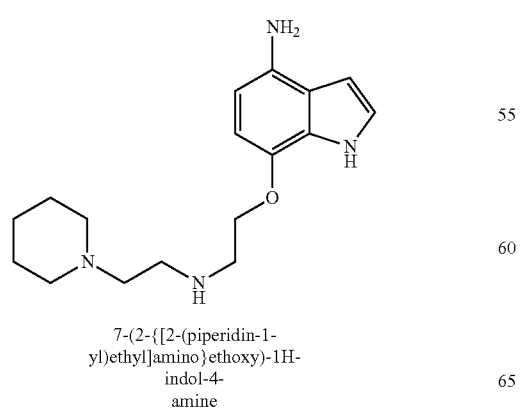

7-(2-{[2-(piperidin-1-yl)ethyl]amino}ethoxy)-1H-indol-4-amine

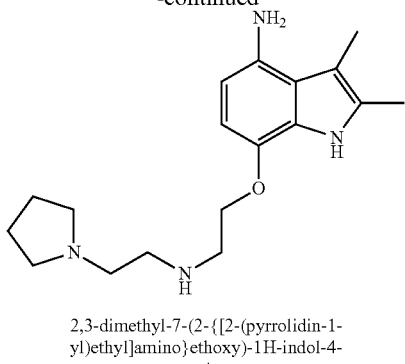

2,3-dimethyl-7-(2-{[2-(pyrrolidin-1-yl)ethyl]amino}ethoxy)-1H-indol-4-amine

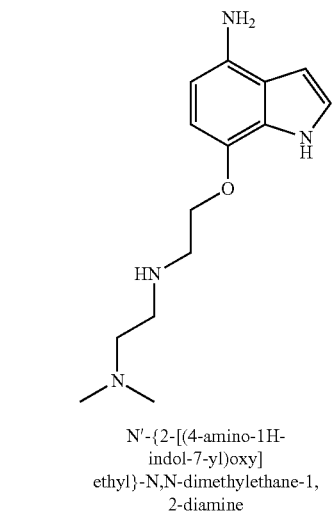

N'-{2-[(4-amino-1H-indol-7-yl)oxy]ethyl}-N,N-dimethylethane-1,2-diamine

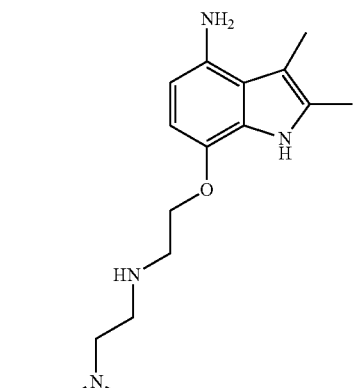

N'-{2-[(4-amino-2,3-dimethyl-1H-indol-7-yl)oxy]ethyl}-N,N-dimethylethane-1,2-diamine

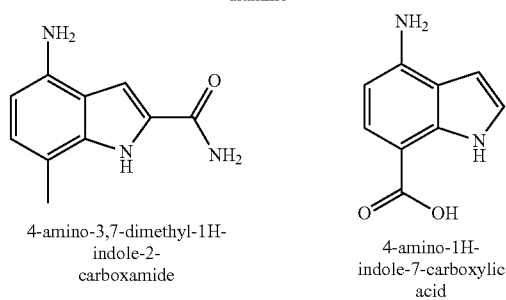

4-amino-3,7-dimethyl-1H-indole-2-carboxamide 4-amino-1H-indole-7-carboxylic acid

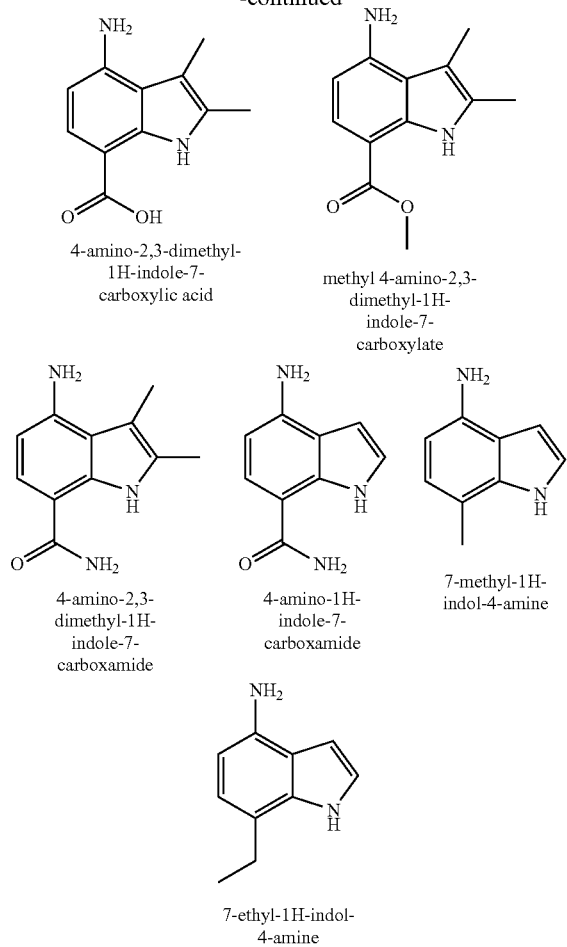

4-amino-2,3-dimethyl-1H-indole-7-carboxylic acid methyl 4-amino-2,3-dimethyl-1H-indole-7-carboxylate 4-amino-2,3-dimethyl-1H-indole-7-carboxamide 4-amino-1H-indole-7-carboxamide 7-methyl-1H-indol-4-amine 7-ethyl-1H-indol-4-amine and addition salts, solvates and solvates of the salts thereof.

20. The composition according to claim 1, further comprising at least one oxidizing agent.

21. A process for dyeing keratin fibers, comprising applying to the keratin fibers in the presence of at least one oxidizing agent for a time that is sufficient to develop the desired coloration, a composition comprising, in a suitable dyeing medium, at least four oxidation dye precursors, including:

A) at least one oxidation base chosen from:
A1) pyrazolopyridines of formula (I), pyrazolopyridines of formula (II), and the addition salts, solvates and solvates of the salts thereof:

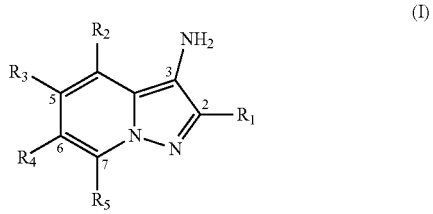
(I)

wherein:
$R_1$, $R_2$, $R_3$, $R_4$ and $R_5$ independently are chosen from hydrogen atoms, halogen atoms;
radicals —$NHSO_3H$; hydroxyl radicals; radicals ($C_1$-$C_4$) alkyl; radicals ($C_1$-$C_4$)alkoxy; radicals ($C_1$-$C_4$)alkylthio; mono($C_1$-$C_4$)alkylamino; radicals di($C_1$-$C_4$)alkylamino wherein the two alkyl groups may form, together with the nitrogen atom to which they are attached, a ring that is optionally interrupted with at least one atom chosen from nitrogen, oxygen and sulfur atoms; heterocycles; nitro radicals; phenyl radicals; carbonyl radicals; ($C_1$-$C_4$)alkoxycarbonyl radicals; carboxamido radicals; cyano radicals; amino radicals; sulfonyl radicals; radicals —$CO_2H$, radicals —$SO_3H$; radicals —$PO_3H_2$; radicals —$PO_4H_2$; and groups

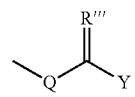

wherein R''' is chosen from oxygen and nitrogen atoms, Q is chosen from oxygen atoms, groups NH and NH($C_1$-$C_4$)alkyl, and Y is chosen from hydroxyl, amino, $C_1$-$C_4$ alkyl, ($C_1$-$C_4$) alkoxy, ($C_1$-$C_4$)alkylamino and di($C_1$-$C_4$)alkylamino radicals;

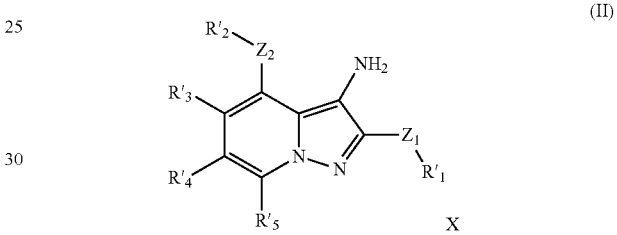
(II)

wherein:
$Z_1$ and $Z_2$ independently are chosen from:
  covalent single bonds;
  divalent radicals chosen from:
    radicals —$O(CH_2)_p$—, wherein p is an integer ranging from 0 to 6;
    radicals —$NR'_6(CH_2)_q(C_6H_4)_t$—, wherein q is an integer ranging from 0 to 6, t is chosen from 0 and 1, and $R'_6$ is chosen from hydrogen atoms and $C_1$-$C_6$ alkyl radicals optionally substituted with at least one hydroxyl group;
$Z_1$ may also be chosen from divalent radicals —S—, —SO— and —$SO_2$— when $R'_1$ is a methyl radical;
$R'_1$ and $R'_2$ independently are chosen from:
  hydrogen atoms;
  $C_1$-$C_{10}$ alkyl radicals, which are optionally substituted and optionally interrupted with a group chosen from heteroatoms, O, N, Si, S, SO and $SO_2$;
  halogen atoms;
  $SO_3H$ radicals;
  5- to 8-membered rings which are chosen from substituted and unsubstituted, saturated, unsaturated and aromatic, optionally comprising at least one heteroatom and groups chosen from N, O, S, $SO_2$ and —CO—, the ring optionally being cationic and optionally substituted with a cationic radical;
  groups —$N^+R_{17}R_{18}R_{19}$, wherein $R_{17}$, $R_{18}$ and $R_{19}$ are independently chosen from linear and branched $C_1$-$C_5$ alkyls optionally substituted with at least one hydroxyl group;
when $Z_1$ or, respectively, $Z_2$ is a covalent bond, then $R'_1$ or, respectively, $R'_2$ may be chosen from:
  optionally substituted $C_1$-$C_6$ alkylcarbonyl radicals; and —O—CO—R, —CO—O—R, NR—CO—R' and —CO—NRR', wherein R and R' independently are chosen from hydrogen atoms and optionally substituted $C_1$-$C_6$ alkyl radicals;

$R'_3$, $R'_4$ and $R'_5$, which may be identical or different, are chosen from:
hydrogen atoms;
hydroxyl radicals;
$C_1$-$C_6$ alkoxy radicals;
$C_1$-$C_6$ alkylthio radicals;
amino radicals;
monoalkylamino radicals;
$C_1$-$C_6$ dialkylamino radicals wherein the alkyl radicals may form, with the nitrogen atom to which they are attached, a saturated, unsaturated, aromatic or non-aromatic 5- to 8-membered heterocycle, which may comprise at least one group chosen from heteroatoms, N, O, S, $SO_2$ and CO, the heterocycle optionally being cationic, and optionally substituted with a cationic radical;
optionally substituted $C_1$-$C_6$ alkylcarbonyl radicals;
radicals —O—CO—R, —CO—O—R, NR—CO—R' and —CO—NRR' wherein R and R' independently are chosen from hydrogen atoms and optionally substituted $C_1$-$C_6$ alkyl radicals;
halogen atoms;
—$NHSO_3H$ radicals;
optionally substituted $C_1$-$C_4$ alkyl radicals; and
saturated, unsaturated and aromatic, optionally substituted carbon-based rings;
$R'_3$, $R'_4$ and $R'_5$, may form in pairs a partially saturated or unsaturated ring;

X is chosen from ions and group of ions that provide the electronegativity of the derivative of formula (II);
with the proviso that at least one of the groups $R'_1$ and $R_2$ is a cationic radical; and A2) diamino-N,N-dihydropyrazolone derivatives of formula (III), and the addition salts, solvates and solvates of the salts thereof:

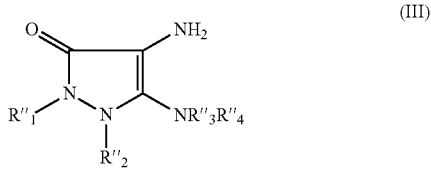

(III)

wherein:
$R''_1$, $R''_2$, $R''_3$ and $R''_4$ independently are chosen from:
linear and branched $C_1$-$C_6$ alkyl radicals optionally substituted with at least one radical chosen from radicals $OR''_5$, radicals $NR''_6R''_7$, carboxyl radicals, sulfonic radicals, carboxamido radicals $CONR''_6R''_7$, sulfonamido radicals $SO_2NR''_6R''_7$, heteroaryls, aryls optionally substituted with at least one group chosen from $(C_1$-$C_4)$alkyl, hydroxyl, $C_1$-$C_2$ alkoxy, amino and (di)alkyl$(C_1$-$C_2)$amino groups;
aryl radicals optionally substituted with at least one group chosen from $(C_1$-$C_4)$alkyl, hydroxyl, $C_1$-$C_2$ alkoxy, amino and (di)alkyl$(C_1$-$C_2)$amino groups;
5- and 6-membered heteroaryl radicals, optionally substituted with at least one radical chosen from $(C_1$-$C_4)$alkyl and $(C_1$-$C_2)$alkoxy;
$R''_3$ and $R''_4$ may independently also be chosen from hydrogen atoms;

$R''_5$, $R''_6$ and $R''_7$, which may be identical or different, are chosen from:
hydrogen atoms;
linear and branched $C_1$-$C_4$ alkyl radicals optionally substituted with at least one radical chosen from hydroxyl radicals, $C_1$-$C_2$ alkoxy radicals, carboxamido radicals $CONR''_8R''_9$, sulfonyl radicals $SO_2R''_8$, and aryl radicals optionally substituted with a group chosen from $(C_1$-$C_4)$alkyl, hydroxyl, $C_1$-$C_2$ alkoxy, amino and (di)alkyl$(C_1$-$C_2)$amino groups;
$R''_6$ and $R''_7$, which may be identical or different, may also be chosen from carboxamido radicals $CONR''_8R''_9$ and sulfonyl radicals $SO_2R''_8$;
$R''_8$ and $R''_9$, which may be identical or different, are chosen from hydrogen atoms; linear and branched $C_1$-$C_4$ alkyl radicals optionally substituted with at least one radicals chosen from hydroxyl and $C_1$-$C_2$ alkoxy radicals;
$R''_1$ and $R''_2$ and $R''_3$ and $R''_4$ may form, with the nitrogen atoms to which they are attached, a saturated or unsaturated 5- to 7-membered heterocycle optionally substituted with at least one radical chosen from halogen atoms, amino radicals, (di)alkyl$(C_1$-$C_4)$amino radicals, hydroxyl radicals, carboxyl radicals, carboxamido radicals, $(C_1$-$C_2)$alkoxy radicals, and $C_1$-$C_4$ alkyl radicals optionally substituted with at least one radicals chosen from hydroxyl, amino, (di)alkylamino, alkoxy, carboxyl and sulfonyl radicals;
$R''_3$ and $R''_4$ may also form, together with the nitrogen atom to which they are attached, a 5- or 7-membered heterocycle wherein the carbon atoms may be replaced with an optionally substituted atom chosen from oxygen and nitrogen atoms;

B) at least one coupler chosen from:
B1) derivatives of cationic aminopyridines of formula (IV) and the addition salts, solvates and solvates of the salts thereof:

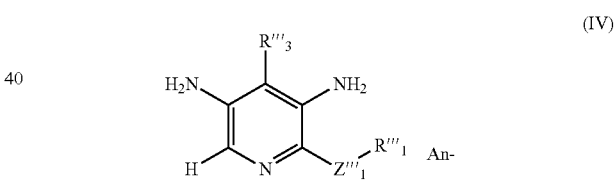

(IV)

wherein the group $Z'''_1R'''_1$ bears a cationic charge;
$Z'''_1$ is chosen from oxygen atoms and $NR'''_2$ groups;
$R'''_2$ is chosen from hydrogen atoms, linear and branched $C_1$-$C_4$ alkyl radicals, benzyl radicals, and acetyl radicals;
$R'''_1$ is chosen from
saturated, linear and branched $C_1$-$C_{10}$ alkyl radicals, optionally substituted and optionally interrupted with a cationic radical, optionally interrupted with at least one oxygen atom and with at least one group $NR'''_2$, optionally substituted with at least one radical chosen from hydroxyl, alkoxy and $C_1$-$C_4$ hydroxyalkyl radicals; and
$R'''_3$ is chosen from saturated, and saturated and aromatic 5- to 8-membered heterocycles optionally substituted with at least one radical chosen from $C_1$-$C_4$ alkyl, hydroxyl, $C_1$-$C_4$ alkoxy, amino, $(C_1$-$C_4)$alkylamino, di$(C_1$-$C_4)$alkylamino, thio, $(C_1$-$C_4)$alkylthio, carboxyl, $(C_1$-$C_4)$alkylcarbonyl, sulfonyl, amido and $C_1$-$C_4$ hydroxyalkyl radicals;
provided that when $Z'''_1$ is $NR'''_2$, then
$R'''_1$ and $R'''_2$ may form, together with the nitrogen atom to which they are attached, a cationic, saturated or unsaturated 5- to 8-membered heterocycle, optionally substituted with at least one radical chosen from $C_1$-$C_{10}$ alkyl radicals, hydroxyl, $C_1$-$C_4$ alkoxy, amino, ($C_1$-$C_4$)alkylamino, di($C_1$-$C_4$)alkylamino, thio, ($C_1$-$C_4$)alkylthio, carboxyl, ($C_1$-$C_4$)alkylcarbonyl, sulfonyl, amido and $C_1$-$C_4$ hydroxyalkyl radicals, wherein the heterocycle optionally comprises at least one heteroatom chosen from N and O; and $R'''_1$ and $R'''_2$ may form, together with the nitrogen atom to which they are attached, a non-cationic, saturated or unsaturated 5- to 8-membered heterocycle, substituted with a cationic radical and optionally substituted with at least one radical chosen from $C_1$-$C_{10}$ alkyl radicals, hydroxyl, $C_1$-$C_4$ alkoxy, amino, ($C_1$-$C_4$)alkylamino, di($C_1$-$C_4$)alkylamino, thio, ($C_1$-$C_4$)alkylthio, carboxyl, ($C_1$-$C_4$)alkylcarbonyl, sulfonyl, amido and $C_1$-$C_4$ hydroxyalkyl radicals;

$R'''_3$ is chosen from hydrogen atoms, halogens chosen from fluorine, chlorine and bromine, linear and branched $C_1$-$C_4$ alkyl radicals, carboxyl (—COOH) and ($C_1$-$C_4$)alkoxycarbonyl radicals;

An- is chosen from at least one anion;

B2) 4-aminoindole derivatives of formula (V), and addition salts, solvates and solvates of the salts thereof:

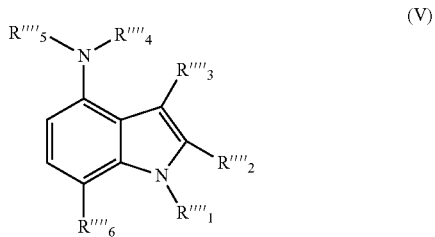

(V)

wherein:

$R''''_1$ is chosen from:
  hydrogen atoms; and
  linear and branched, saturated $C_1$-$C_6$ alkyl radicals, optionally interrupted with an group chosen from oxygen atoms and radicals $NR''''_7$, optionally substituted with a radical chosen from OH and $NR''''_7R''''_8$;

$R''''_2$ and $R''''_3$, which may be identical or different, are chosen from:
  hydrogen atoms;
  $C_1$-$C_6$ alkyl radicals, optionally substituted with at least one hydroxyl radical;
  $C_1$-$C_6$ alkyl carboxylate radicals;
  carboxyl radicals; and
  radicals $CONR''''_7R''''_8$, $R''''_4$ and $R''''_5$, which may be identical or different, are chosen from:
  hydrogen atoms; and
  $C_1$-$C_8$ alkyl radicals;

$R''''_6$ is chosen from:
  halogen atoms;
  linear and branched $C_1$-$C_{10}$ alkyl radicals, optionally interrupted with a heteroatom chosen from O and $NR''''_9$, and optionally substituted with at least one radical, which may be identical or different, chosen from OH and $NR''''_7R''''_8$;
  carboxyl radicals;
  $C_1$-$C_{10}$ alkyl carboxylate radicals;
  radicals $CONR''''_7R''''_8$;
  $C_1$-$C_{10}$ alkoxy radicals and $C_1$-$C_{10}$ (poly)hydroxyalkoxy radicals;
  (poly)($C_1$-$C_{10}$)alkoxy($C_1$-$C_{10}$)alkyloxy radicals; and
  radicals O-Ak-$NR''''_9R''''_{10}$ wherein Ak is chosen from linear $C_1$-$C_8$ and branched $C_3$-$C_8$ divalent alkylene radicals, optionally interrupted with at least one group chosen from oxygen atom and groups $NR''''_7$;

$R''''_7$ and $R''''_8$, which may be identical or different, are chosen from:
  hydrogen atoms;
  $C_1$-$C_8$ alkyl radicals optionally substituted with at least one hydroxyl radical;

$R''''_9$ and $R''''_{10}$, which may be identical or different, are chosen from linear and branched, saturated and unsaturated $C_1$-$C_4$ alkyl radicals;

$R''''_9$ and $R''''_{10}$ may form, with the nitrogen that bears them, a saturated or unsaturated 5- to 8-membered heterocycle, one of the chain members optionally being chosen from oxygen atoms and radicals $NR''''_{11}$ wherein $R''''_{11}$ is chosen from hydrogen atoms and $C_1$-$C_4$ alkyl radicals, optionally substituted with at least one radical chosen from OH and $NR''''_7R''''_8$;

B3) 5-amino-6-chloro-2-methylphenol of formula (VI), and addition salts, solvates and solvates of the salts thereof:

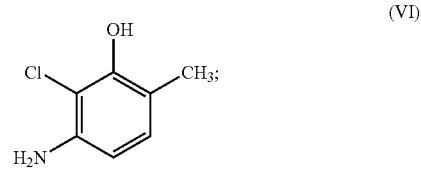

(VI)

B4) 6-hydroxybenzomorpholine of formula (VII), and addition salts, solvates and solvates of the salts thereof:

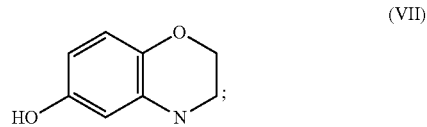 [SMILES: Oc1ccc2c(c1)NCCO2]

(VII)

B5) 2-methyl-5-hydroxyethylaminophenol of formula (VIII), and addition salts, solvates and solvates of the salts thereof:

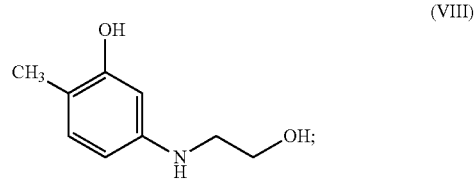

(VIII)

and

B6) 2-amino-3-hydroxypyridine of formula (IX), and addition salts, solvates and solvates of the salts thereof:

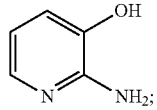
(IX)

and

C) a basifying agent chosen from monoethanolamine.

22. A multi-compartment device comprising:

a first compartment comprising a composition comprising, in a suitable dyeing medium, at least four oxidation dye precursors, including:

A) at least one oxidation base chosen from:

A1) pyrazolopyridines of formula (I), pyrazolopyridines of formula (II), and the addition salts, solvates and solvates of the salts thereof:

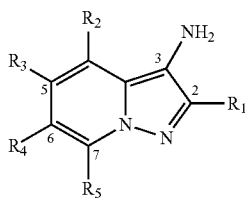
(I)

wherein:

$R_1$, $R_2$, $R_3$, $R_4$ and $R_5$, which may be identical or different, are chosen from hydrogen atoms, halogen atoms; radicals —$NHSO_3H$; hydroxyl radicals; radicals ($C_1$-$C_4$)alkyl; radicals ($C_1$-$C_4$)alkoxy; radicals ($C_1$-$C_4$)alkylthio; mono($C_1$-$C_4$) alkylamino; radicals di($C_1$-$C_4$)alkylamino wherein the two alkyl groups may form, together with the nitrogen atom to which they are attached, a ring that is optionally interrupted with at least one atom chosen from nitrogen, oxygen and sulfur atoms; heterocycles; nitro radicals; phenyl radicals; carbonyl radicals; ($C_1$-$C_4$)alkoxycarbonyl radicals; carboxamido radicals; cyano radicals; amino radicals; sulfonyl radicals; radicals —$CO_2H$, radicals —$SO_3H$; radicals —$PO_3H_2$; radicals —$PO_4H_2$; and groups

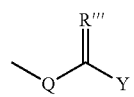

wherein R''' is chosen from oxygen and nitrogen atoms, Q is chosen from oxygen atoms, groups NH and NH($C_1$-$C_4$)alkyl, and Y is chosen from hydroxyl, amino, $C_1$-$C_4$ alkyl, ($C_1$-$C_4$) alkoxy, ($C_1$-$C_4$)alkylamino and di($C_1$-$C_4$)alkylamino radicals;

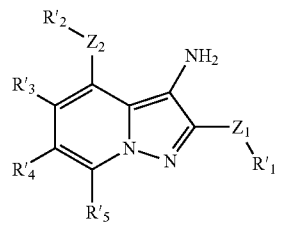
(II)

wherein:

$Z_1$ and $Z_2$, which may be identical or different, are chosen from:
covalent single bonds;
divalent radicals chosen from:
radicals —$O(CH_2)_p$—, wherein p is an integer ranging from 0 to 6;
radicals —$NR'_6(CH_2)_q(C_6H_4)_t$—, wherein q is an integer ranging from 0 to 6, t is chosen from 0 and 1, and $R'_6$ is chosen from hydrogen atoms and $C_1$-$C_6$ alkyl radicals optionally substituted with at least one hydroxyl group;

$Z_1$ may also be chosen from divalent radicals —S—, —SO— and —$SO_2$— when $R'_1$ is a methyl radical;

$R'_1$ and $R'_2$ independently are chosen from:
hydrogen atoms;
$C_1$-$C_{10}$ alkyl radicals, which are optionally substituted and optionally interrupted with a group chosen from heteroatoms, O, N, Si, S, SO and $SO_2$;
halogen atoms;
$SO_3H$ radicals;
5- to 8-membered rings which are chosen from substituted and unsubstituted, saturated, unsaturated and aromatic, optionally comprising at least one heteroatom and groups chosen from N, O, S, $SO_2$ and —CO—, the ring optionally being cationic and optionally substituted with a cationic radical;
groups —$N^+R_{17}R_{18}R_{19}$, wherein $R_{17}$, $R_{18}$ and $R_{19}$ are independently chosen from linear and branched $C_1$-$C_5$ alkyls optionally substituted with at least one hydroxyl group;

when $Z_1$ or, respectively, $Z_2$ is a covalent bond, then $R'_1$ or, respectively, $R'_2$ may be chosen from:
optionally substituted $C_1$-$C_6$ alkylcarbonyl radicals; and
—O—CO—R, —CO—O—R, NR—CO—R' and —CO—NRR', wherein R and R' independently are chosen from hydrogen atoms and optionally substituted $C_1$-$C_6$ alkyl radicals;

$R'_3$, $R'_4$ and $R'_5$, which may be identical or different, are chosen from:
hydrogen atoms;
hydroxyl radicals;
$C_1$-$C_6$ alkoxy radicals;
$C_1$-$C_6$ alkylthio radicals;
amino radicals;
monoalkylamino radicals;
$C_1$-$C_6$ dialkylamino radicals wherein the alkyl radicals may form, with the nitrogen atom to which they are attached, a saturated, unsaturated, aromatic or non-aromatic 5- to 8-membered heterocycle, which may comprise at least one group chosen from heteroatoms, N, O, S, $SO_2$ and CO, the heterocycle optionally being cationic, and optionally substituted with a cationic radical;
optionally substituted $C_1$-$C_6$ alkylcarbonyl radicals;

radicals —O—CO—R, —CO—O—R, NR—CO—R' and —CO—NRR' wherein R and R' independently are chosen from hydrogen atoms and optionally substituted $C_1$-$C_6$ alkyl radicals;
halogen atoms;
—NHSO$_3$H radicals;
optionally substituted $C_1$-$C_4$ alkyl radicals; and
saturated, unsaturated and aromatic, optionally substituted carbon-based rings;
R'$_3$, R'$_4$ and R'$_5$, may form in pairs a partially saturated or unsaturated ring;
X is chosen from ions and group of ions that provide the electronegativity of the derivative of formula (II);
with the proviso that at least one of the groups R'$_1$ and R$_2$ is a cationic radical; and
  A2) diamino-N,N-dihydropyrazolone derivatives of formula (III), and the addition salts, solvates and solvates of the salts thereof:

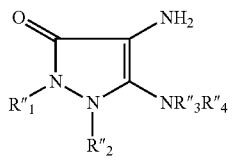

(III)

wherein:
R"$_1$, R"$_2$, R"$_3$ and R"$_4$ independently are chosen from:
  linear and branched $C_1$-$C_6$ alkyl radicals optionally substituted with at least one radical chosen from radicals OR"$_5$, radicals NR"$_6$R"$_7$, carboxyl radicals, sulfonic radicals, carboxamido radicals CONR"$_6$R"$_7$, sulfonamido radicals SO$_2$NR"$_6$R"$_7$, heteroaryls, aryls optionally substituted with at least one group chosen from ($C_1$-$C_4$)alkyl, hydroxyl, $C_1$-$C_2$ alkoxy, amino and (di)alkyl($C_1$-$C_2$)amino groups;
  aryl radicals optionally substituted with at least one group chosen from ($C_1$-$C_4$)alkyl, hydroxyl, $C_1$-$C_2$ alkoxy, amino and (di)alkyl($C_1$-$C_2$)amino groups;
  5- and 6-membered heteroaryl radicals, optionally substituted with at least one radical chosen from ($C_1$-$C_4$)alkyl and ($C_1$-$C_2$)alkoxy;
R"$_3$ and R"$_4$ may also independently be chosen from hydrogen atoms;
R"$_5$, R"$_6$ and R"$_7$, which may be identical or different, are chosen from:
  hydrogen atoms;
  linear and branched $C_1$-$C_4$ alkyl radicals optionally substituted with at least one radical chosen from hydroxyl radicals, $C_1$-$C_2$ alkoxy radicals, carboxamido radicals CONR"$_8$R"$_9$, sulfonyl radicals SO$_2$R"$_8$, and aryl radicals optionally substituted with a group chosen from ($C_1$-$C_4$)alkyl, hydroxyl, $C_1$-$C_2$ alkoxy, amino and (di)alkyl($C_1$-$C_2$)amino groups;
R"$_6$ and R"$_7$, which may be identical or different, may also be chosen from carboxamido radicals CONR"$_8$R"$_9$ and sulfonyl radicals SO$_2$R"$_8$;
R"$_8$ and R"$_9$, which may be identical or different, are chosen from hydrogen atoms; linear and branched $C_1$-$C_4$ alkyl radicals optionally substituted with at least one radicals chosen from hydroxyl and $C_1$-$C_2$ alkoxy radicals;
R"$_1$ and R"$_2$ and R"$_3$ and R"$_4$ may form, with the nitrogen atoms to which they are attached, a saturated or unsaturated 5- to 7-membered heterocycle optionally substituted with at least one radical chosen from halogen atoms, amino radicals, (di)alkyl($C_1$-$C_4$)amino radicals, hydroxyl radicals, carboxyl radicals, carboxamido radicals, ($C_1$-$C_2$)alkoxy radicals, and $C_1$-$C_4$ alkyl radicals optionally substituted with at least one radicals chosen from hydroxyl, amino, (di)alkylamino, alkoxy, carboxyl and sulfonyl radicals;
R"$_3$ and R"$_4$ may also form, together with the nitrogen atom to which they are attached, a 5- or 7-membered heterocycle wherein the carbon atoms may be replaced with an optionally substituted atom chosen from oxygen and nitrogen atoms;
  B) at least one coupler chosen from:
    B1) derivatives of cationic aminopyridines of formula (IV) and the addition salts, solvates and solvates of the salts thereof:

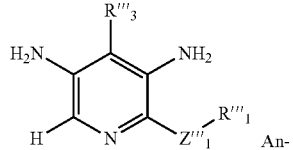

(IV)

wherein the group Z'''$_1$R'''$_1$ bears a cationic charge;
Z'''$_1$ is chosen from oxygen atoms and NR'''$_2$ groups;
R'''$_2$ is chosen from hydrogen atoms, linear and branched $C_1$-$C_4$ alkyl radicals, benzyl radicals, and acetyl radicals;
R'''$_1$ is chosen from
  saturated, linear and branched $C_1$-$C_{10}$ alkyl radicals, optionally substituted and optionally interrupted with a cationic radical, optionally interrupted with at least one oxygen atom and with at least one group NR'''$_2$, optionally substituted with at least one radical chosen from hydroxyl, alkoxy and $C_1$-$C_4$ hydroxyalkyl radicals; and
  R'''$_1$ is chosen from saturated, and saturated and aromatic 5- to 8-membered heterocycles optionally substituted with at least one radical chosen from $C_1$-$C_4$ alkyl, hydroxyl, $C_1$-$C_4$ alkoxy, amino, ($C_1$-$C_4$)alkylamino, di($C_1$-$C_4$)alkylamino, thio, ($C_1$-$C_4$)alkylthio, carboxyl, ($C_1$-$C_4$)alkylcarbonyl, sulfonyl, amido and $C_1$-$C_4$ hydroxyalkyl radicals;
provided that when Z'''$_1$ is NR'''$_2$, then
  R'''$_1$ and R'''$_2$ may form, together with the nitrogen atom to which they are attached, a cationic, saturated or unsaturated 5- to 8-membered heterocycle, optionally substituted with at least one radical chosen from $C_1$-$C_{10}$ alkyl radicals, hydroxyl, $C_1$-$C_4$ alkoxy, amino, ($C_1$-$C_4$)alkylamino, di($C_1$-$C_4$)alkylamino, thio, ($C_1$-$C_4$)alkylthio, carboxyl, ($C_1$-$C_4$)alkylcarbonyl, sulfonyl, amido and $C_1$-$C_4$ hydroxyalkyl radicals, wherein the heterocycle optionally comprises at least one heteroatom chosen from N and O; and
  R'''$_1$ and R'''$_2$ may form, together with the nitrogen atom to which they are attached, a non-cationic, saturated or unsaturated 5- to 8-membered heterocycle, substituted with a cationic radical and optionally substituted with at least one radical chosen from $C_1$-$C_{10}$ alkyl radicals, hydroxyl, $C_1$-$C_4$ alkoxy, amino, ($C_1$-$C_4$)alkylamino, di($C_1$-$C_4$)alkylamino, thio, ($C_1$-$C_4$)alkylthio, carboxyl, ($C_1$-$C_4$)alkylcarbonyl, sulfonyl, amido and $C_1$-$C_4$ hydroxyalkyl radicals;

$R'''_3$ is chosen from hydrogen atoms, halogens chosen from fluorine, chlorine and bromine, linear and branched $C_1$-$C_4$ alkyl radicals, carboxyl (—COOH) and ($C_1$-$C_4$)alkoxycarbonyl radicals;

An- is chosen from at least one anion;

B2) 4-aminoindole derivatives of formula (V), and addition salts, solvates and solvates of the salts thereof:

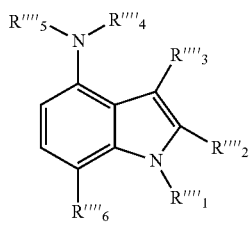

(V)

wherein:

$R''''_1$ is chosen from:
  hydrogen atoms; and
  linear and branched, saturated $C_1$-$C_6$ alkyl radicals, optionally interrupted with an group chosen from oxygen atoms and radicals $NR''''_7$, optionally substituted with a radical chosen from OH and $NR''''_7R''''_8$;

$R''''_2$ and $R''''_3$, which may be identical or different, are chosen from:
  hydrogen atoms;
  $C_1$-$C_6$ alkyl radicals, optionally substituted with at least one hydroxyl radical;
  $C_1$-$C_6$ alkyl carboxylate radicals;
  carboxyl radicals; and
  radicals $CONR''''_7R''''_8$, $R''''_4$ and $R''''_5$, which may be identical or different, are chosen from:
  hydrogen atoms; and
  $C_1$-$C_6$ alkyl radicals;

$R''''_6$ is chosen from:
  halogen atoms;
  linear and branched $C_1$-$C_{10}$ alkyl radicals, optionally interrupted with a heteroatom chosen from O and $NR''''_9$, and optionally substituted with at least one radical, which may be identical or different, chosen from OH and $NR''''_7R''''_8$;
  carboxyl radicals;
  $C_1$-$C_{10}$ alkyl carboxylate radicals;
  radicals $CONR''''_7R''''_8$;
  $C_1$-$C_{10}$ alkoxy radicals and $C_1$-$C_{10}$ (poly)hydroxyalkoxy radicals;
  (poly)($C_1$-$C_{10}$)alkoxy($C_1$-$C_{10}$)alkyloxy radicals; and
  radicals O-Ak-$NR''''_9R''''_{10}$ wherein Ak is chosen from linear $C_1$-$C_8$ and branched $C_3$-$C_8$ divalent alkylene radicals, optionally interrupted with at least one group chosen from oxygen atom and groups $NR''''_7$;

$R''''_7$ and $R''''_8$, which may be identical or different, are chosen from:
  hydrogen atoms;
  $C_1$-$C_8$ alkyl radicals optionally substituted with at least one hydroxyl radical;

$R''''_9$ and $R''''_{10}$, which may be identical or different, are chosen from linear and branched, saturated and unsaturated $C_1$-$C_4$ alkyl radicals;

$R''''_9$ and $R''''_{10}$ may form, with the nitrogen that bears them, a saturated or unsaturated 5- to 8-membered heterocycle, one of the chain members optionally being chosen from oxygen atoms and radicals $NR''''_{11}$ wherein $R''''_{11}$ is chosen from hydrogen atoms and $C_1$-$C_4$ alkyl radicals, optionally substituted with at least one radical chosen from OH and $NR''''_7R''''_8$;

B3) 5-amino-6-chloro-2-methylphenol of formula (VI), and addition salts, solvates and solvates of the salts thereof:

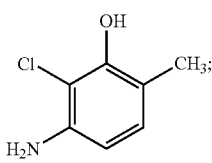

(VI)

B4) 6-hydroxybenzomorpholine of formula (VII), and addition salts, solvates and solvates of the salts thereof:

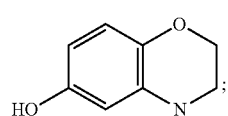

(VII)

B5) 2-methyl-5-hydroxyethylaminophenol of formula (VIII), and addition salts, solvates and solvates of the salts thereof:

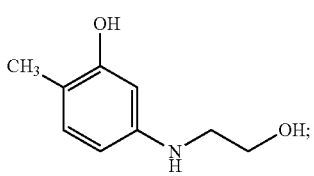

(VIII)

and

B6) 2-amino-3-hydroxypyridine of formula (IX), and addition salts, solvates and solvates of the salts thereof:

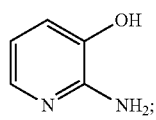

(IX)

and a second compartment comprising at least one oxidizing agent; and

C) a basifying agent chosen from monoethanolamine.

* * * * *

UNITED STATES PATENT AND TRADEMARK OFFICE
CERTIFICATE OF CORRECTION

PATENT NO. : 9,220,671 B2
APPLICATION NO. : 13/994278
DATED : December 29, 2015
INVENTOR(S) : Jean-Marc Ascione et al.

It is certified that error appears in the above-identified patent and that said Letters Patent is hereby corrected as shown below:

Claims

Claim 5, col. 97, lines 17-32, please delete the two chemical structures and insert the two chemical structures below.

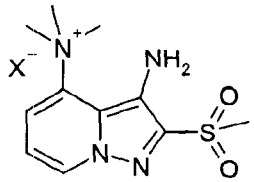
salt of (3-amino-2-methanesulfonylpyrazolo[1,5-a]-pyridin-4-yl)trimethylammonium

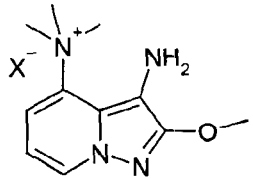
salt of (3-amino-2-methoxy-pyrazolo[1,5-a]pyridin-4-yl)trimethylammonium

-- --.

Claim 18, col. 100, line 44, change "R"1" to -- R""1 --;
    line 48, change "R"2 and R"3" to -- R""2 and R""3 --;
    line 56, change "R"4 and R"5" to -- R""4 and R""5 --; and
    line 57, change "R"6" to -- R""6 --.

Signed and Sealed this
Fifth Day of July, 2016

Michelle K. Lee
*Director of the United States Patent and Trademark Office*